US011697650B2

(12) United States Patent
Kysil et al.

(10) Patent No.: US 11,697,650 B2
(45) Date of Patent: Jul. 11, 2023

(54) COMPOUNDS HAVING TETRAHYDROINDOLIZINE-1-CARBOXAMIDE AS BCL-2 INHIBITORS

(71) Applicant: Eil Therapeutics, Inc., San Diego, CA (US)

(72) Inventors: Volodymyr Kysil, San Diego, CA (US); Vladislav Zenonovich Parchinsky, Moscow (RU); Alexei Pushechnikov, San Diego, CA (US); Alexandre Vasilievich Ivachtchenko, Hallandale Beach, FL (US); Ruben Abagyan, La Jolla, CA (US); Andrew Orry, San Diego, CA (US); Polo Chun-Hung Lam, San Diego, CA (US); Nikolay Savchuk, San Diego, CA (US)

(73) Assignee: Eil Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/692,923

(22) Filed: Mar. 11, 2022

(65) Prior Publication Data
US 2022/0289745 A1 Sep. 15, 2022

Related U.S. Application Data

(60) Provisional application No. 63/160,208, filed on Mar. 12, 2021.

(51) Int. Cl.
*C07D 471/04* (2006.01)
(52) U.S. Cl.
CPC .................. *C07D 471/04* (2013.01)
(58) Field of Classification Search
CPC .................................................... C07D 471/04
USPC .......................................................... 514/299
See application file for complete search history.

(56) References Cited

U.S. PATENT DOCUMENTS

| 9,115,159 | B2* | 8/2015 | Le Tiran ............... C07F 9/6561 |
| 2015/0051189 | A1 | 2/2015 | Le Diguarher et al. |
| 2015/0313911 | A1 | 11/2015 | Le Diguarher et al. |
| 2016/0176848 | A1 | 1/2016 | Le Tiran et al. |
| 2017/0151251 | A1 | 2/2017 | Le Diguarher et al. |
| 2018/0186771 | A1 | 2/2018 | Le Tiran et al. |
| 2019/0359595 | A1 | 8/2019 | Le Tiran et al. |

FOREIGN PATENT DOCUMENTS

WO     2020229429     11/2020

\* cited by examiner

*Primary Examiner* — Niloofar Rahmani
(74) *Attorney, Agent, or Firm* — Sergey B Alyabyev

(57) ABSTRACT

The present invention is generally directed to inhibitors of BCL-2 proteins useful in the treatment of diseases and disorders modulated by said enzyme and having the Formula (I):

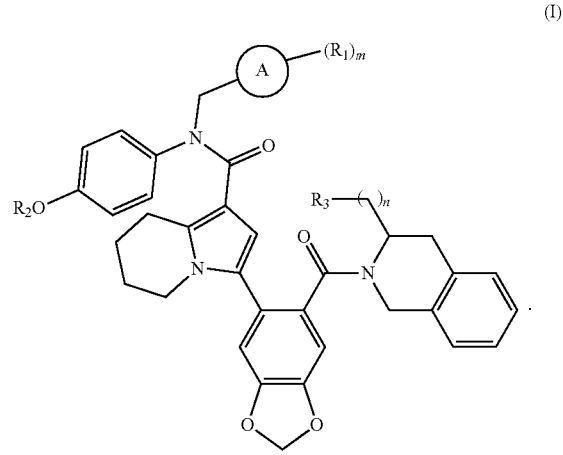

61 Claims, No Drawings

COMPOUNDS HAVING TETRAHYDROINDOLIZINE-1-CARBOXAMIDE AS BCL-2 INHIBITORS

CROSS-REFERENCE TO RELATED APPLICATIONS

This application claims priority to, and the benefit of, U.S. Provisional Application No. 63/160,208, filed Mar. 12, 2021, the contents of which are incorporated by reference in their entirety.

FIELD OF INVENTION

The present invention is directed to inhibitors of B-cell lymphoma 2 (BCL-2) proteins. The inhibitors described herein can be useful in the treatment of diseases or disorders associated with BCL-2. In particular, the invention is concerned with compounds and pharmaceutical compositions inhibiting BCL-2, methods of treating diseases or disorders associated with BCL-2, and methods of synthesizing these compounds.

BACKGROUND OF THE INVENTION

Apoptosis, or programmed cell death, is a physiological process that is crucial for embryonic development and maintenance of tissue homeostasis.

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan a et al., Cell, 2000, 100, 57-70).

The BCL-2 family of proteins plays a major role in tumorogenesis. BCL-2 proteins are characterized based on the presence of BCL-2 homology (BH) domains. The anti-apoptotic proteins contain all the BH1-4 domains; the pro-apoptotic proteins contain either the BID domain only or multiple BH domains. The BH3 domain is necessary in executing the pro apoptotic function of these proteins. In anti-apoptotic proteins, the BH3 domain remains hidden or buried inside other BH domains and hence they exclusively function as protectors of cell survival. The BCL-2 proteins use BIT domains to interact with each other. The anti-apoptotic BCL-2 proteins interact with pro-apoptotic members and inhibit their function to maintain cellular homeostasis. It is the shift in balance between anti-apoptotic and pro-apoptotic BCL-2 proteins that may decide the fate of cancer cells.

Cancer therapeutics targeting the BCL-2 family mainly have focused on neutralizing one or more anti-apoptotic members by inhibiting their function using small molecule inhibitors or by suppressing their expression utilizing antisense oligonucleotides. The concept was to inhibit the anti-apoptotic BCL-2 members' function and thus allowing proapoptotic members to induce cell death in cancer cells. However, cancer cells treated with Bcl-2 inhibitors were found to upregulate other anti-apoptotic BCL-2 or non-BCL-2 family proteins involved in cell survival, resulting in therapeutic resistance.

There is a need for therapeutic agents that can induce cell death in tumors or cancers with increased expression of BCL-2. This invention is intended to fill this unmet needs associated with current BCL-2 inhibition therapy.

SUMMARY OF THE INVENTION

A first aspect of the invention relates to compounds of Formula (I):

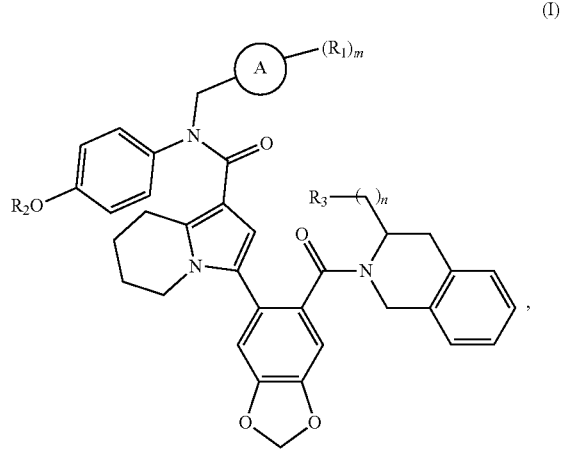

and pharmaceutically acceptable salts, stereoisomers, solvates, prodrugs, or tautomers thereof, wherein:

Ring A is selected from aryl or heteroaryl;

each $R_1$ is independently selected from halo, —OH, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, aryl, —C(O)OR$_4$, and —C(O)NR$_5$R$_6$, wherein aryl is optionally substituted with one or more $R_7$;

$R_2$ is selected from H, $C_1$-$C_6$ alkyl, and —C(O)R$_4$;

$R_3$ is selected from 3- to 8-membered heterocyclyl, —O(CH$_2$O)$_o$R$_8$, and —N(R$_9$)$_2$, wherein the heterocyclyl is optionally substituted with one or more $R_{10}$;

each $R_4$ is independently selected from H and $C_1$-$C_6$ alkyl;

each $R_5$ is independently selected from H, $C_1$-$C_6$ alkyl, —(CH$_2$)$_p$OR$_{11}$, —(CH$_2$)$_p$N(R$_{11}$)$_2$, and S(O)$_2$R$_{11}$;

each $R_6$ is independently selected from H and $C_1$-$C_6$ alkyl, or $R_5$ and $R_6$, together with the atom to which they are attached, come together to form a 3- to 10-membered heterocyclyl ring further comprising 1, 2, or 3 heteroatoms selected from N, O, and S, wherein the heterocyclyl is optionally substituted with one or more $R_{11}$;

each $R_7$ is independently selected from halo, —OH, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, and $C_1$-$C_6$ haloalkoxy;

$R_8$ is selected from H, $C_1$-$C_6$ alkyl, $C_2$-$C_6$ alkenyl, $C_2$-$C_6$ alkynyl, and 3- to 8-membered heterocyclyl, wherein the heterocyclyl is optionally substituted with one or more $R_{10}$;

each $R_9$ is independently selected from H, $C_1$-$C_6$ alkyl, $C_2$-$C_6$ alkenyl, and $C_2$-$C_6$ alkynyl;

each $R_{10}$ is independently selected from $C_1$-$C_6$ alkyl, $C_2$-$C_6$ alkenyl, $C_2$-$C_6$ alkynyl, halo, and —OH;

each $R_{11}$ is independently selected from H and $C_1$-$C_6$ alkyl;

m is an integer selected from 0, 1, 2, 3, 4, and 5; and
n is an integer selected from 0, 1, 2, 3, and 4;
o is an integer selected from 0, 1, and 2; and
p is an integer selected from 0, 1, 2, 3, 4, 5, and 6.

Another aspect of the invention is directed to pharmaceutical compositions comprising a compound of Formula (I), or a pharmaceutically acceptable salt, hydrate, solvate, stereoisomer, or tautomer thereof and a pharmaceutically acceptable carrier. The pharmaceutical acceptable carrier may further include an excipient, diluent, or surfactant.

Another aspect of the invention relates to a method of treating a disease or disorder associated with modulation of BCL-2 proteins, such as Isoform 1 and Isoform 2. The method comprises administering to a patient in need of a treatment for diseases or disorders associated with modulation of BCL-2 proteins an effective amount of a compound of Formula (I), or a pharmaceutically acceptable salt, hydrate, solvate, stereoisomer, tautomer, or pharmaceutical composition thereof.

Another aspect of the invention is directed to a method of inhibiting BCL-2 proteins including, but not limited to Isoform 1 and Isoform 2. The method involves administering to a patient in need thereof an effective amount of a compound of Formula (I), or a pharmaceutically acceptable salt, hydrate, solvate, stereoisomer, tautomer, or pharmaceutical composition thereof.

Another aspect of the invention is directed to a method of treating or preventing a disease or disorder disclosed herein in a subject in need thereof. The method involves administering to a patient in need thereof an effective amount of a compound of Formula (I), or a pharmaceutically acceptable salt, hydrate, solvate, stereoisomer, tautomer, or pharmaceutical composition thereof.

Another aspect of the present invention relates to compounds of Formula (I), and pharmaceutically acceptable salts, hydrates, solvates, prodrugs, stereoisomers, tautomers, or pharmaceutical compositions thereof, for use in the manufacture of a medicament for inhibiting BCL-2 proteins, such as Isoform 1 and Isoform 2.

Another aspect of the present invention relates to compounds of Formula (I), and pharmaceutically acceptable salts, hydrates, solvates, prodrugs, stereoisomers, tautomers, or pharmaceutical compositions thereof, for use in the manufacture of a medicament for treating or preventing a disease or disorder disclosed herein.

Another aspect of the present invention relates to the use of compounds of Formula (I), and pharmaceutically acceptable salts, hydrates, solvates, prodrugs, stereoisomers, tautomers, or pharmaceutical compositions thereof, in the treatment of a disease associated with inhibiting BCL-2 proteins, such as Isoform 1 and Isoform 2.

Another aspect of the present invention relates to the use of compounds of Formula (I), and pharmaceutically acceptable salts, hydrates, solvates, prodrugs, stereoisomers, tautomers, or pharmaceutical compositions thereof, in the treatment of a disease or disorder disclosed herein.

The present invention further provides methods of treating a disease or disorder associated with modulation of BCL-2 proteins including, cancer and metastasis, comprising administering to a patient suffering from at least one of said diseases or disorders a compound of Formula (I), or a pharmaceutically acceptable salt, hydrate, solvate, stereoisomer, tautomer, or pharmaceutical composition thereof.

The present invention provides inhibitors of BCL-2 proteins that are therapeutic agents in the treatment of diseases such as cancer and metastasis.

The present invention further provides compounds and compositions with an improved efficacy and safety profile relative to known BCL-2 protein inhibitors. The present disclosure also provides agents with novel mechanisms of action toward BCL-2 protein in the treatment of various types of diseases including cancer and metastasis.

In some aspects, the present disclosure provides a compound obtainable by, or obtained by, a method for preparing compounds described herein (e.g., a method comprising one or more steps described in General Procedures A-G).

In some aspects, the present disclosure provides an intermediate as described herein, being suitable for use in a method for preparing a compound as described herein (e.g., the intermediate is selected from the intermediates described in Examples 1-45).

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims

DETAILED DESCRIPTION OF THE INVENTION

The present disclosure relates to compounds and compositions that are capable of inhibiting the activity BCL-2 proteins including, but not limited to Isoform 1 and Isoform 2. The disclosure features methods of treating, preventing or ameliorating a disease or disorder in which BCL-2 plays a role by administering to a patient in need thereof a therapeutically effective amount of a compound of Formula (I), or a pharmaceutically acceptable salt, hydrate, solvate, stereoisomer, or tautomer thereof. The methods of the present invention can be used in the treatment of a variety of BCL-2 mediated diseases and disorders by inhibiting the activity of BCL-2 proteins. Inhibition of BCL-2 can be an effective approach to the treatment, prevention, or amelioration of diseases including, but not limited to, cancer and metastasis. Decreasing BCL-2 activity can suppress cancer mutagenesis, dampen tumor evolution, and/or decrease the probability of adverse outcomes, such as drug resistance and/or metastases.

In a first aspect of the invention, the compounds of Formula (I) are described:

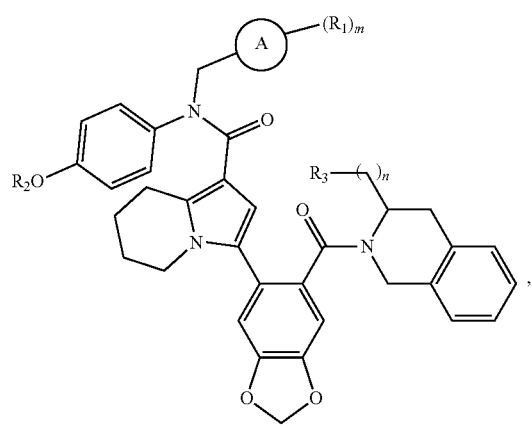

(I)

and pharmaceutically acceptable salts, hydrates, solvates, prodrugs, stereoisomers, and tautomers thereof, wherein Ring A, $R^1$, $R^2$, $R^3$, m, and n are described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and —S(O)N(($C_1$-$C_6$) alkyl)$_2$. The substituents can themselves be optionally substituted. Furthermore, when containing two fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

"Halogen" or "halo" refers to fluorine, chlorine, bromine, or iodine.

"Alkyl" refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above-mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Cycloalkyl" means a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, adamantyl, and derivatives thereof. In the case of polycyclic cycloalkyl, only one of the rings in the cycloalkyl needs to be non-aromatic.

"Heterocyclyl", "heterocycle" or "heterocycloalkyl" refers to a saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms (such as O, N, S, P, Se, or B), e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.0.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, —NH$_2$, —NH(alkyl) or alkylamino, —N(alkyl)$_2$ or dialkylamino, amide-, carbamide-, urea, and sulfamide substituents are included in the term "amino".

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically-labelled compounds of Formula I (e.g., those labeled with $^2$H and $^{14}$C). Deuterated (i.e., $^2$H or D) and carbon-14 (i.e., $^{14}$C) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease or disorder in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting BCL-2 proteins, such as Isoform 1 and Isoform 2, which are useful for the treatment of diseases and disorders associated with modulation of an BCL-2 protein. The invention further relates to compounds, or pharmaceutically acceptable salts, hydrates, solvates, prodrugs, stereoisomers, or tautomers thereof, which can be useful for inhibiting BCL-2.

In some embodiments, the compounds of Formula (I) have the structure of Formula (I'):

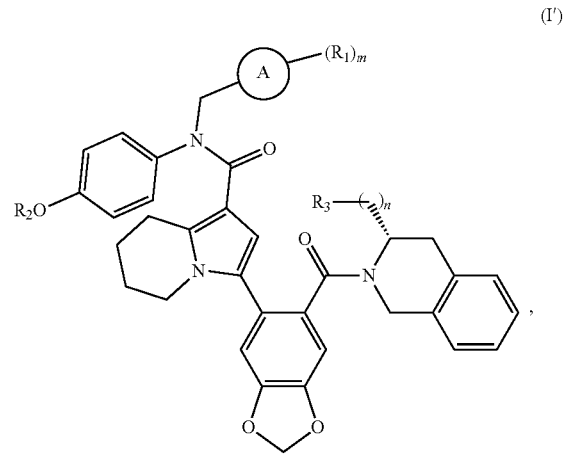

(I')

and pharmaceutically acceptable salts, prodrugs, solvates, hydrates, stereoisomers, or tautomers thereof.

In some embodiments, the compounds of Formula (I) have the structure of Formula (I-A):

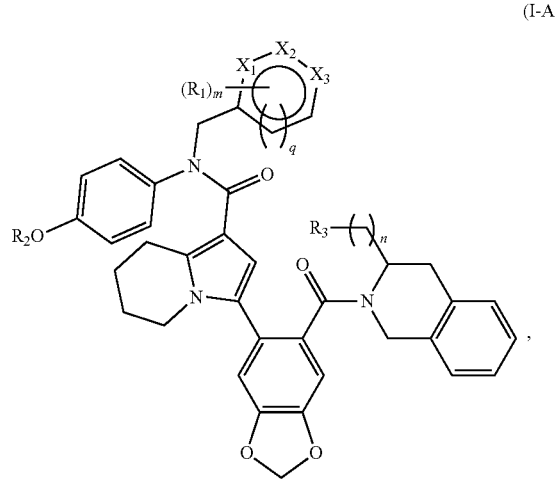

(I-A)

or pharmaceutically acceptable salts, stereoisomers, solvates, prodrugs, or tautomers thereof, wherein:

$X_1$, $X_2$, and $X_3$ are each independently selected from CH, $CR_1$, N, NH, $NR_1$, and O; and q is an integer selected from 0 and 1; and wherein when any one of $X_1$, $X_2$, and $X_3$ is NH, $NR_1$, or O, then q is 0.

In some embodiments, $X_1$ is CH. In some embodiments, $X_1$ is $CR_1$. In some embodiments, $X_1$ is N. In some embodiments, $X_1$ is NH. In some embodiments, $X_1$ is $NR_1$. In some embodiments, $X_1$ is O.

In some embodiments, $X_2$ is CH. In some embodiments, $X_2$ is $CR_1$. In some embodiments, $X_2$ is N. In some embodiments, $X_2$ is NH. In some embodiments, $X_2$ is $NR_1$. In some embodiments, $X_2$ is O.

In some embodiments, $X_3$ is CH. In some embodiments, $X_3$ is $CR_1$. In some embodiments, $X_3$ is N. In some embodiments, $X_3$ is NH. In some embodiments, $X_3$ is $NR_1$. In some embodiments, $X_3$ is O.

In some embodiments, q is 0. In some embodiments, q is 1.

In some embodiments, $X_1$ is O and q is 0. In some embodiments, $X_2$ is O and q is 0. In some embodiments, $X_3$ is O and q is 0.

In some embodiments, $X_1$, $X_2$, and $X_3$ are each independently selected from CH and $CR_1$.

In some embodiments, $X_1$ is N, and $X_2$ and $X_3$ are selected from CH and $CR_1$. In some embodiments, $X_2$ is N, and $X_1$ and $X_3$ are selected from CH and $CR_1$. In some embodiments, $X_3$ is N, and $X_1$ and $X_2$ are selected from CH and $CR_1$.

In some embodiments, $X_1$ is N, $X_2$ is selected from CH and $CR_1$, and $X_3$ is O.

In some embodiments, the compounds of Formula (I) have the structure of Formula (I-B):

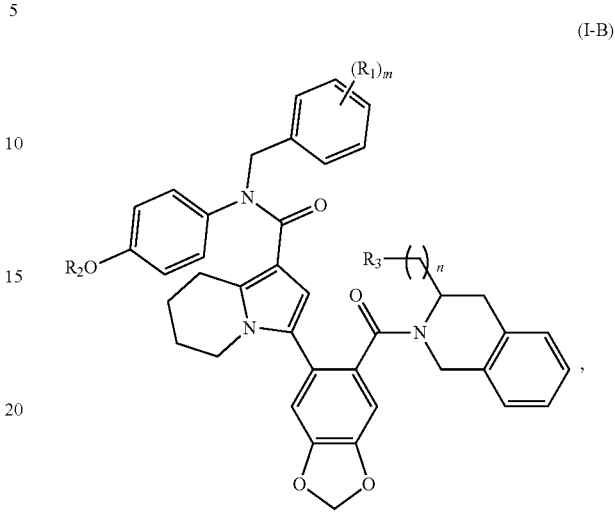

(I-B)

or pharmaceutically acceptable salts, stereoisomers, solvates, prodrugs, or tautomers thereof.

In some embodiments, the compounds of Formula (I) have the structure of Formula (I-B-1):

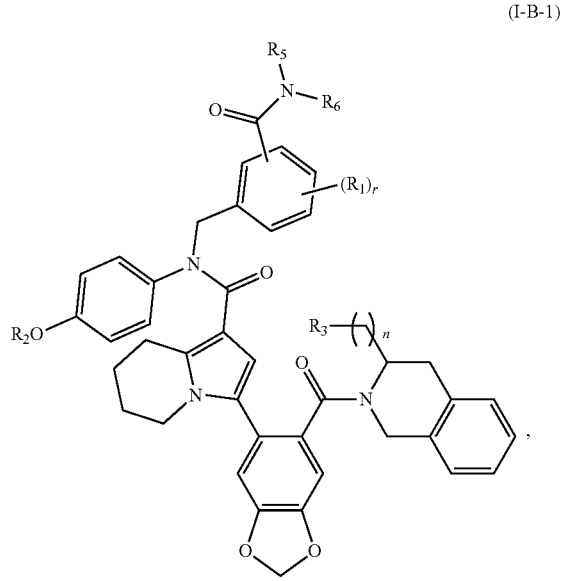

(I-B-1)

or pharmaceutically acceptable salts, stereoisomers, solvates, prodrugs, or tautomers thereof, wherein r is an integer selected from 0, 1, 2, 3, and 4.

In some embodiments, r is 0. In some embodiments, r is 1. In some embodiments, r is 2. In some embodiments, r is 3. In some embodiments, r is 4.

In some embodiments, the compounds of Formula (I) have the structure of Formula (I-C-1), (I-C-2), or (I-C-3):

(I-C-1)

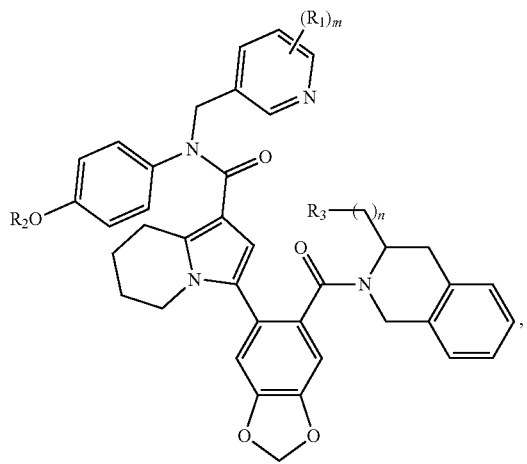

(I-C-2)

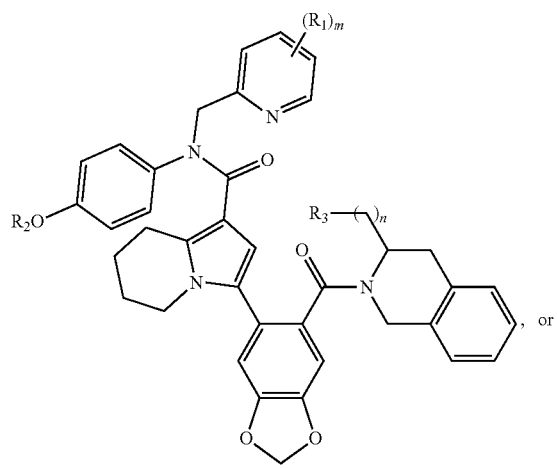, or (I-C-3)

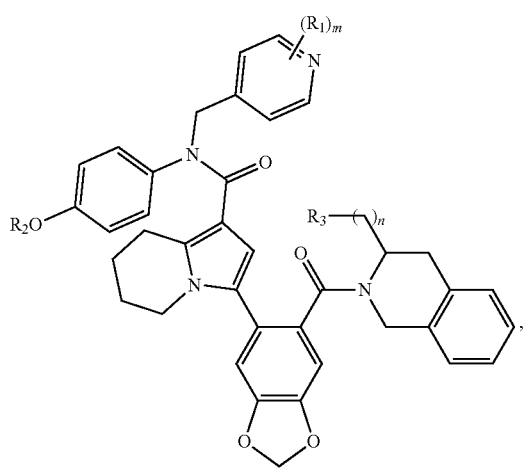

or pharmaceutically acceptable salts, stereoisomers, solvates, prodrugs, or tautomers thereof.

In some embodiments, the compounds of Formula (I) have the structure of Formula (I-D):

(I-D)

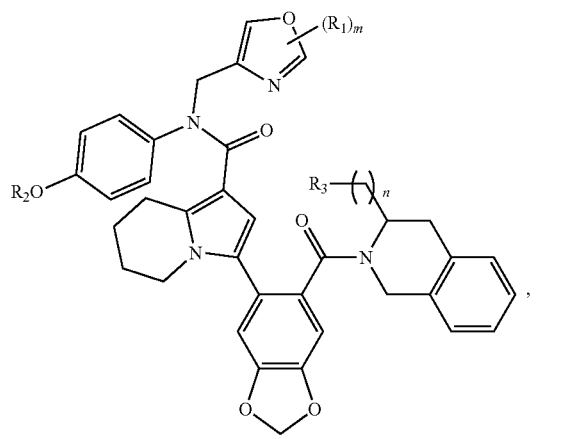

and pharmaceutically acceptable salts, prodrugs, solvates, hydrates, stereoisomers, or tautomers thereof.

In some embodiments, the compounds of Formula (I) have the structure of Formula (I-E):

(I-E)

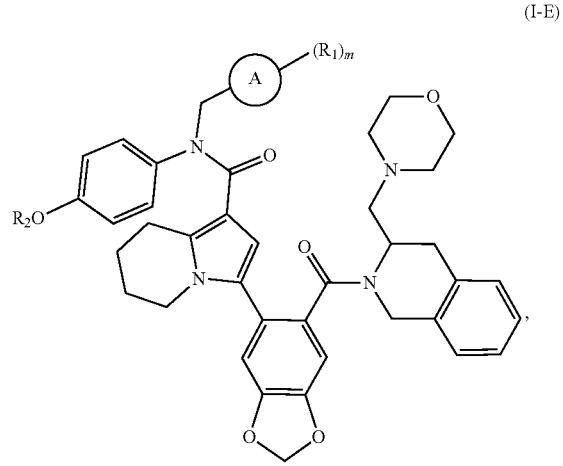

and pharmaceutically acceptable salts, prodrugs, solvates, hydrates, stereoisomers, or tautomers thereof.

In some embodiments, Ring A is aryl. In some embodiments, Ring A is heteroaryl. In some embodiments, Ring A is phenyl. In some embodiments, Ring A is pyridinyl. In some embodiments, Ring A is 5-membered heteroaryl. In some embodiments, Ring A is 5-membered heteroaryl containing at least one N atom. In some embodiments, wherein Ring A is 5-membered heteroaryl containing at least one O atom. In some embodiments, Ring A is oxazolyl.

In some embodiments, Ring A is selected from
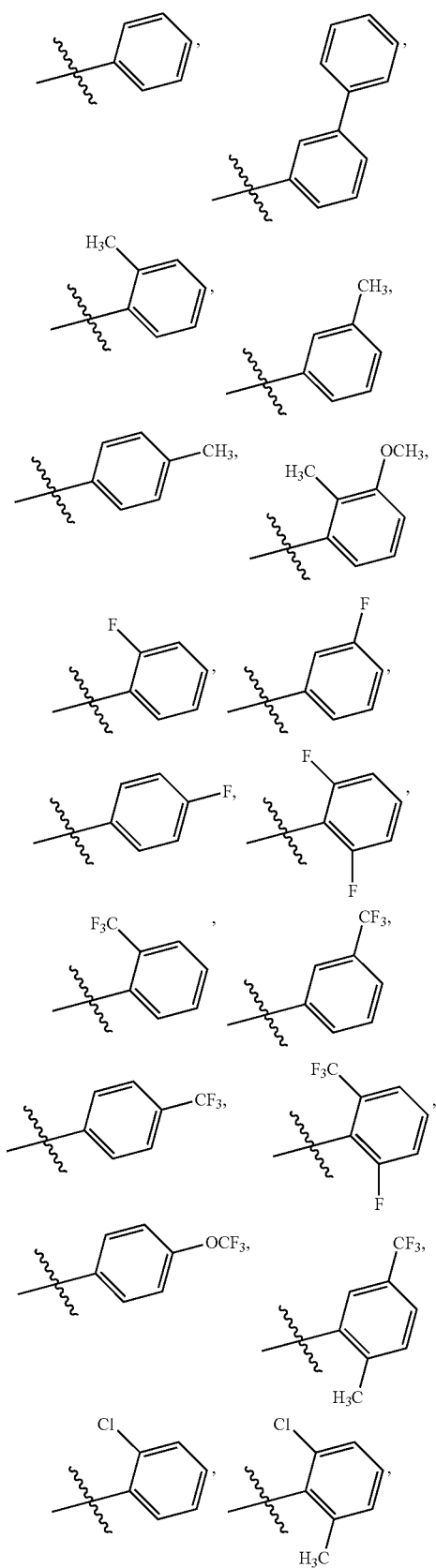
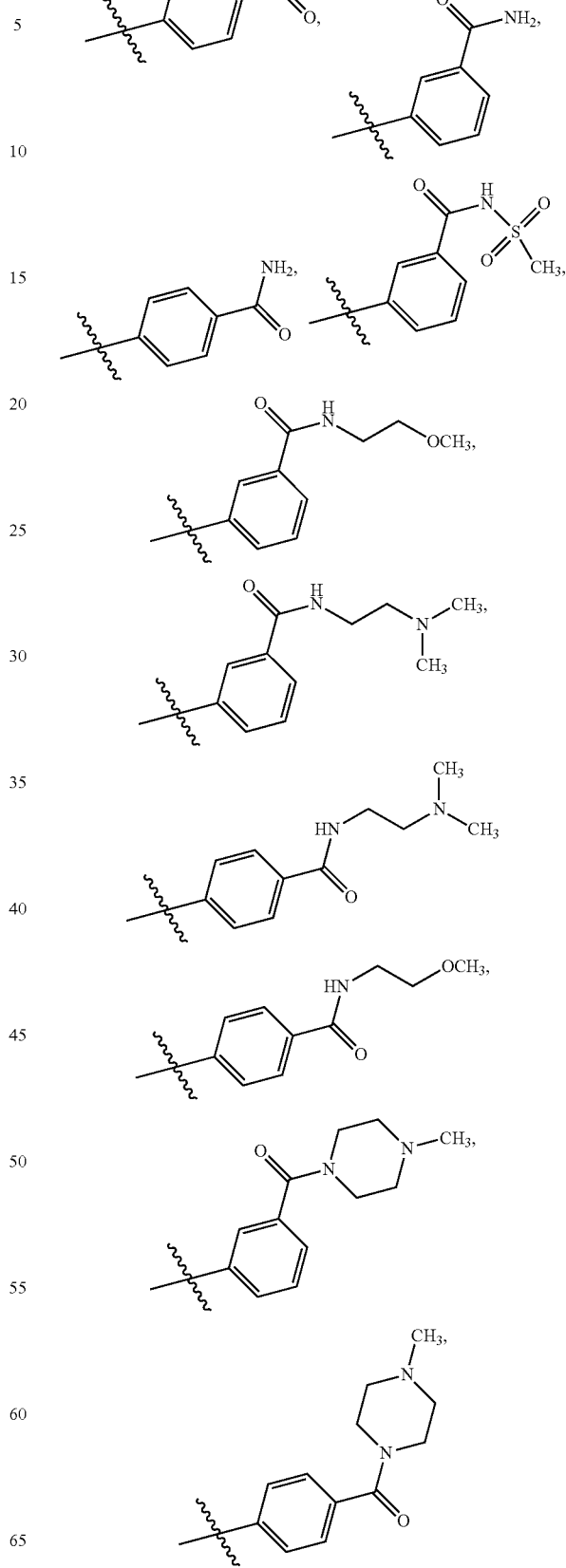

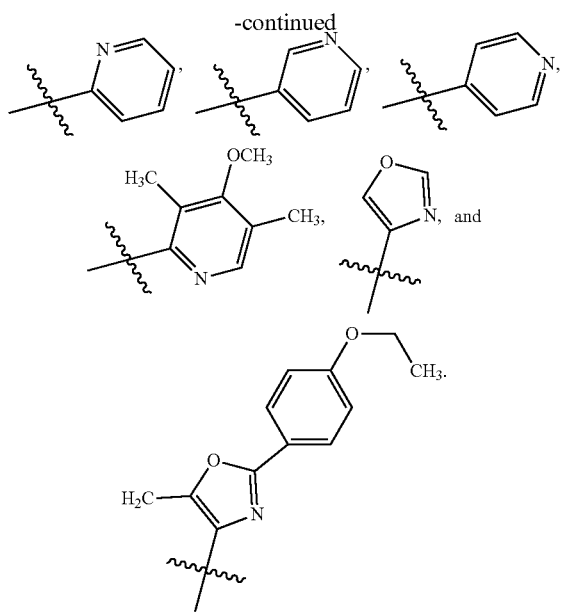

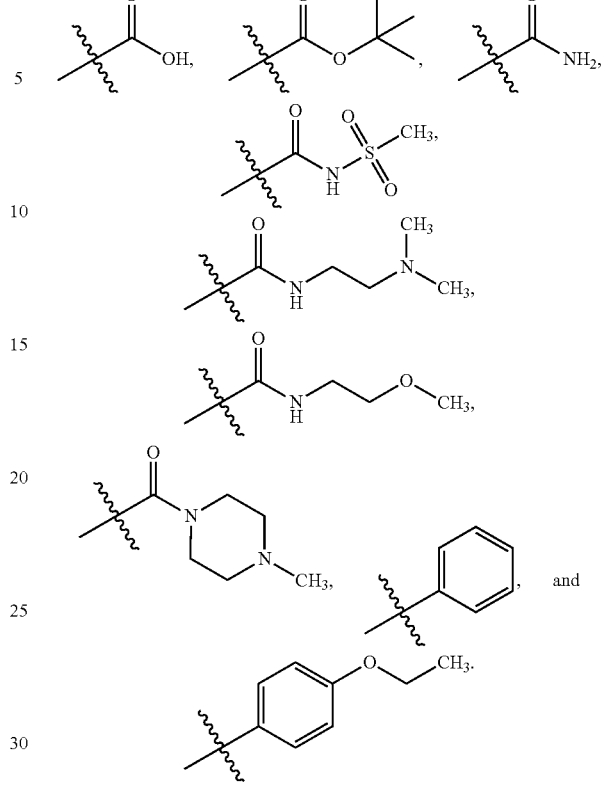

In some embodiments, at least one $R_1$ is halo. In some embodiments, at least one $R_1$ is fluoro. In some embodiments, at least one $R_1$ is chloro. In some embodiments, at least one $R_1$ is bromo. In some embodiments, at least one $R_1$ is iodo. In some embodiments, at least one $R_1$ is —OH. In some embodiments, at least one $R_1$ is —CN. In some embodiments, at least one $R_1$ is —NO$_2$. In some embodiments, at least one $R_1$ is $C_1$-$C_6$ alkyl. In some embodiments, at least one $R_1$ is methyl. In some embodiments, at least one $R_1$ is ethyl. In some embodiments, at least one $R_1$ is propyl. In some embodiments, at least one $R_1$ is butyl. In some embodiments, at least one $R_1$ is pentyl. In some embodiments, at least one $R_1$ is hexyl. In some embodiments, at least one $R_1$ is isopropyl. In some embodiments, at least one $R_1$ is isobutyl. In some embodiments, at least one $R_1$ is tert-butyl. In some embodiments, at least one $R_1$ is $C_2$-$C_6$ alkenyl. In some embodiments, at least one $R_1$ is $C_2$-$C_6$ alkynyl. In some embodiments, at least one $R_1$ is $C_1$-$C_6$ haloalkyl. In some embodiments, at least one $R_1$ is $C_1$-$C_6$ alkoxy. In some embodiments, at least one $R_1$ is methoxy. In some embodiments, at least one $R_1$ is ethoxy. In some embodiments, at least one $R_1$ is $C_1$-$C_6$ haloalkoxy. In some embodiments, at least one $R_1$ is trifluoromethoxy. In some embodiments, at least one $R_1$ is aryl. In some embodiments, at least one $R_1$ is aryl optionally substituted with one or more $R_7$. In some embodiments, at least one $R_1$ is phenyl. In some embodiments, at least one $R_1$ is phenyl optionally substituted with one or more $R_7$. In some embodiments, at least one $R_1$ is —C(O)NR$_5$R$_6$, wherein $R_5$ and $R_6$, together with the atom to which they are attached, come together to form a 3- to 10-membered heterocyclyl ring further comprising 1, 2, or 3 heteroatoms selected from N, O, and S. In some embodiments, at least one $R_1$ is —C(O)NR$_5$R$_6$, wherein $R_5$ and $R_6$, together with the atom to which they are attached, come together to form a 3- to 10-membered heterocyclyl ring further comprising 1, 2, or 3 heteroatoms selected from N, O, and S, wherein the heterocyclyl is optionally substituted with one or more $R_{11}$.

In some embodiments, at least one $R_1$ is selected from —F, —CH$_3$, —OCH$_3$, —OCH$_2$CH$_3$, —CF$_3$, —OCF$_3$, In some embodiments, $R_2$ is H. In some embodiments, $R_2$ is $C_1$-$C_6$ alkyl. In some embodiments, $R_2$ is methyl. In some embodiments, $R_2$ is ethyl. In some embodiments, $R_2$ is propyl. In some embodiments, $R_2$ is butyl. In some embodiments, $R_2$ is pentyl. In some embodiments, $R_2$ is hexyl. In some embodiments, $R_2$ is tert-butyl. In some embodiments, $R_2$ is —C(O)R$_4$.

In some embodiments, $R_2$ is —C(O)R$_4$ and $R_4$ is methyl.

In some embodiments, m is 0. In some embodiments, m is 1. In some embodiments, m is 2. In some embodiments, m is 3. In some embodiments, m is 4. In some embodiments, m is 5. In some embodiments, m is 1, 2, or 3. In some embodiments, m is 2 or 3.

In some embodiments, m is 2 or 3 and at least one $R_1$ is $C_1$-$C_6$ alkyl.

In some embodiments, m is 2 and at least one $R_1$ is halo.

In some embodiments, $R_3$ is 3- to 8-membered heterocyclyl. In some embodiments, $R_3$ is 3- to 8-membered heterocyclyl substituted with one or more $R_{10}$. In some embodiments, $R_3$ is —O(CH$_2$O)$_o$R$_8$. In some embodiments, $R_3$ is —N(R$_9$)$_2$. In some embodiments, $R_3$ is 6-membered heterocyclyl. In some embodiments, $R_3$ is 6-membered heterocyclyl substituted with one or more $R_{10}$. In some embodiments, $R_3$ is 6-membered heterocyclyl comprising at least one N atom. In some embodiments, $R_3$ is 6-membered heterocyclyl comprising at least one N atom substituted with one or more $R_{10}$. In some embodiments, $R_3$ is 6-membered heterocyclyl comprising at least two N atoms. In some embodiments, $R_3$ is 6-membered heterocyclyl comprising at least two N atoms substituted with one or more $R_{10}$. In some embodiments, $R_3$ is 6-membered heterocyclyl comprising at least one O atom. In some embodiments, $R_3$ is 6-membered heterocyclyl comprising at least one O atom substituted with one or more $R_{10}$. In some embodiments, $R_3$ is 6-membered heterocyclyl comprising at least one N atom and at least one O atom. In some embodiments, $R_3$ is 6-membered heterocyclyl comprising at least one N atom and at least one O atom substituted with one or more $R_{10}$. In some embodiments, $R_3$ is 7-membered heterocyclyl. In some embodiments, $R_3$ is 7-membered heterocyclyl substituted with one or more $R_{10}$. In some embodiments, $R_3$ is 7-membered heterocyclyl comprising at least one N atom. In some embodiments, $R_3$ is 7-membered heterocyclyl comprising at least one N atom substituted with one or more $R_{10}$.

In some embodiments, $R_3$ is selected from

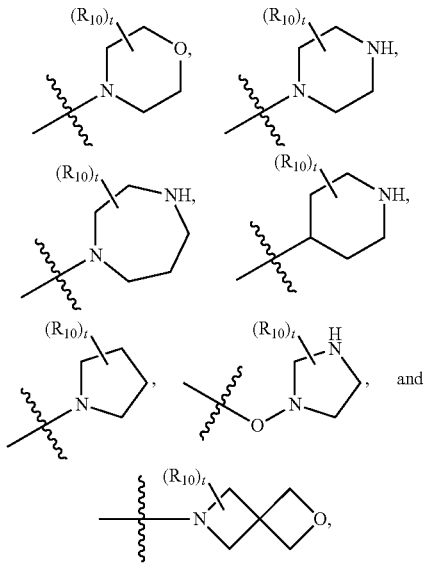

wherein t is 0, 1, 2, 3, or 4.

In some embodiments, $R_3$ is selected from

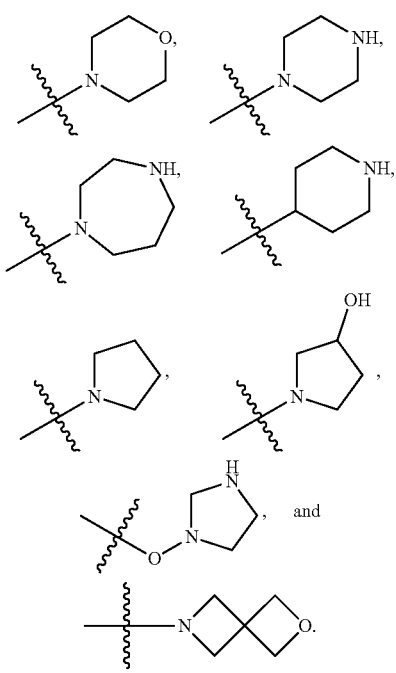

In some embodiments, $R_3$ is

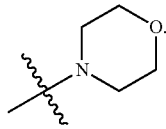

In some embodiments, at least one $R_4$ is H. In some embodiments, at least one $R_4$ is $C_1$-$C_6$ alkyl. In some embodiments, at least one $R_4$ is methyl. In some embodiments, at least one $R_4$ is ethyl. In some embodiments, at least one $R_4$ is propyl. In some embodiments, at least one $R_4$ is butyl. In some embodiments, at least one $R_4$ is pentyl. In some embodiments, at least one $R_4$ is hexyl. In some embodiments, at least one $R_4$ is isopropyl. In some embodiments, at least one $R_4$ is isobutyl. In some embodiments, at least one $R_4$ is tert-butyl.

In some embodiments, at least one $R_5$ is H. In some embodiments, at least one $R_5$ is $C_1$-$C_6$ alkyl. In some embodiments, at least one $R_5$ is methyl. In some embodiments, at least one $R_5$ is ethyl. In some embodiments, at least one $R_5$ is propyl. In some embodiments, at least one $R_5$ is butyl. In some embodiments, at least one $R_5$ is pentyl. In some embodiments, at least one $R_5$ is hexyl. In some embodiments, at least one $R_5$ is isopropyl. In some embodiments, at least one $R_5$ is isobutyl. In some embodiments, at least one $R_5$ is tert-butyl. In some embodiments, at least one $R_5$ is $-(CH_2)_pOR_{11}$. In some embodiments, at least one $R_5$ is $-(CH_2)_pN(R_{11})_2$. In some embodiments, at least one $R_5$ is $-S(O)_2R_{11}$.

In some embodiments, at least one $R_6$ is H. In some embodiments, at least one $R_6$ is $C_1$-$C_6$ alkyl. In some embodiments, at least one $R_6$ is methyl. In some embodiments, at least one $R_6$ is ethyl. In some embodiments, at least one $R_6$ is propyl. In some embodiments, at least one $R_6$ is butyl. In some embodiments, at least one $R_6$ is pentyl. In some embodiments, at least one $R_6$ is hexyl. In some embodiments, at least one $R_6$ is isopropyl. In some embodiments, at least one $R_6$ is isobutyl.

In some embodiments, at least one $R_5$ is H and at least one $R_6$ is H.

In some embodiments, at least one $R_5$ is H and at least one $R_6$ is $-(CH_2)_pOR_{11}$.

In some embodiments, at least one $R_5$ is H and at least one $R_6$ is $-(CH_2)_pN(R_6)_{11}$.

In some embodiments, at least one $R_5$ and at least one $R_6$, together with the atom to which they are attached, come together to form a 3- to 10-membered heterocyclyl ring further comprising 1, 2, or 3 heteroatoms selected from N, O, and S, In some embodiments, at least one $R_5$ and at least one $R_6$, together with the atom to which they are attached, come together to form a 3- to 10-membered heterocyclyl ring further comprising 1, 2, or 3 heteroatoms selected from N, O, and S, wherein the heterocyclyl is substituted with one or more $R_{11}$.

In some embodiments, at least one $R_7$ is halo. In some embodiments, at least one $R_7$ is fluoro. In some embodiments, at least one $R_7$ is chloro. In some embodiments, at least one $R_7$ is bromo. In some embodiments, at least one $R_7$ is iodo. In some embodiments, at least one $R_7$ is $-OH$. In some embodiments, at least one $R_7$ is $-CN$. In some embodiments, at least one $R_7$ is $C_1$-$C_6$ alkyl. In some embodiments, at least one $R_7$ is methyl. In some embodiments, at least one $R_7$ is ethyl. In some embodiments, at least one $R_7$ is propyl. In some embodiments, at least one $R_7$ is butyl. In some embodiments, at least one $R_7$ is pentyl. In some embodiments, at least one $R_7$ is hexyl. In some embodiments, at least one $R_7$ is isopropyl. In some embodiments, at least one $R_7$ is isobutyl. In some embodiments, at least one $R_7$ is tert-butyl. In some embodiments, at least one $R_7$ is $C_2$-$C_6$ alkenyl. In some embodiments, at least one $R_7$ is $C_2$-$C_6$ alkynyl. In some embodiments, at least one $R_7$ is $C_1$-$C_6$ haloalkyl. In some embodiments, at least one $R_7$ is $C_1$-$C_6$ alkoxy. In some embodiments, at least one $R_7$ is ethoxy. In some embodiments, at least one $R_7$ is $C_1$-$C_6$ haloalkoxy.

In some embodiments, at least one $R_8$ is $C_1$-$C_6$ alkyl. In some embodiments, at least one $R_8$ is methyl. In some embodiments, at least one $R_8$ is ethyl. In some embodiments, at least one $R_8$ is propyl. In some embodiments, at least one $R_8$ is butyl. In some embodiments, at least one $R_8$ is pentyl. In some embodiments, at least one $R_8$ is hexyl. In some embodiments, at least one $R_8$ is isopropyl. In some embodiments, at least one $R_8$ is isobutyl. In some embodiments, at least one $R_8$ is tert-butyl. In some embodiments, at least one $R_8$ is $C_2$-$C_6$ alkenyl. In some embodiments, at least one $R_8$ is $C_2$-$C_6$ alkynyl. In some embodiments, at least one $R_8$ is 3- to 8-membered heterocyclyl. In some embodiments, at least one $R_8$ is 3- to 8-membered heterocyclyl substituted with one or more $R_{10}$.

In some embodiments, at least one $R_9$ is H. In some embodiments, at least one $R_9$ is $C_1$-$C_6$ alkyl. In some embodiments, at least one $R_9$ is methyl. In some embodiments, at least one $R_9$ is ethyl. In some embodiments, at least one $R_9$ is propyl. In some embodiments, at least one $R_9$ is butyl. In some embodiments, at least one $R_9$ is pentyl. In some embodiments, at least one $R_9$ is hexyl. In some embodiments, at least one $R_9$ is isopropyl. In some embodiments, at least one $R_9$ is isobutyl. In some embodiments, at least one $R_9$ is tert-butyl. In some embodiments, at least one $R_9$ is $C_2$-$C_6$ alkenyl. In some embodiments, at least one $R_9$ is $C_2$-$C_6$ alkynyl.

In some embodiments, at least one $R_{10}$ is halo. In some embodiments, at least one $R_{10}$ is fluoro. In some embodiments, at least one $R_{10}$ is chloro. In some embodiments, at least one $R_{10}$ is bromo. In some embodiments, at least one $R_{10}$ is iodo. In some embodiments, at least one $R_{10}$ is —OH. In some embodiments, at least one $R_{10}$ is $C_1$-$C_6$ alkyl. In some embodiments, at least one $R_{10}$ is methyl. In some embodiments, at least one $R_{10}$ is ethyl. In some embodiments, at least one $R_{10}$ is propyl. In some embodiments, at least one $R_{10}$ is butyl. In some embodiments, at least one $R_{10}$ is pentyl. In some embodiments, at least one $R_{10}$ is hexyl. In some embodiments, at least one $R_{10}$ is isopropyl. In some embodiments, at least one $R_{10}$ is isobutyl. In some embodiments, at least one $R_{10}$ is tert-butyl. In some embodiments, at least one $R_{10}$ is $C_2$-$C_6$ alkenyl. In some embodiments, at least one $R_{10}$ is $C_2$-$C_6$ alkynyl.

In some embodiments, at least one $R_{11}$ is H. In some embodiments, at least one $R_{11}$ is $C_1$-$C_6$ alkyl. In some embodiments, at least one $R_{11}$ is methyl. In some embodiments, at least one $R_{11}$ is ethyl. In some embodiments, at least one $R_{11}$ is propyl. In some embodiments, at least one $R_{11}$ is butyl. In some embodiments, at least one $R_{11}$ is pentyl. In some embodiments, at least one $R_{11}$ is hexyl. In some embodiments, at least one $R_{11}$ is isopropyl. In some embodiments, at least one $R_{11}$ is isobutyl. In some embodiments, at least one $R_{11}$ is tert-butyl.

In some embodiments, n is 0. In some embodiments, n is 1. In some embodiments, n is 2. In some embodiments, n is 3. In some embodiments, n is 4.

In some embodiments, o is 0. In some embodiments, o is 1. In some embodiments, o is 2.

In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, Ring A is aryl, $R_1$ is aryl, $R_2$ is H, $R_3$ is 3- to 8-membered heterocyclyl, m is 1, and n is 1.

In some embodiments, Ring A is aryl, $R_1$ is $C_1$-$C_6$ haloalkyl, $R_2$ is H, $R_3$ is 3- to 8-membered heterocyclyl, m is 1, and n is 1.

In some embodiments, Ring A is aryl, $R_1$ is $C_1$-$C_6$ alkoxy, $R_2$ is H, $R_3$ is 3- to 8-membered heterocyclyl, m is 1, and n is 1.

Non-limiting illustrative compounds of the present disclosure include:

(S)—N-(4-hydroxyphenyl)-N-(4-((2-methoxyethyl)carbamoyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(3-((2-methoxyethyl)carbamoyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(3-methoxy-2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(2-(trifluoromethyl)benzyl)-5,6,7,8-tetrahydroindolizine-1-carboxamide;

(S)—N-(3-((2-(dimethylamino)ethyl)carbamoyl)benzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(3-carbamoylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-((2-(dimethylamino)ethyl)carbamoyl)benzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(pyridin-4-ylmethyl)-5,6,7,8-tetrahydroindolizine-1-carboxamide;

(S)—N-(4-hydroxyphenyl)-N-(3-(4-methylpiperazine-1-carbonyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(2-fluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(4-(4-methylpiperazine-1-carbonyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-carbamoylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(3-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-benzyl-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(3-(trifluoromethyl)benzyl)-5,6,7,8-tetrahydroindolizine-1-carboxamide;

(S)—N-(4-fluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-([1,1'-biphenyl]-3-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(2,6-difluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(4-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(3-fluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(2-fluoro-6-(trifluoromethyl)benzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-((4-methoxy-3,5-dimethylpyridin-2-yl)methyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(4-(trifluoromethyl)benzyl)-5,6,7,8-tetrahydroindolizine-1-carboxamide;

(S)-4-((N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)methyl)benzoic acid;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(4-(trifluoromethoxy)benzyl)-5,6,7,8-tetrahydroindolizine-1-carboxamide;

(S)—N-((2-(4-ethoxyphenyl)-5-(l3-methyl)oxazol-4-yl)methyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)-3-((N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)methyl)benzoic acid;

tert-butyl (S)-3-((N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)methyl)benzoate;

(S)—N-(2,6-dimethylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(2-methoxybenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(2-fluoro-6-methylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(2-chlorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(2-chloro-6-methylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(6-chloro-2,3-difluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-([1,1'-biphenyl]-2-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(2-methyl-4-(trifluoromethyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(2-methyl-5-(trifluoromethyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(pyridin-3-ylmethyl)-5,6,7,8-tetrahydroindolizine-1-carboxamide;

(S)—N-((2-(4-ethoxyphenyl)-5-methyloxazol-4-yl)methyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)-4-(N-(3-carbamoylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)phenyl acetate;

(S)—N-(3-carbamoylbenzyl)-N-(4-ethoxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; and (S)—N-(4-hydroxyphenyl)-N-(3-((methylsulfonyl)carbamoyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

4-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic acid;

3-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic acid;

tert-Butyl 3-[(4-hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoate;

N-[(2-Cyanophenyl)methyl]-N-(4-hydroxyphenyl)-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide;

N-(4-Hydroxyphenyl)-N-[(4-methyl-1,2,4-triazol-3-yl)methyl]-3-[6-[(3 S)-3-(morpholinomethyl)-3,4-dihydro-1H-isoquinoline-2-carbonyl]-1,3-benzodioxol-5-yl]-5,6,7,8-tetrahydroindolizine-1-carboxamide;

N-(4-Hydroxyphenyl)-3-[6-[(3S)-3-(morpholinomethyl)-3,4-dihydro-1H-isoquinoline-2-carbonyl]-1,3-benzodioxol-5-yl]-N-[(3-nitrophenyl)methyl]-5,6,7,8-tetrahydroindolizine-1-carboxamide;

N-(4-Hydroxyphenyl)-N-[(2-methyl-3-nitro-phenyl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide;

and pharmaceutically acceptable salts, stereoisomers, solvates, prodrugs, or tautomers thereof.

In some embodiments, the compound of Formula (I) is selected from:

(S)—N-(4-hydroxyphenyl)-N-(3-methoxy-2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(2-(trifluoromethyl)benzyl)-5,6,7,8-tetrahydroindolizine-1-carboxamide;

(S)—N-([1,1'-biphenyl]-3-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-(4-hydroxyphenyl)-N-(2-methoxybenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

(S)—N-([1,1'-biphenyl]-2-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide;

4-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic acid;

3-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic acid;

tert-Butyl 3[(4-hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoate;

N-[(2-Cyanophenyl)methyl]-N-(4-hydroxyphenyl)-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide;

N-(4-Hydroxyphenyl)-N-[(4-methyl-1,2,4-triazol-3-yl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide;

N-(4-Hydroxyphenyl)-3-[6-[(3S)-3-(morpholinomethyl)-3,4-dihydro-1H-isoquinoline-2-carbonyl]-1,3-benzodioxol-5-yl]-N-[(3-nitrophenyl)methyl]-5,6,7,8-tetrahydroindolizine-1-carboxamide;

N-(4-Hydroxyphenyl)-N-[(2-methyl-3-nitro-phenyl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide;

or a pharmaceutically acceptable salt, stereoisomer, solvate, or tautomer thereof.

In some embodiments, the compound of Formula (I) is (S)—N-(4-hydroxyphenyl)-N-(3-methoxy-2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide, or a pharmaceutically acceptable salt, stereoisomer, solvate, or tautomer thereof.

In some embodiments, the compound of Formula (I) is (S)—N-(4-hydroxyphenyl)-3-(6-(3-(morpholinomethyl)-1,2,3,4-tetrahydroisoquinoline-2-carbonyl)benzo[d][1,3]dioxol-5-yl)-N-(2-(trifluoromethyl)benzyl)-5,6,7,8-tetrahydroindolizine-1-carboxamide, or a pharmaceutically acceptable salt, stereoisomer, solvate, or tautomer thereof.

In some embodiments, the compound of Formula (I) is (S)—N-([1,1'-biphenyl]-3-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide, or a pharmaceutically acceptable salt, stereoisomer, solvate, or tautomer thereof.

In some embodiments, the compound of Formula (I) is (S)—N-(4-hydroxyphenyl)-N-(2-methoxybenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide, or a pharmaceutically acceptable salt, stereoisomer, solvate, or tautomer thereof.

In some embodiments, the compound of Formula (I) is (S)—N-([1,1'-biphenyl]-2-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide, or a pharmaceutically acceptable salt, stereoisomer, solvate, or tautomer thereof.

In some embodiments, the compound is a pharmaceutically acceptable salt. In some embodiments, the compound is a hydrochloride salt.

It should be understood that all stereoisomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional stereoisomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of BCL-2 proteins. In one embodiment, the compounds of the present invention are inhibitors of BCL-2 proteins. In another embodiment, the BCL-2 proteins is Isoform 1. In another embodiment, the BCL-2 proteins is Isoform 2.

In some embodiments, the compounds of Formula I are selective inhibitors of BCL-2 proteins.

In some embodiments, the compounds of Formula I are dual inhibitors of BCL-2/BCL-xL proteins.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Procedures A-G which comprise different sequences of assembling intermediates or compounds. Starting materials are either commercially available or made by known procedures in the reported literature or as illustrated below.

General Procedure A

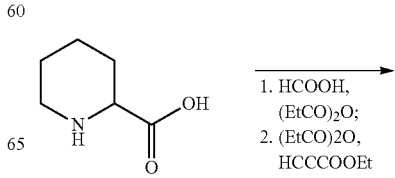

1. HCOOH, (EtCO)$_2$O;
2. (EtCO)2O, HCCCOOEt

-continued
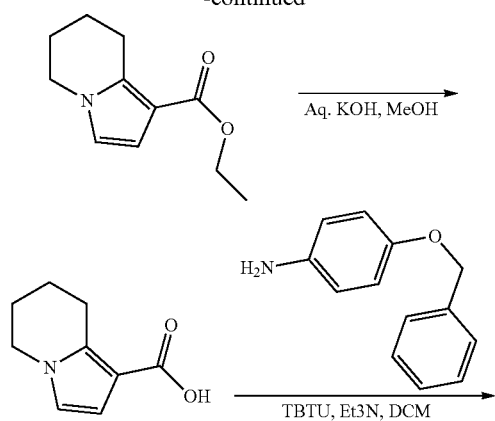
General Procedure B
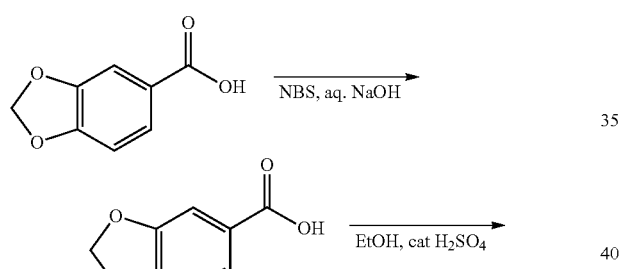
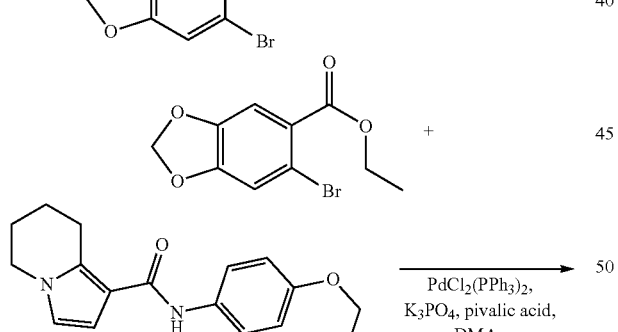
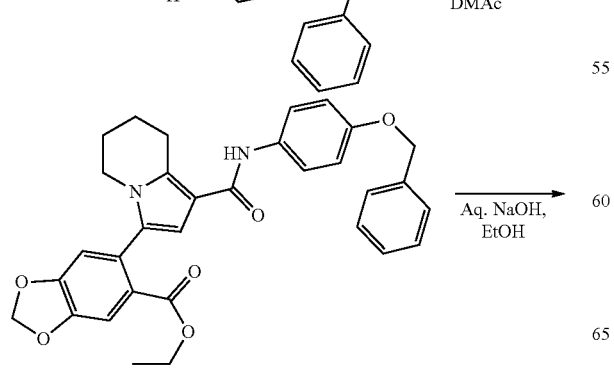
-continued
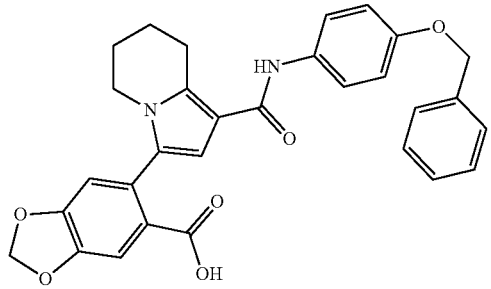
General Procedure C
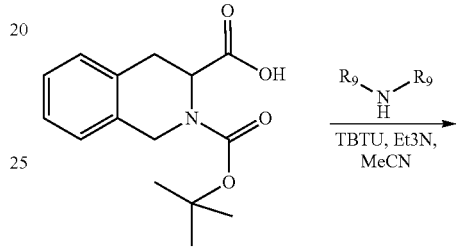
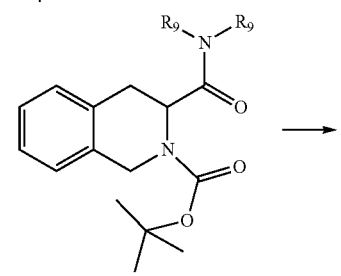
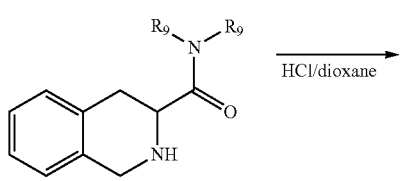
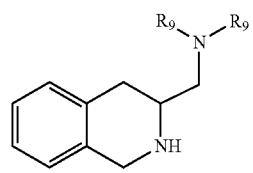

General Procedure D
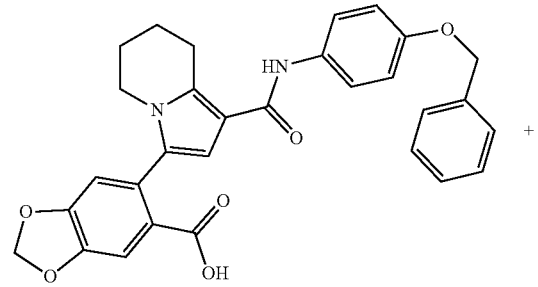
+
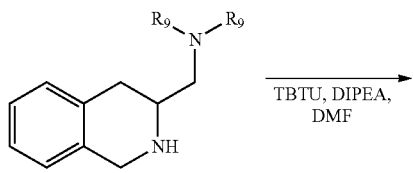 →(TBTU, DIPEA, DMF)
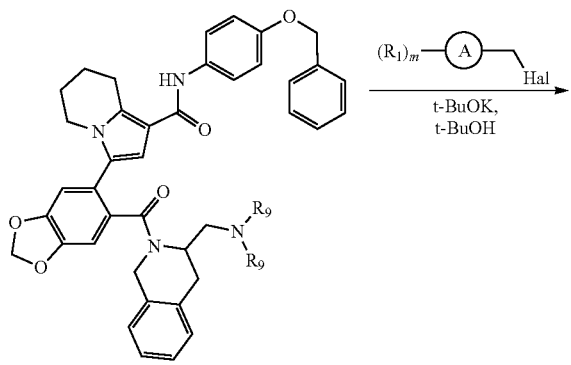 →(R₁)ₘ—A—CH₂—Hal, t-BuOK, t-BuOH
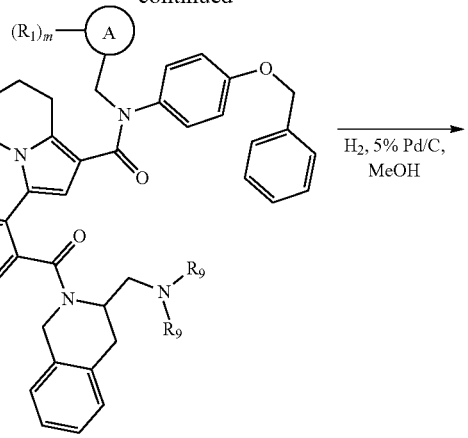 →(H₂, 5% Pd/C, MeOH)
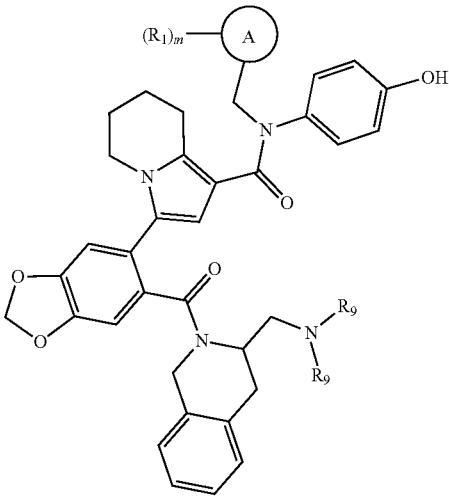
General Procedure E
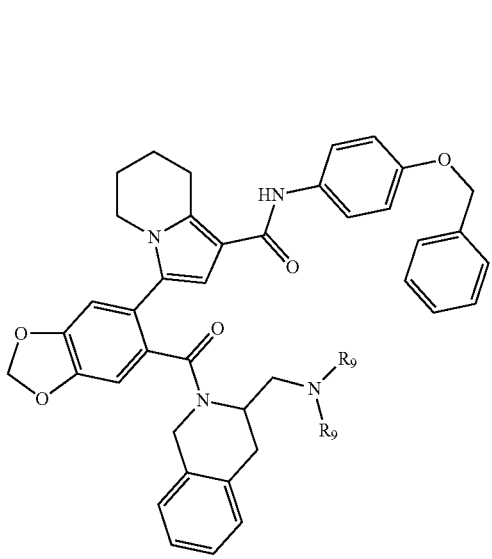 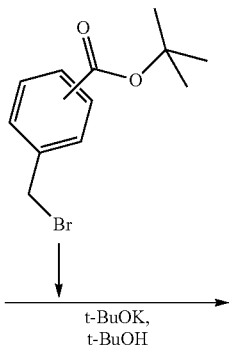 →(t-BuOK, t-BuOH)

-continued
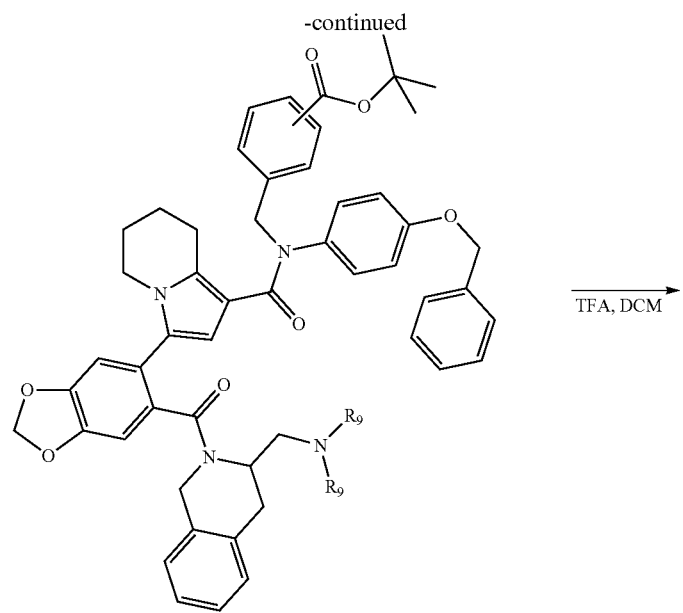
TFA, DCM →
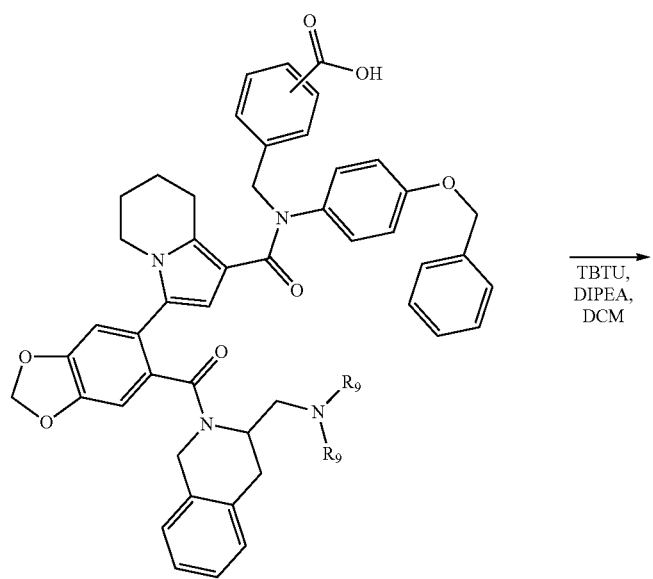
TBTU, DIPEA, DCM →

35
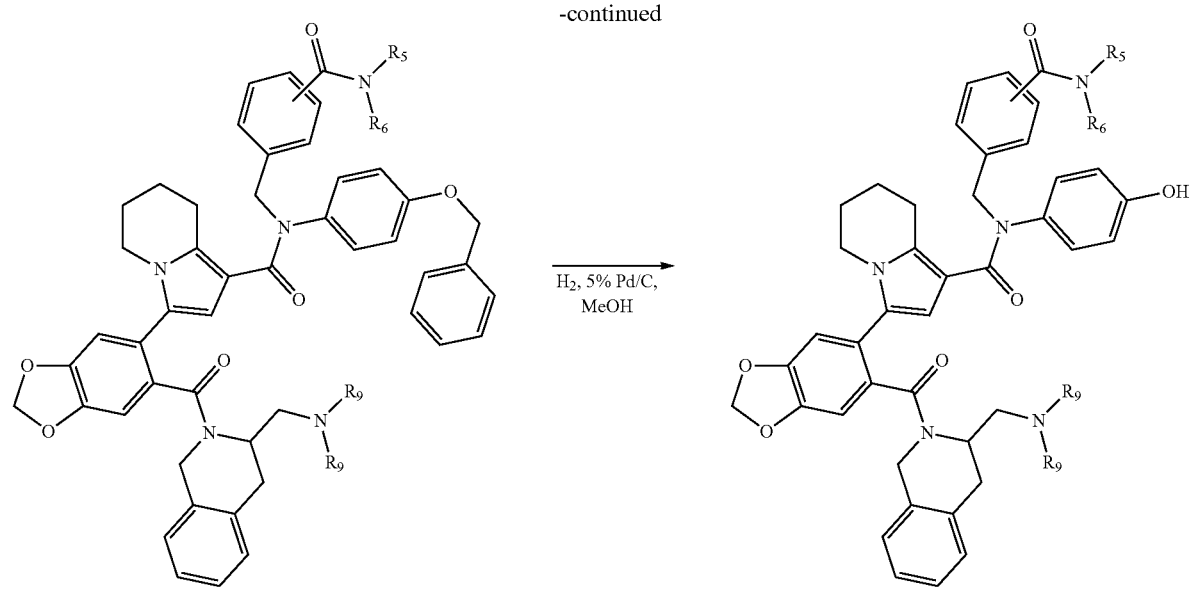
-continued
36
H₂, 5% Pd/C, MeOH
General Procedure F
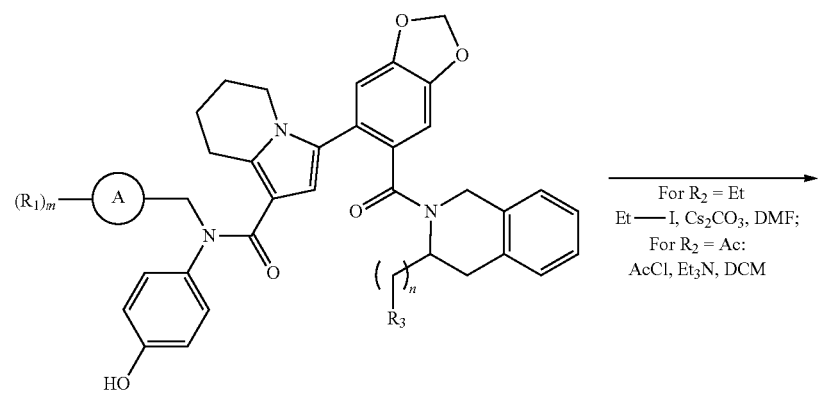
For R₂ = Et
Et—I, Cs₂CO₃, DMF;
For R₂ = Ac:
AcCl, Et₃N, DCM
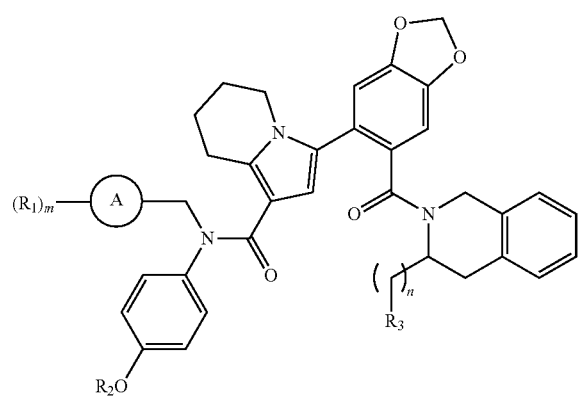

General Procedure G

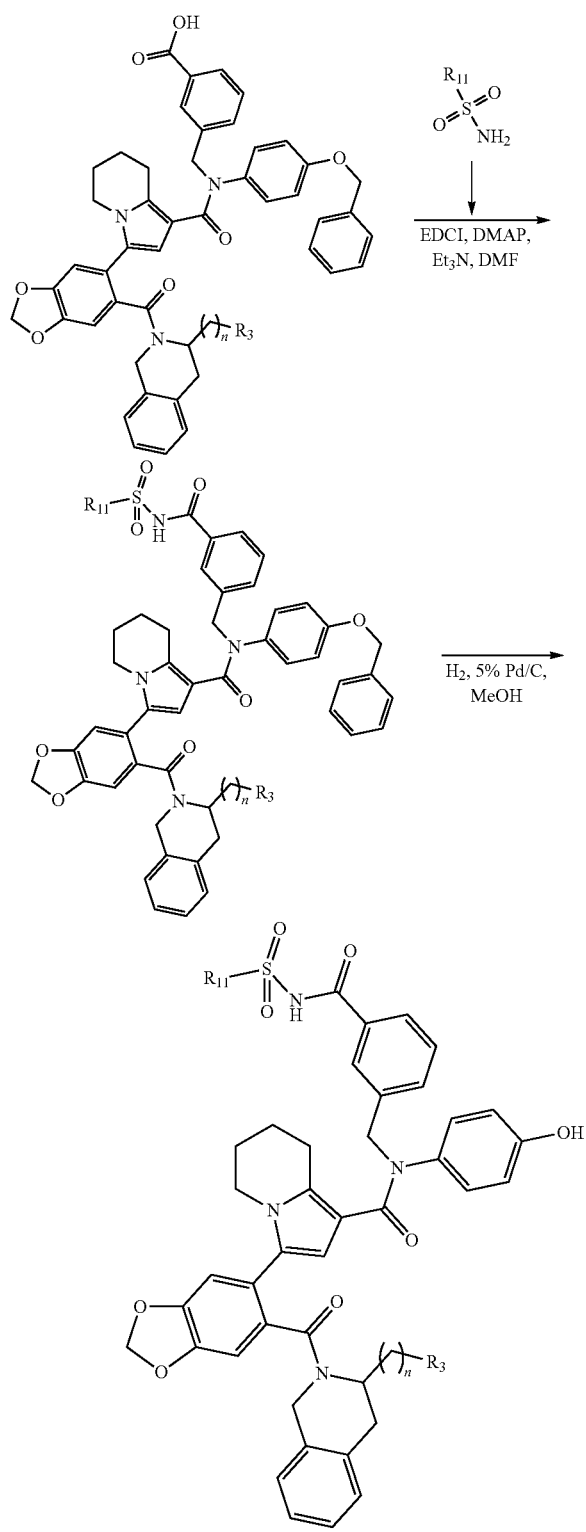

Methods of Using the Disclosed Compounds

Another aspect of the invention relates to a method of treating a disease or disorder associated with modulation of BCL-2 proteins. The method comprises administering to a patient in need of a treatment for diseases or disorders associated with modulation of BCL-2 proteins an effective amount the compositions and compounds of Formula (I).

In another aspect, the present invention is directed to a method of inhibiting BCL-2 proteins. The method involves administering to a patient in need thereof an effective amount of a compound of Formula (I).

Another aspect of the present invention relates to a method of treating, preventing, inhibiting or eliminating a disease or disorder in a patient associated with the inhibition of BCL-2 proteins, the method comprising administering to a patient in need thereof an effective amount of a compound of Formula (I). In one embodiment, the disease may be, but not limited to, cancer and metastasis.

The present invention also relates to the use of an inhibitor of BCL-2 proteins for the preparation of a medicament used in the treatment, prevention, inhibition or elimination of a disease or condition mediated by BCL-2 proteins, wherein the medicament comprises a compound of Formula (I).

In another aspect, the present invention relates to a method for the manufacture of a medicament for treating, preventing, inhibiting, or eliminating a disease or condition mediated by BCL-2 proteins, wherein the medicament comprises a compound of Formula (I).

Another aspect of the present invention relates to a compound of Formula (I) for use in the manufacture of a medicament for treating a disease associated with inhibiting BCL-2 proteins.

In another aspect, the present invention relates to the use of a compound of Formula (I) in the treatment of a disease associated with inhibiting BCL-2 proteins.

Another aspect of the invention relates to a method of treating cancer. The method comprises administering to a patient in need thereof an effective amount of a compound of Formula (I).

Another aspect of the invention relates to a method of treating or preventing cancer. The method comprises administering to a patient in need thereof an effective amount of a compound of Formula (I).

In one embodiment, the present invention relates to the use of an inhibitor of BCL-2 proteins for the preparation of a medicament used in treatment, prevention, inhibition or elimination of a disease or disorder associated with cancer.

In another embodiment, the present invention relates to a compound of Formula (I) or a pharmaceutical composition comprising a compound of the present invention and a pharmaceutically acceptable carrier used for the treatment of cancers including, but not limited to, selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL), and chronic lymphocytic leukemia/small lymphocytic lymphoma (CLL/SLL).

In another embodiment, the present invention relates to a compound of Formula (I) or a pharmaceutical composition comprising a compound of the present invention and a pharmaceutically acceptable carrier used for the treatment of cancers including, but not limited to, marginal zone lymphoma (MZL), follicular lymphoma (FL), diffuse large B-cell lymphoma (DLBCL), and chronic lymphocytic leukemia/small lymphocytic lymphoma (CLL/SLL).

Another aspect of the invention is directed to pharmaceutical compositions comprising a compound of Formula (I)

and a pharmaceutically acceptable carrier. The pharmaceutical acceptable carrier may further include an excipient, diluent, or surfactant.

In one embodiment, are provided methods of treating a disease or disorder associated with modulation of BCL-2 proteins including, cancer or cell proliferative disorder, comprising administering to a patient suffering from at least one of said diseases or disorder a compound of Formula (I).

One therapeutic use of the compounds or compositions of the present invention which inhibit BCL-2 proteins is to provide treatment to patients or subjects suffering from a cancer or cell proliferative disorder.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant. In some embodiments, the pharmaceutical composition can further comprise an additional pharmaceutically active agent.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:
AcCl acetyl chloride
atm atmosphere
br broad
anh. anhydrous
aq. aqueous
BuLi butyl lithium
DCM dichloromethane
DIAD diisopropyl azodiformate
DIPEA N,N-diisopropylethylamine
DMAc N,N-dimethyl acetamide
DMAP N,N-dimethylpyridin-4-amine
DME 1,2-Dimethoxyethane
DMEDA N,N'-Dimethylethylenediamine
DMF N,N-dimethyl formamide
DMSO dimethyl sulfoxide
EDCI 1-(3-Dimethylaminopropyl)-3-ethylcarbodiimide
ESI electrospray ionization
Et-I iodoethane
EtOAc ethyl acetate
EtOH ethanol
FA formic acid
h hour(s)
Hal halogen
HATU [bis(dimethylamino)methylene]-1H-1,2,3-triazolo[4,5-b]pyridinium 3-oxide hexafluorophosphate
HPLC high pressure (or performance) liquid chromatography
t-BuOK potassium tert-butoxide
LCMS liquid chromatography mass spectrometry
LHMDS Lithium bis(trimethylsilyl)amide
m multiplet
M molar
MeCN acetonitrile
2-MeTHF 2-methyl tetrahydrofuran
MeOH methanol
MHz megahertz
min minutes
MS molecular sieves
MsCl methanesulfonyl chloride
n-BuLi butyl lithium
NBS N-bromosuccinimide
NMR nuclear magnetic resonance
ppm parts per million
quant. Quantitative
rac racemic mixture
rt room temperature
Rt retention time sat. saturated
TBAB tetrabutylammonium bromide
TBTU O-(Benzotriazol-1-yl)-N,N,N',N'-tetramethyluronium tetrafluoroborate
t-BuOH tert-butanol
TFA trifluoroacetic acid
THF tetrahydrofuran
TLC thin layer chromatography Examples Synthesis of Intermediates Preparation 1: (3S)-3-(morpholin-4-ylmethyl)-1,2,3,4-tetrahydroisoquinoline

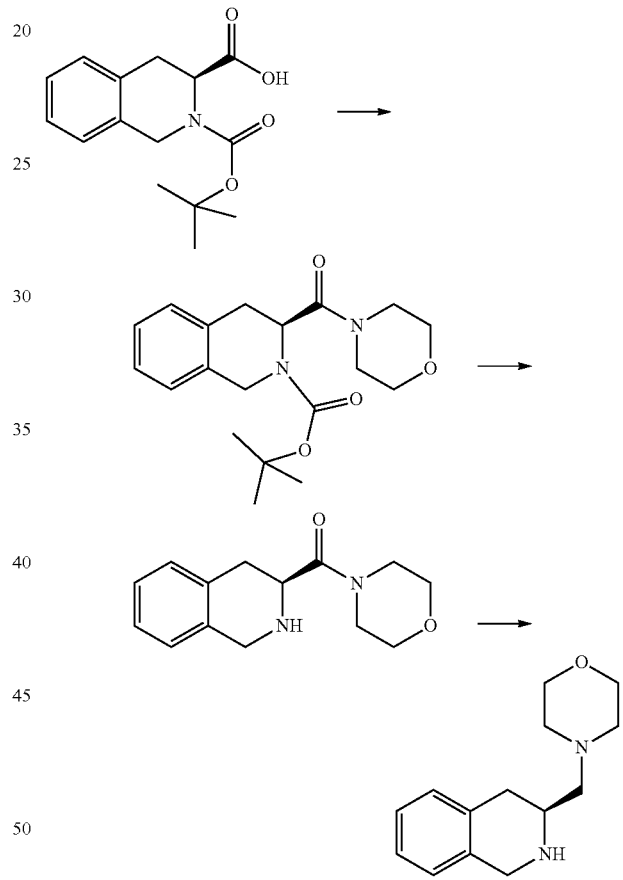

Step A: Synthesis of tert-Butyl (3S)-3-(morpholin-4-ylcarbonyl)-3,4-dihydroisoquinoline-2(1H)-carboxylate A mixture of (3S)-2-(tert-butoxycarbonyl)-1,2,3,4-tetrahydroisoquinoline-3-carboxylic acid (20.4 g, 74 mmol), Et₃N (8.9 g, 88 mmol), morpholine (8.3 g, 95 mmol), and CH₃CN (150 mL) was stirred at ambient temperature for 15 minute, then TBTU (28.3 g, 88 mmol) was added. The reaction mixture was stirred at ambient temperature overnight, partitioned between EtOAc (200 mL) and saturated aqueous solution of NaHCO₃ (100 mL), the layers were separated, and the aqueous one was extracted once more with EtOAc. The combined organic layers were dried over MgSO$_4$, filtered, and concentrated under reduced pressure to afford 20.7 g (81%) of crude product that was used for the next step without further purification.

Step B: Synthesis of (3S)-3-(Morpholin-4-ylcarbonyl)-1,2,3,4-tetrahydroisoquinoline A solution of HCl in 1.4-dioxane (3M, 100 mL) was added portion wise to a stirred solution of crude material obtained at Step A (20.7 g, 59 mmol) in 1,4-dioxane (50 mL). The reaction mixture was stirred for 4 hours at ambient temperature and concentrated under reduced pressure, the residue was dissolved in CH$_2$Cl$_2$ (250 mL), and the saturated aqueous solution of Na$_2$CO$_3$ (100 mL) was added to the stirred mixture. The organic layer was separated, dried over MgSO$_4$, filtered, and concentrated under reduced pressure to afford 14.7 g (99%) of crude product that was used for the next step without further purification.

Step C: Synthesis of (3S)-3-(morpholin-4-ylmethyl)-1,2,3,4-tetrahydroisoquinoline A solution of the compound obtained at Step B (14.7 g, 60 mmol) in THF (75 mL) was added dropwise to a suspension of LiAlH$_4$ (4.53 g, 120 mmol) in THF (300 mL). The reaction mixture was stirred at ambient temperature overnight, cooled to 0° C., quenched by addition dropwise of 40% aqueous solution of NaOH (5 mL), stirred for 45 min, then water (15 mL) was added, and the reaction mixture was stirred additionally for 30 min. The organic layer was separated, and the aqueous one was extracted twice with THF. Combined organic layers were dried over MgSO$_4$, filtered, and concentrated under reduced pressure to afford 13.5 g (97.4%) of crude product that was used for the next step without further purification.

Preparation 2: (3R)-3-(morpholin-4-ylmethyl)-1,2,3,4-tetrahydroisoquinoline

The procedure was as in the process of Preparation 1, using (R)-2-(tert-butoxycarbonyl)-1,2,3,4-tetrahydroisoquinoline-3-carboxylic acid as a starting material.

Preparation 3: Ethyl 6-bromo-1,3-benzodioxole-5-carboxylate

Step A: Synthesis of 6-bromo-1,3-benzodioxole-5-carboxylic Acid

A solution of 1,3-benzodioxole-5-carboxylic acid (30 g; 180 mmol) in 1M aqueous solution of NaOH (200 mL) was cooled to 2-5° C., and NBS (41.8 g; 23 mmol) was added portion wise. The resulted mixture was stirred at 10° C. for 1 hour and then additionally at ambient temperature overnight, cooled to 2-5° C., and acidified to pH 2 with 10% HCl. The precipitate formed was filtered off, washed with water and dried by lyophilization to give 39.4 g (89%) of crude product that was used for the next step without further purification.

Step B: Synthesis of Ethyl 6-bromo-1,3-benzodioxole-5-carboxylate

A mixture of bromo-acid obtained at Step A (39.4 g, 160 mmol), H$_2$SO$_4$ (10 g, 5.8 mL), and EtOH (350 mL) was stirred at 80° C. overnight and then concentrated under reduced pressure. The residue was treated with water (300 mL) and basified with saturated aqueous solution of Na$_2$CO$_3$ to pH 10. The product was extracted with EtOAc (3×200 mL). The combined organic layers were dried over anhydrous MgSO$_4$ and concentrated under reduced pressure. The residue was purified by silica flash-chromatography using CH$_2$Cl$_2$ as eluent to afford 35.8 g (82%) of the title compound.

Preparation 4: N-[4-(benzyloxy)phenyl]-5,6,7,8-tetrahydroindolizine-1-carboxamide

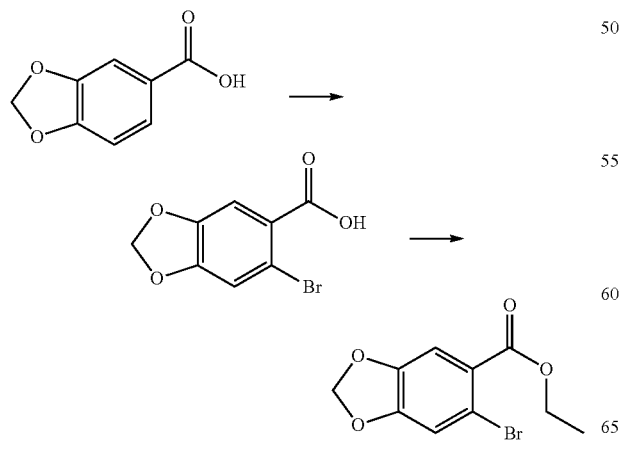

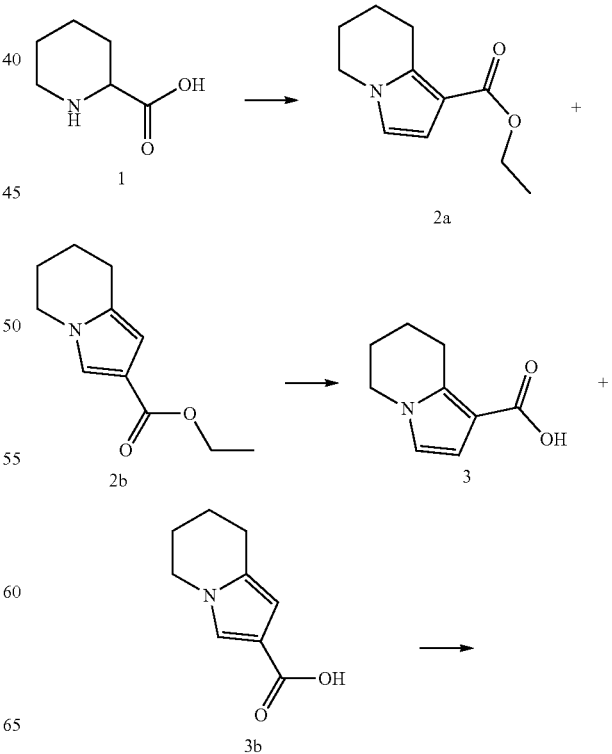

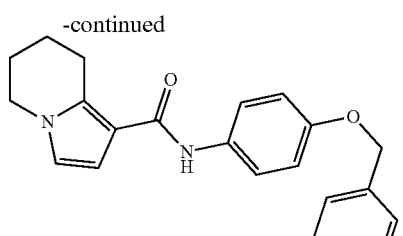

4

Step A: Synthesis of Ethyl 5,6,7,8-tetrahydroindolizine-1-carboxylate (as a Mixture with Ethyl 5,6,7,8-tetrahydroindolizine-2-carboxylate)

Propionic anhydride (90 mL) was added to a stirred solution of piperidine-2-carboxylic acid (21 g, 162 mmol) in formic acid (70 mL) maintaining temperature 0° C. The reaction mixture was allowed to warm to ambient temperature, then stirred for 3 hours, and evaporated to dryness on rotary evaporator under reduced pressure. The residue was dissolved in propionic anhydride (150 mL), ethyl propiolate (78 g, 800 mmol) was added in one portion, and the resulted mixture was stirred and heated at 100° C. for 1 hour. Volatiles were removed under reduced pressure, and the residue was stirred with 20% aqueous solution of $Na_2CO_3$ for 2 hours. The product was extracted with DCM (2×200 mL). Combined organic layers were washed with brine, dried over $Na_2SO_4$, and concentrated on rotary evaporator under reduced pressure to afford 28 g (89%) of crude product as a mixture of isomers ethyl 5,6,7,8-tetrahydroindolizine-1- and 2-carboxylates in ratio 5:1 that was used for the next step without further purification and separation.

Step B: Synthesis of 5,6,7,8-Tetrahydroindolizine-1-carboxylic Acid (as a Mixture with 5,6,7,8-tetrahydroindolizine-2-carboxylic Acid)

A solution of KOH (31.3 g, 560 mmol) in 100 mL of water was added to a solution of the obtained at Step A mixture of esters (28 g, 140 mmol) in methanol (300 mL). The resulted mixture was stirred and heated at 50° C. for 5 h (TLC monitoring). Volatiles were removed under reduced pressure. The residue was diluted with water (400 mL) and acidified with conc. HCl to pH=2. The formed precipitate was filtered off, washed with water, and dried by lyophilization to afford 23 g (77%) of crude product as a mixture of isomers 5,6,7,8-tetrahydroindolizine-1- and 2-carboxylic acids that was used for the next step without further purification and separation.

Step C: Synthesis of N-[4-(benzyloxy)phenyl]-5,6,7,8-tetrahydroindolizine-1-carboxamide A mixture of the crude product obtained at Step B (17.0 g, 100 mol), [4-(benzyloxy)phenyl]amine (18.0 g, 90 mmol), $Et_3N$ (22 mL, 150 mmol), and TBTU (36.0 g, 110 mmol) in $CH_2Cl_2$ (250 mL) was stirred at ambient temperature overnight and quenched with water (200 mL). The organic layer was separated, washed with brine, dried over $Na_2SO_4$, filtered, and the filtrate was evaporated under reduced pressure. The residue after evaporation was subjected to silica flash chromatography eluting with a mixture of EtOAc (0 to 10%) and $CH_2Cl_2$ to afford 14.5 g (41%) of the title compound.

Preparation 5: 6-(1-{[4-(benzyloxy)phenyl]carbamoyl}-5,6,7,8-tetrahydroindolizin-3-yl)-1,3-benzodioxole-5-carboxylic Acid

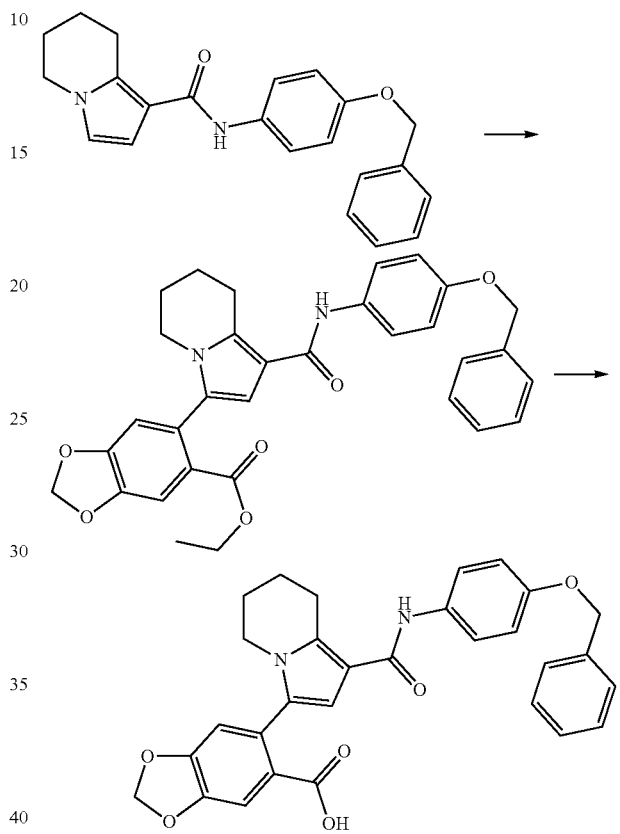

Step A: Synthesis of Ethyl 6-(1-{[4-(benzyloxy)phenyl]carbamoyl}-5,6,7,8-tetrahydroindolizin-3-yl)-1,3-benzodioxole-5-carboxylate A mixture of N-[4-(benzyloxy)phenyl]-5,6,7,8-tetrahydroindolizine-1-carboxamide (See Preparation 4) (10.0 g, 28.9 mol), ethyl 6-bromo-1,3-benzodioxole-5-carboxylate (See Preparation 3) (15.7 g, 58 mmol), $K_3PO_4$ (30.6 g, 47 mmol), pivalic acid (0.88 g, 8.7 mmol) in N,N-dimethylacetamide (100 mL) was stirred at 135° C. for 15 min, then $PdCl_2(PPh_3)_2$ (4.0 g, 6 mmol) was added. The resulting mixture was stirred at 135° C. for 30 min. Upon completion of the reaction mixture was partitioned between water (200 mL) and EtOAC (200 mL). The organic layer was separated, washed with brine, dried over sodium sulfate, filtered, and concentrated under reduced pressure. The residue was subjected to silica flash chromatography eluting with a mixture of EtOAc (0 to 10%) and $CH_2Cl_2$ to afford 12.0 g (80%) of the title compound.

Step B: Synthesis of 6-(1-{[4-(benzyloxy)phenyl]carbamoyl}-5,6,7,8-tetrahydroindolizin-3-yl)-1,3-benzodioxole-5-carboxylic acid A solution of ester obtained at Step A (12.0 g, 23 mmol) and NaOH (4.0 g, 100 mol) in a mixture of EtOH (100 mL)

and water (10 mL) was stirred at ambient temperature for 12 h. The volatiles were removed under reduced pressure, and water (100 mL) was added to the residue. The solution was acidified with 6M HCl to pH 1 and extracted with CH₂Cl₂ (2×200 mL); the combined organic layers were dried over Na₂SO₄ and evaporated to dryness under reduced pressure to afford 9.0 g (78%) of the title compound that was pure enough to be used further for the next step.

Preparation 6: N-[4-(benzyloxy)phenyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide

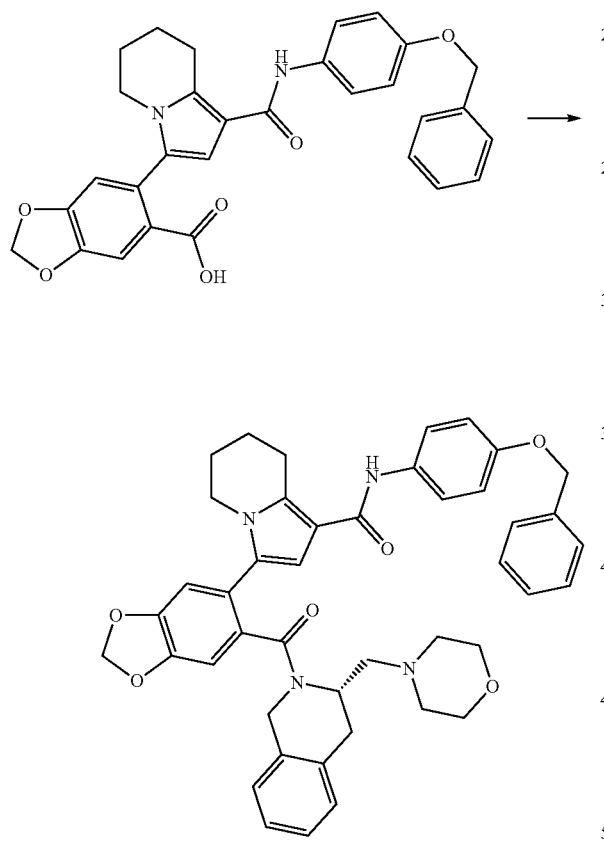

A mixture of 6-(1-{[4-(benzyloxy)phenyl]carbamoyl}-5,6,7,8-tetrahydroindolizin-3-yl)-1,3-benzodioxole-5-carboxylic acid (9.0 g, 18 mmol) (See Preparation 5), (3 S)-3-(morpholin-4-ylmethyl)-1,2,3,4-tetrahydroisoquinoline (4.5 g, 19 mmol) (See Preparation 1), DIPEA (4.6 mL, 26 mmol), and TBTU (6.2 g, 19 mmol), and DMF (100 mL) was stirred at 60° C. overnight. The reaction mixture was partitioned between water (200 mL) and EtOAc (200 mL). The organic layer was separated, washed with brine, dried over Na₂SO₄, filtered, and concentrated under reduced pressure. The residue was subjected to silica flash chromatography eluting with a mixture of EtOAc (0 to 100%) and CH₂Cl₂ to afford 10.0 g (78%) of the title compound.

Preparation 7: N-[4-(benzyloxy)phenyl]-3-(6-{[(3R)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide

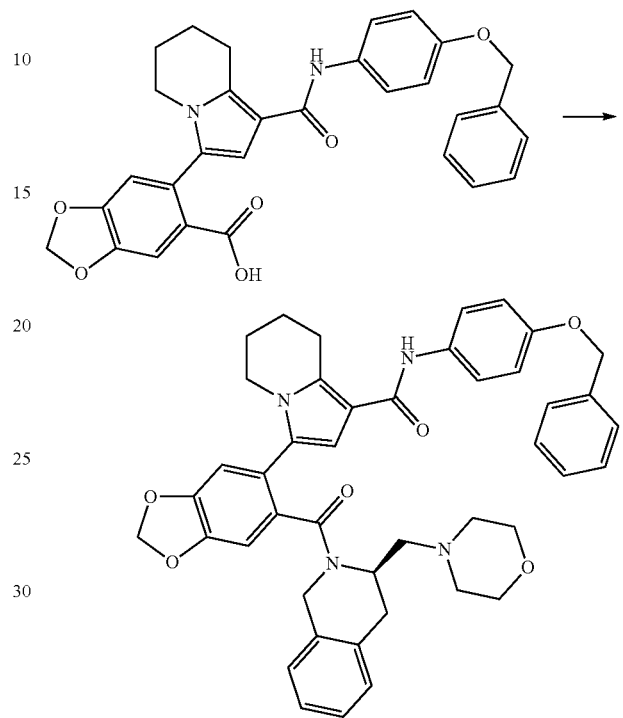

The procedure was as in the process of Preparation 7, using (3R)-3-(morpholin-4-ylmethyl)-1,2,3,4-tetrahydroisoquinoline (See Preparation 2) as a starting material.

Preparation 8: 3-[([4-(benzyloxy)phenyl]{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic Acid

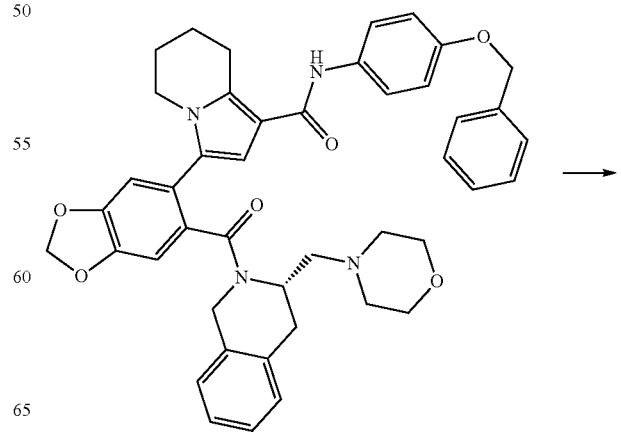

-continued

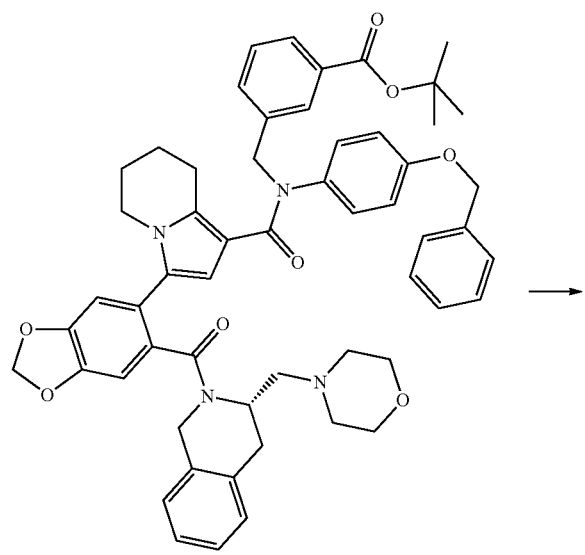

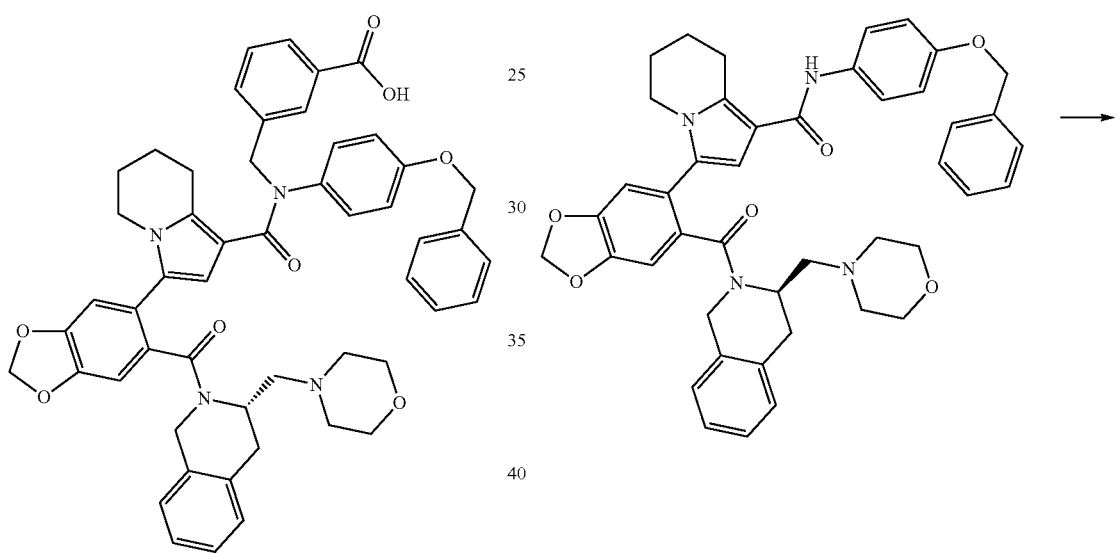

Step A: Synthesis of tert-butyl 3-[([4-(benzyloxy)phenyl]{[3-(6-{[(3S)-3-(morpholin-4-ylmethyl)-3,4-dihydroisoquinolin-2(1H)-yl]carbonyl}-benzodioxol-5-yl)-5,6,7,8-tetrahydroindolizin-1-yl]carbonyl}amino)methyl]benzoate A mixture of N-[4-(benzyloxy)phenyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See Preparation 6) (1.0 g, 1.4 mmol) t-BuOK (0.6 g 5.5 mmol), and t-BuOH (50 mL) was stirred at 50° C. for 30 min, then tert-butyl 3-(bromomethyl) benzoate (0.75 g, 2.8 mmol) was added. The reaction mixture was stirred at 60° C. for 12 h and partitioned between EtOAc and water. The organic layer was separated, washed with brine, dried over Na$_2$SO$_4$, filtered, concentrated under reduced pressure. The residue was subjected to silica flash chromatography eluting with a mixture of EtOAc (0 to 100%) and CH$_2$Cl$_2$ to afford 1.2 g (95%) of the title compound.

Step B: Synthesis of 3-[([4-(benzyloxy)phenyl]{[3-(6-{[(3S)-3-(morpholin-4-ylmethyl)-3,4-dihydroisoquinolin-2(1H)-yl]carbonyl}-benzodioxol-5-yl)-5,6,7,8-tetrahydroindolizin-1-yl]carbonyl}amino)methyl]benzoic Acid To a stirred solution of the ester obtained at the Step A (1.2 g, 1.3 mmol) in dichloromethane (10 mL) TFA (0.8 mL, 9.8 mmol) was added. The reaction mixture was stirred at ambient temperature for 12 h and concentrated under reduced pressure to afford 0.8 g (81%) of the title compound that was used for the next step without further purification.

Preparation 9: 3-[([4-(benzyloxy)phenyl]{[3-(6-{[(3R)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic Acid

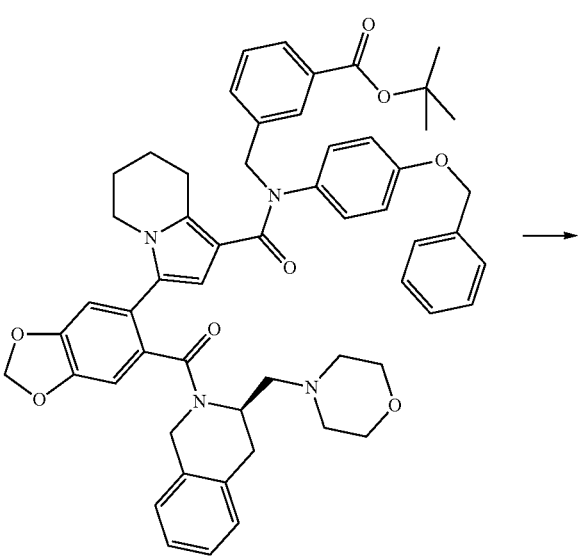

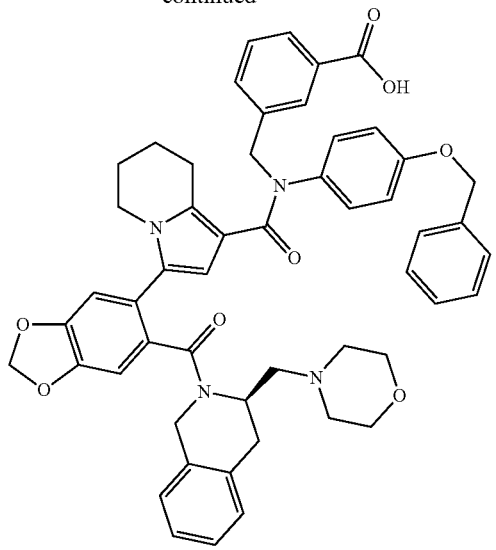

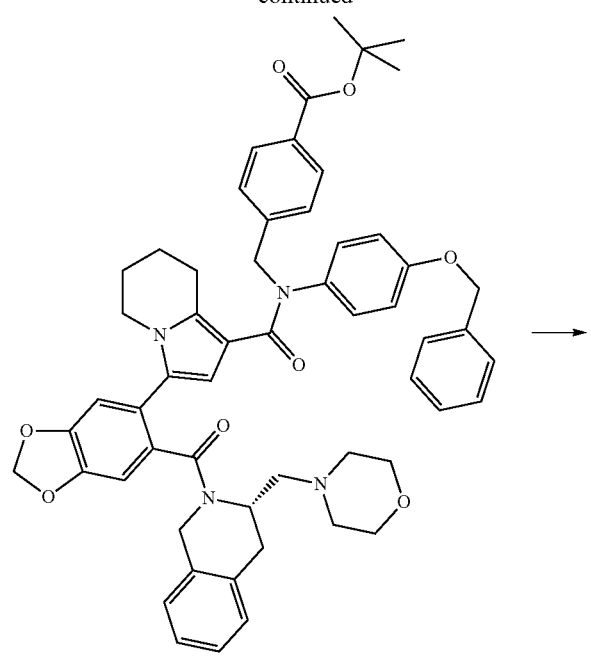

The procedure was as in the process of Preparation 8, using N-[4-(benzyloxy)phenyl]-3-(6-{[(3R)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide as a starting material (See Preparation 7).

Preparation 10: 4-[([4-(benzyloxy)phenyl]{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic Acid

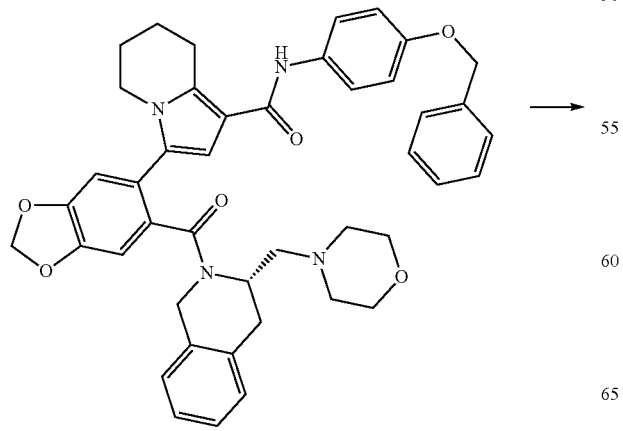

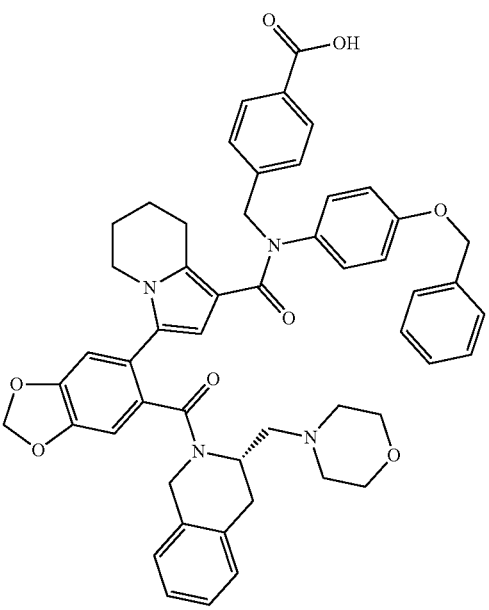

The procedure was as in the process of Preparation 8, using N-[4-(benzyloxy)phenyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See Preparation 6) as a starting material.

Preparation 11: 4-[([4-(benzyloxy)phenyl]{[3-(6-{[(3R)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic Acid

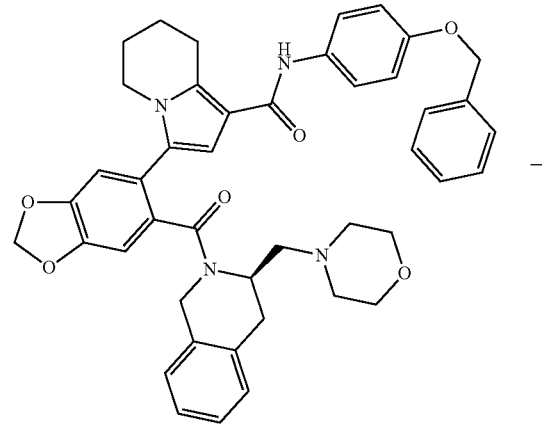

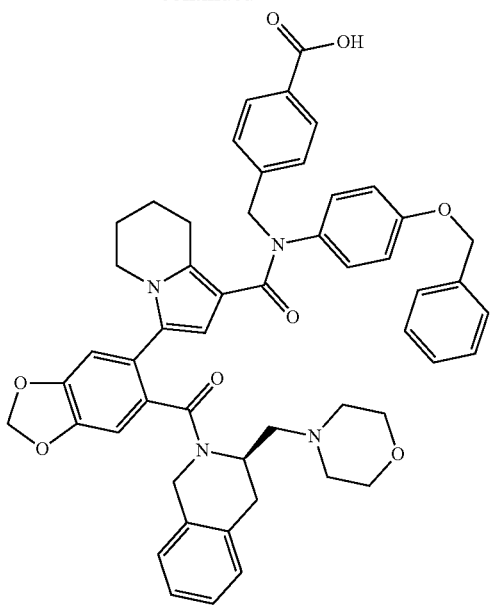

The procedure was as in the process of Preparation 8, using N-[4-(benzyloxy)phenyl]-3-(6-{[(3R)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See Preparation 7) as a starting material.

Example 1: Synthesis of N-benzyl-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 15)

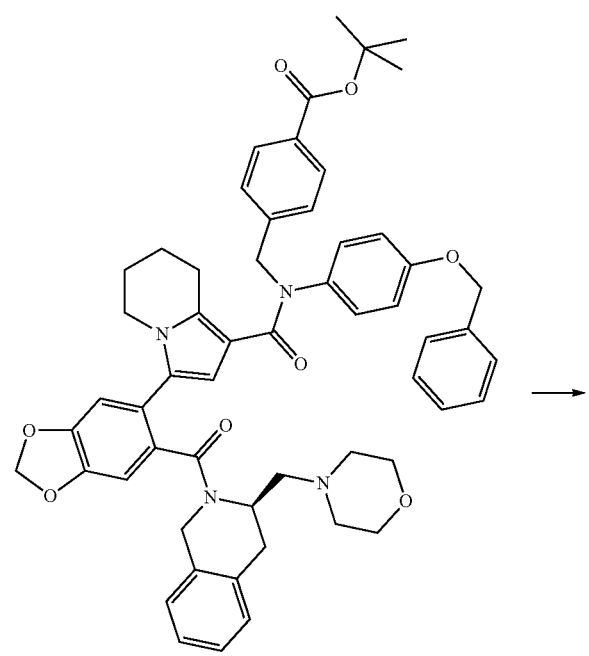

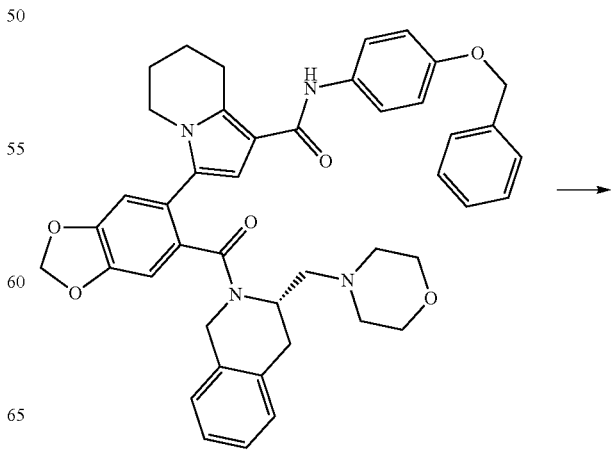

55
-continued

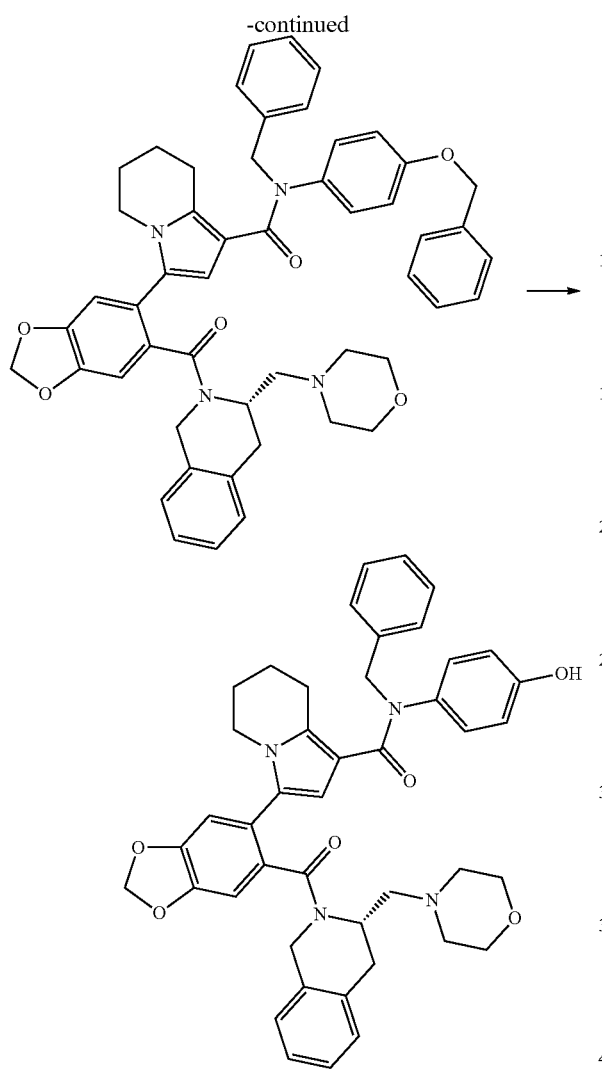

Step A: Synthesis of N-benzyl-N-[4-(benzyloxy)phenyl]-3-(6-{[(3S)-3-(morpholin-4-ylmethyl)-3,4-dihydroisoquinolin-2(1H)-yl]carbonyl}-benzodioxol-5-yl)-5,6,7,8-tetrahydroindolizine-1-carboxamide A mixture of N-[4-(benzyloxy)phenyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See Preparation 6) (150 mg, 0.2 mmol), t-BuOK (92 mg 0.8 mmol), and t-BuOH (5 mL) was stirred at 50° C. for 30 min, then benzyl bromide (68 mg, 0.4 mmol) was added. The reaction mixture was stirred at 60° C. for 12 h and then partitioned between EtOAc and water. The organic layer was separated, washed with brine, dried over Na$_2$SO$_4$, filtered, concentrated under reduced pressure. The residue was subjected to silica flash chromatography eluting with a mixture of EtOAc (0 to 100%) and CH$_2$Cl$_2$ to afford 150 mg (89%) of the title compound.

56

Step B: Synthesis of N-benzyl-N-(4-hydroxyphenyl)-3-(6-{[(3S)-3-(morpholin-4-ylmethyl)-3,4-dihydroisoquinolin-2(1H)-yl]carbonyl}-benzodioxol-5-yl)-5,6,7,8-tetrahydroindolizine-1-carboxamide A stirred mixture of the compound obtained at Step A, catalyst (10 mg of 5% Pd on charcoal), and methanol (2 mL) was hydrogenated under H$_2$ atmosphere for 2 h. The catalyst was filtered off, and the filtrate was evaporated to dryness. The residue was subjected to HPLC purification to afford 140 mg (95%) of the title compound.

Example 2: Synthesis of N-(4-hydroxyphenyl)-N-(2-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 4)

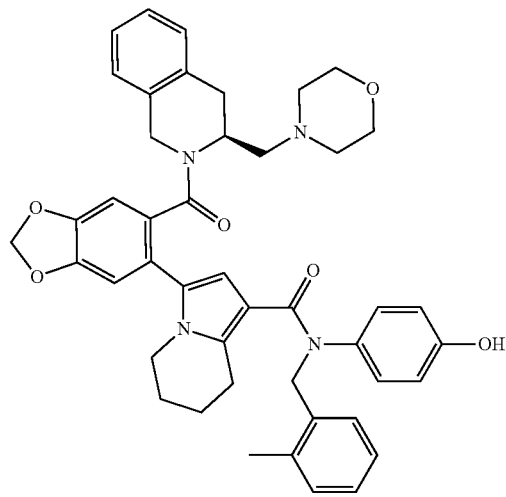 [SMILES: Cc1ccccc1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 2-methylbenzyl chloride instead of benzyl bromide at Step A.

Example 3: Synthesis of N-(4-hydroxyphenyl)-N-(3-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 14)

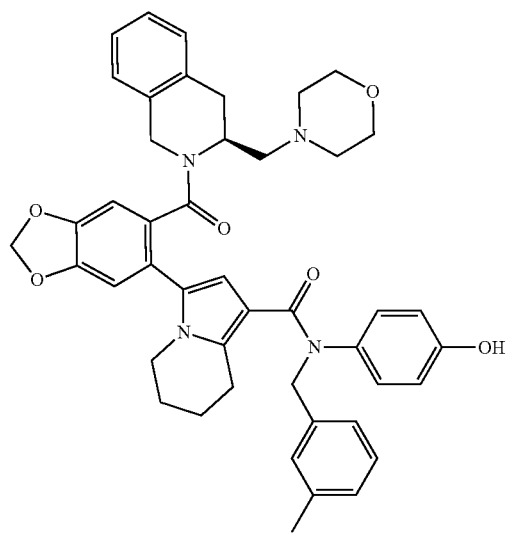 [SMILES: Cc1cccc(CN(C(=O)c2cc(-c3cc4c(cc3C(=O)N3Cc5ccccc5C[C@H]3CN3CCOCC3)OCO4)n3c2CCCC3)c2ccc(O)cc2)c1]

The procedure was as in the process of Example 1 using 1-(bromomethyl)-3-methylbenzene instead of benzyl bromide at Step A.

Example 4: Synthesis of N-(4-hydroxyphenyl)-N-(4-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 20)

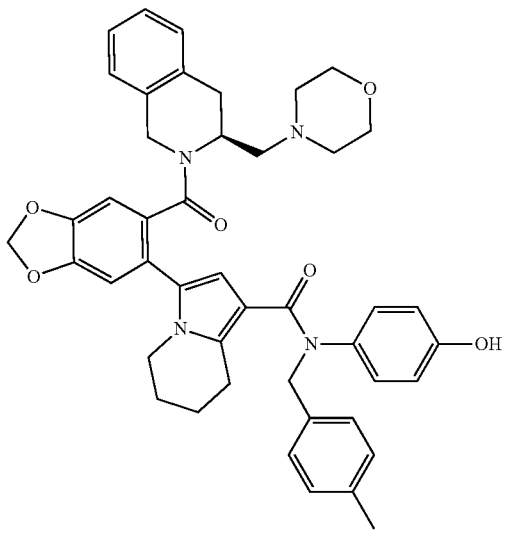 [SMILES: Cc1ccc(CN(C(=O)c2cc(-c3cc4c(cc3C(=O)N3Cc5ccccc5C[C@H]3CN3CCOCC3)OCO4)n3c2CCCC3)c2ccc(O)cc2)cc1]

The procedure was as in the process of Example 1 using 4-methylbenzyl chloride instead of benzyl bromide at Step A.

Example 5: Synthesis of N-(2-fluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 11)

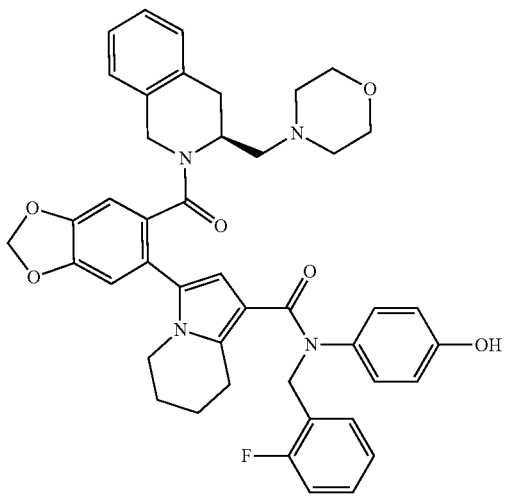 [SMILES: O=C(c1cc(-c2cc3c(cc2C(=O)N2Cc4ccccc4C[C@H]2CN2CCOCC2)OCO3)n2c1CCCC2)N(Cc1ccccc1F)c1ccc(O)cc1]

The procedure was as in the process of Example 1 using 1-(chloromethyl)-2-fluorobenzene instead of benzyl bromide at Step A.

Example 6: Synthesis of N-(3-fluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 21)

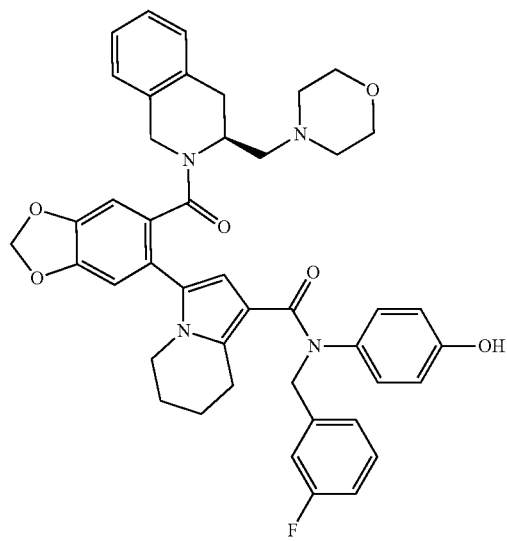 [SMILES: O=C(c1cc(-c2cc3c(cc2C(=O)N2Cc4ccccc4C[C@H]2CN2CCOCC2)OCO3)n2c1CCCC2)N(Cc1cccc(F)c1)c1ccc(O)cc1]

The procedure was as in the process of Example 1 using 1-(chloromethyl)-3-fluorobenzene instead of benzyl bromide at Step A.

Example 7: Synthesis of N-(4-fluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 17)

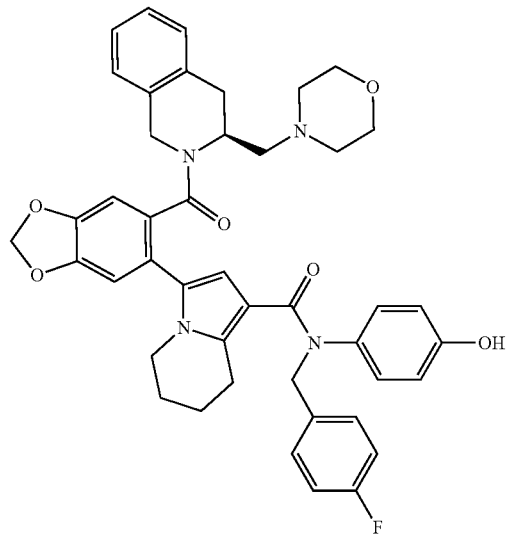 [SMILES: O=C(c1cc(-c2cc3c(cc2C(=O)N2Cc4ccccc4C[C@H]2CN2CCOCC2)OCO3)n2c1CCCC2)N(Cc1ccc(F)cc1)c1ccc(O)cc1]

The procedure was as in the process of Example 1 using 1-(bromomethyl)-4-fluorobenzene instead of benzyl bromide at Step A.

Example 8: Synthesis of N-(2,6-dimethylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 30)

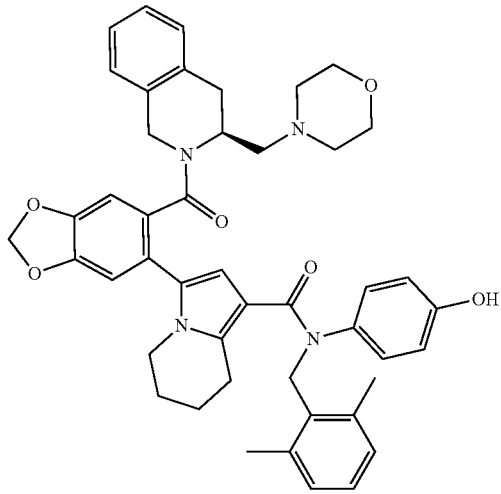 [SMILES: Cc1cccc(C)c1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 2-(bromomethyl)-1,3-dimethylbenzene instead of benzyl bromide at Step A.

Example 9: Synthesis of N-(4-hydroxyphenyl)-N-(2-methoxybenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 31)

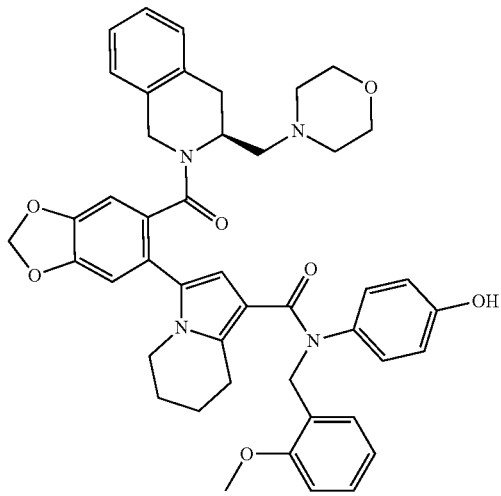 [SMILES: COc1ccccc1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 2-(bromomethyl)-1,3-dimethylbenzene instead of benzyl bromide at Step A.

Example 10: Synthesis of N-(2-fluoro-6-methylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 32)

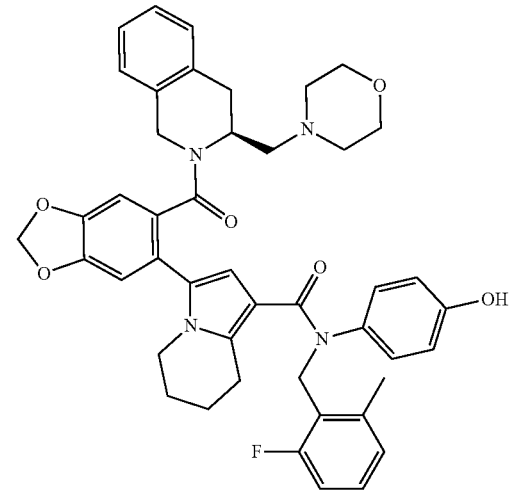 [SMILES: Cc1cccc(F)c1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 2-(bromomethyl)-1-fluoro-3-methylbenzene instead of benzyl bromide at Step A.

Example 11: Synthesis of N-(2-chlorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 33)

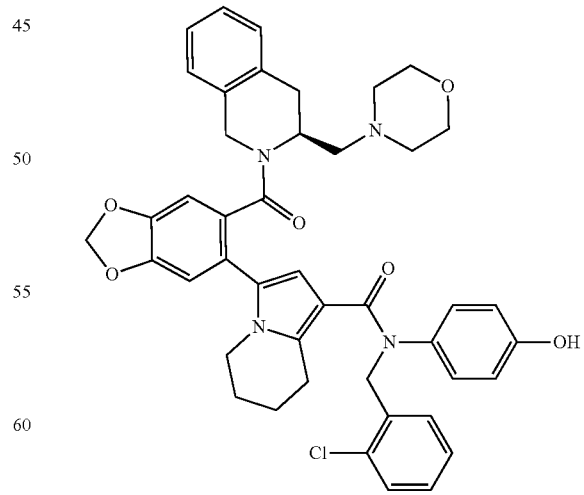

The procedure was as in the process of Example 1 using 1-chloro-2-(chloromethyl)benzene instead of benzyl bromide at Step A.

Example 12: Synthesis of N-(2,6-difluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 19)

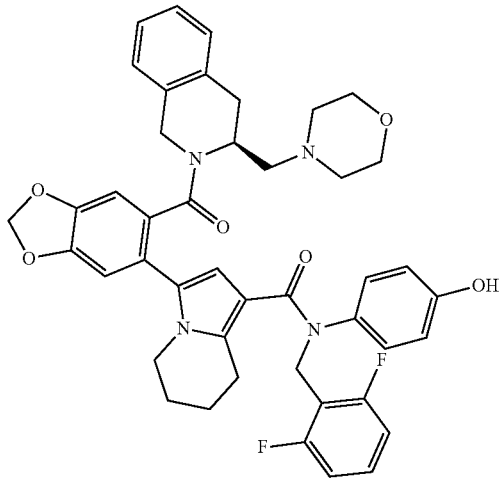 [SMILES: O=C(c1cc(-c2cc3c(cc2C(=O)N2Cc4ccccc4C[C@H]2CN2CCOCC2)OCO3)n2c1CCCC2)N(Cc1c(F)cccc1F)c1ccc(O)cc1]

The procedure was as in the process of Example 1 using 2-(chloromethyl)-1,3-difluorobenzene instead of benzyl bromide at Step A.

Example 13: Synthesis of N-(4-hydroxyphenyl)-N-(3-methoxy-2-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 3)

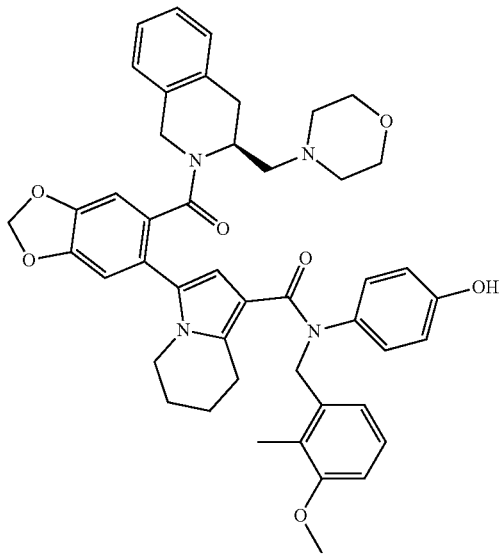 [SMILES: COc1cccc(CN(C(=O)c2cc(-c3cc4c(cc3C(=O)N3Cc5ccccc5C[C@H]3CN3CCOCC3)OCO4)n3c2CCCC3)c2ccc(O)cc2)c1C]

The procedure was as in the process of Example 1 using 1-(bromomethyl)-3-methoxy-2-methylbenzene instead of benzyl bromide at Step A.

Example 14: Synthesis of N-(2-chloro-6-methylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 34)

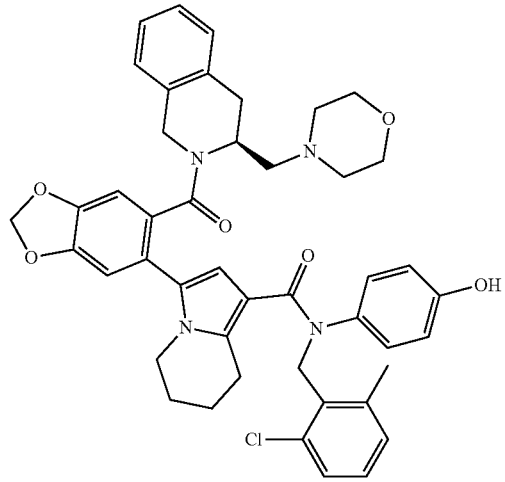 [SMILES: Cc1cccc(Cl)c1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 1-chloro-2-(chloromethyl)-3-methylbenzene instead of benzyl bromide at Step A.

Example 15: Synthesis of N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[2-(trifluoromethyl)benzyl]-5,6,7,8-tetrahydroindolizine-1-carboxamide (Compound 5)

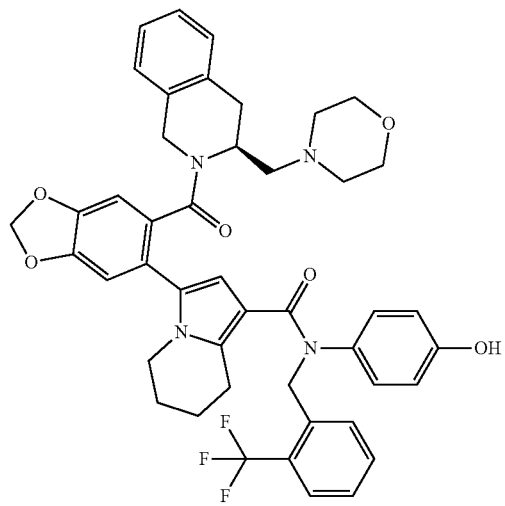 [SMILES: O=C(c1cc(-c2cc3c(cc2C(=O)N2Cc4ccccc4C[C@H]2CN2CCOCC2)OCO3)n2c1CCCC2)N(Cc1ccccc1C(F)(F)F)c1ccc(O)cc1]

The procedure was as in the process of Example 1 using 1-(chloromethyl)-2-(trifluoromethyl)benzene instead of benzyl bromide at Step A.

Example 16: Synthesis of N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[3-(trifluoromethyl)benzyl]-5,6,7,8-tetrahydroindolizine-1-carboxamide (Compound 16)

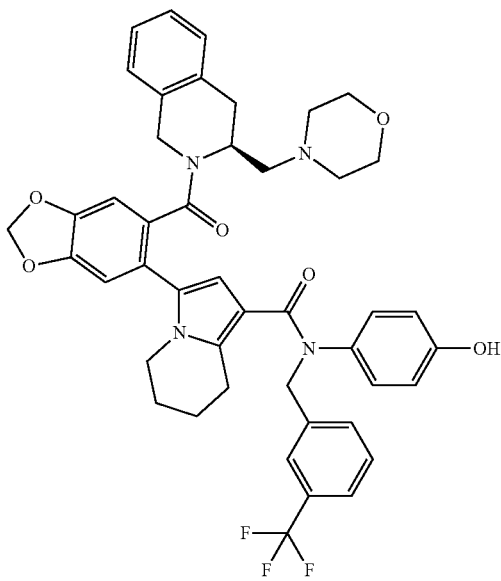 [SMILES: O=C(c1cc(-c2cc3c(cc2C(=O)N2Cc4ccccc4C[C@H]2CN2CCOCC2)OCO3)n2c1CCCC2)N(Cc1cccc(C(F)(F)F)c1)c1ccc(O)cc1]

The procedure was as in the process of Example 1 using 1-(chloromethyl)-3-(trifluoromethyl)benzene instead of benzyl bromide at Step A.

Example 17: Synthesis of N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[4-(trifluoromethyl)benzyl]-5,6,7,8-tetrahydroindolizine-1-carboxamide (Compound 24)

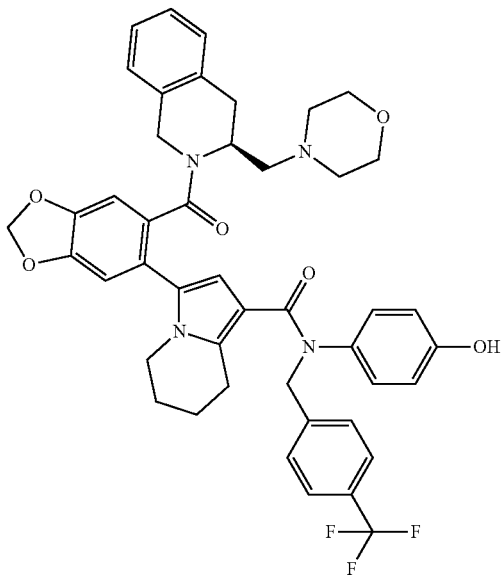 [SMILES: O=C(c1cc(-c2cc3c(cc2C(=O)N2Cc4ccccc4C[C@H]2CN2CCOCC2)OCO3)n2c1CCCC2)N(Cc1ccc(C(F)(F)F)cc1)c1ccc(O)cc1]

The procedure was as in the process of Example 1 using 1-(bromomethyl)-4-(trifluoromethyl)benzene instead of benzyl bromide at Step A.

Example 18: Synthesis of N-(6-chloro-2,3-difluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 35)

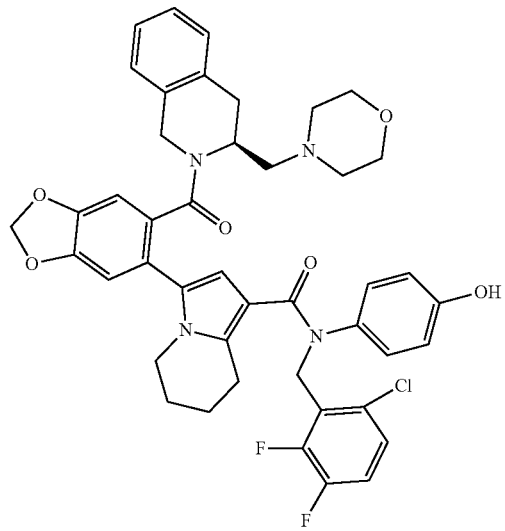 [SMILES: O=C(c1cc(-c2cc3c(cc2C(=O)N2Cc4ccccc4C[C@H]2CN2CCOCC2)OCO3)n2c1CCCC2)N(Cc1c(Cl)ccc(F)c1F)c1ccc(O)cc1]

The procedure was as in the process of Example 1 using 1-chloro-2-(chloromethyl)-3,4-difluorobenzene instead of benzyl bromide at Step A.

Example 19: Synthesis of N-(biphenyl-2-ylmethyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 36)

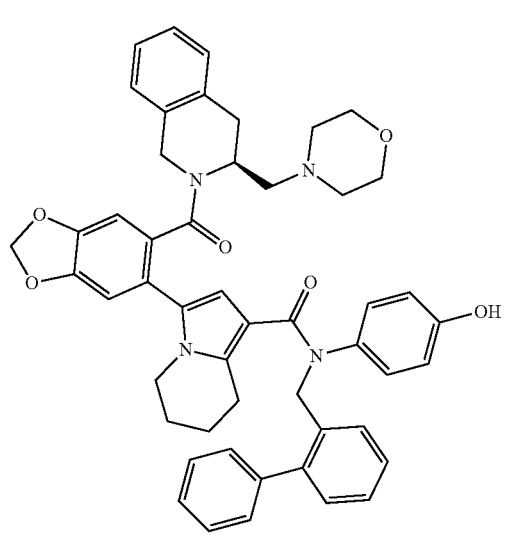 [SMILES: O=C(c1cc(-c2cc3c(cc2C(=O)N2Cc4ccccc4C[C@H]2CN2CCOCC2)OCO3)n2c1CCCC2)N(Cc1ccccc1-c1ccccc1)c1ccc(O)cc1]

The procedure was as in the process of Example 1 using 2-(bromomethyl)biphenyl instead of benzyl bromide at Step A.

Example 20: Synthesis of N-(4-hydroxyphenyl)-N-[2-methyl-4-(trifluoromethyl)benzyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 37)

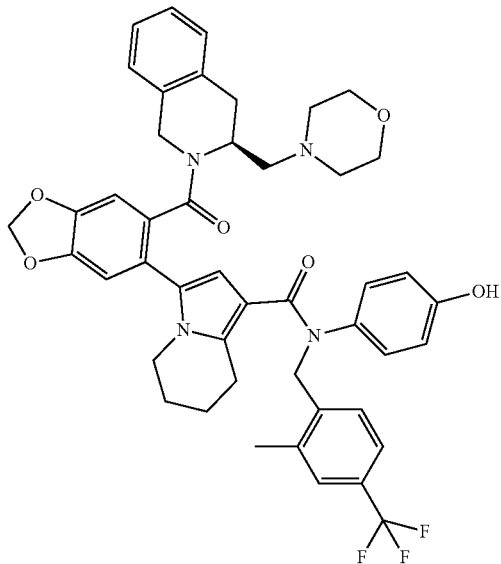 [SMILES: Cc1cc(C(F)(F)F)ccc1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 1-(chloromethyl)-2-methyl-4-(trifluoromethyl)benzene instead of benzyl bromide at Step A.

Example 21: Synthesis of N-(4-hydroxyphenyl)-N-[2-methyl-5-(trifluoromethyl)benzyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 38)

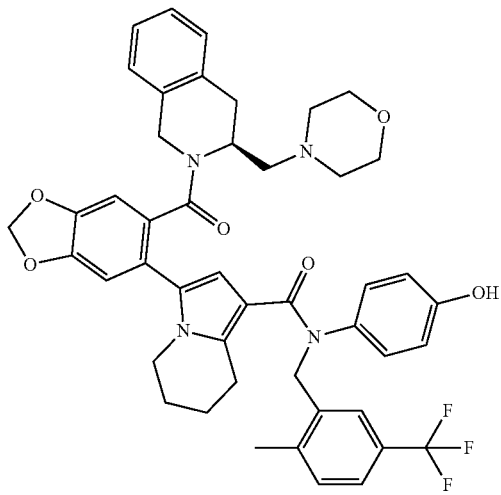 [SMILES: Cc1ccc(C(F)(F)F)cc1CN(C(=O)c1cc(-c2cc3c(cc2C(=O)N2Cc4ccccc4C[C@H]2CN2CCOCC2)OCO3)n2c1CCCC2)c1ccc(O)cc1]

The procedure was as in the process of Example 1 using 2-(bromomethyl)-1-methyl-4-(trifluoromethyl)benzene instead of benzyl bromide at Step A.

Example 22: Synthesis of N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[4-(trifluoromethoxy)benzyl]-5,6,7,8-tetrahydroindolizine-1-carboxamide (Compound 26)

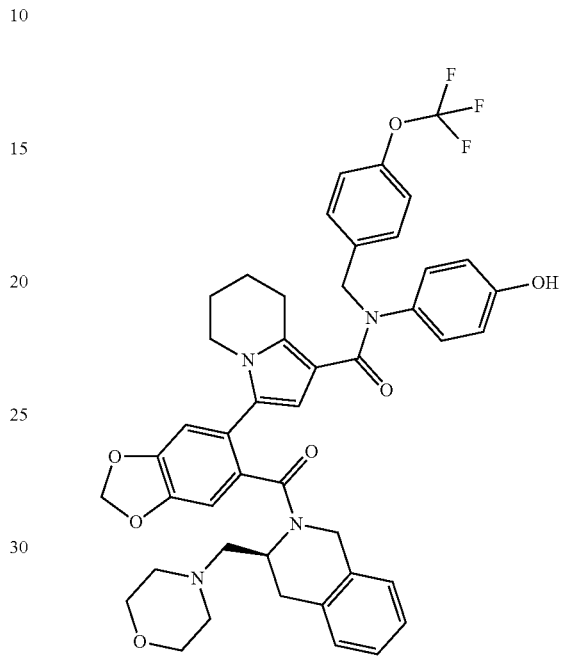

The procedure was as in the process of Example 1 using 1-(chloromethyl)-4-(trifluoromethoxy)benzene instead of benzyl bromide at Step A.

Example 23: Synthesis of N-[2-fluoro-6-(trifluoromethyl)benzyl]-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 22)

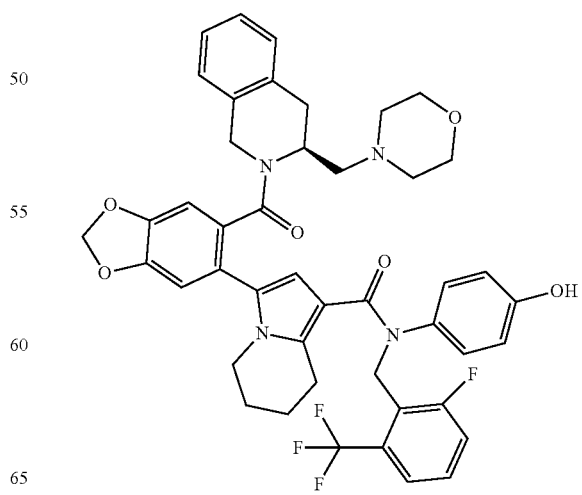

The procedure was as in the process of Example 1 using 2-(bromomethyl)-1-fluoro-3-(trifluoromethyl)benzene instead of benzyl bromide at Step A.

Example 24: N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-(pyridin-3-ylmethyl)-5,6,7,8-tetrahydroindolizine-1-carboxamide (Compound 39)

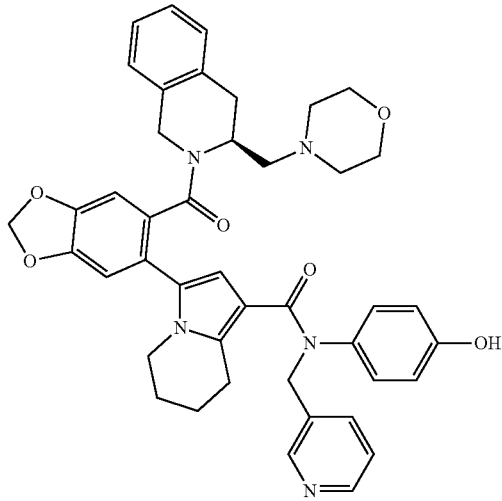 [SMILES: O=C(c1cc(-c2cc3c(cc2C(=O)N2Cc4ccccc4C[C@H]2CN2CCOCC2)OCO3)n2c1CCCC2)N(Cc1cccnc1)c1ccc(O)cc1]

The procedure was as in the process of Example 1 using 3-(chloromethyl)pyridine hydrochloride instead of benzyl bromide at Step A.

Example 25: N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-(pyridin-4-ylmethyl)-5,6,7,8-tetrahydroindolizine-1-carboxamide (Compound 9)

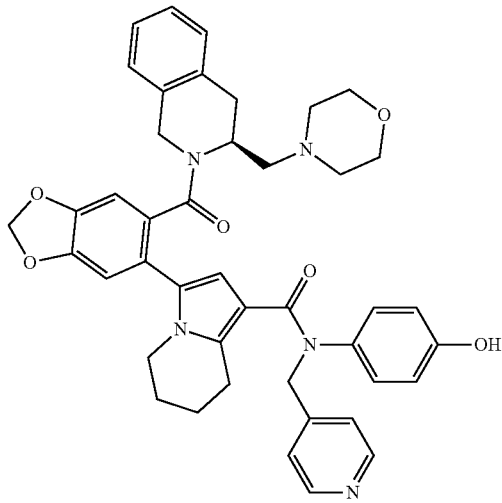 [SMILES: O=C(c1cc(-c2cc3c(cc2C(=O)N2Cc4ccccc4C[C@H]2CN2CCOCC2)OCO3)n2c1CCCC2)N(Cc1ccncc1)c1ccc(O)cc1]

The procedure was as in the process of Example 1 using 4-(chloromethyl)pyridine hydrochloride instead of benzyl bromide at Step A.

Example 26: Synthesis of N-(4-hydroxyphenyl)-N-[(4-methoxy-3,5-dimethylpyridin-2-yl)methyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 23)

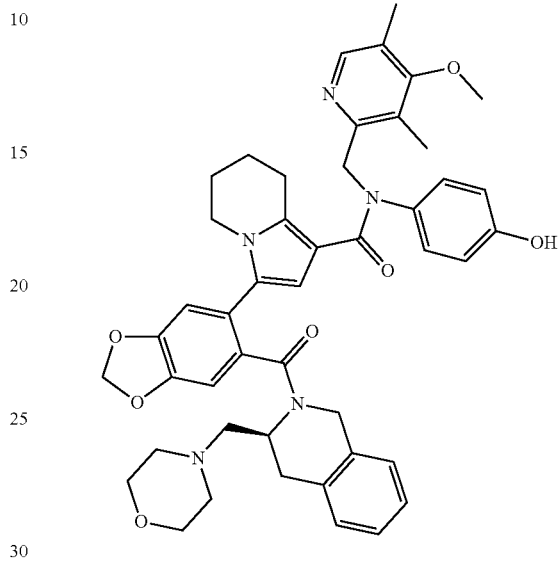

The procedure was as in the process of Example 1 using 2-(chloromethyl)-4-methoxy-3,5-dimethylpyridine hydrochloride instead of benzyl bromide at Step A.

Example 27: N-{[2-(4-ethoxyphenyl)-5-methyl-1,3-oxazol-4-yl]methyl}-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 27)

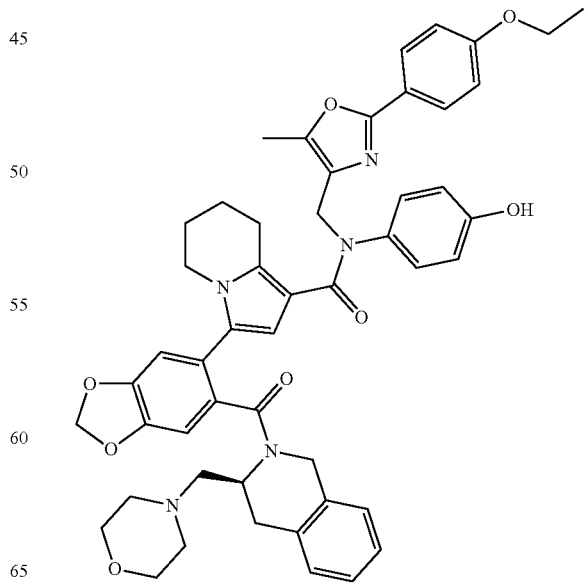

The procedure was as in the process of Example 1 using 4-(chloromethyl)-2-(4-ethoxyphenyl)-5-methyl-1,3-oxazole instead of benzyl bromide at Step A.

Example 28: N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 7)

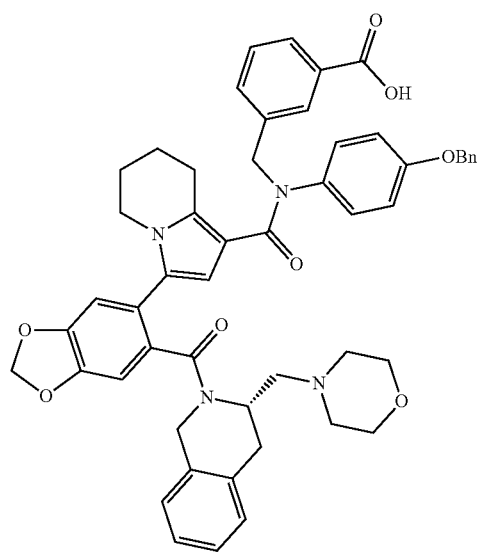

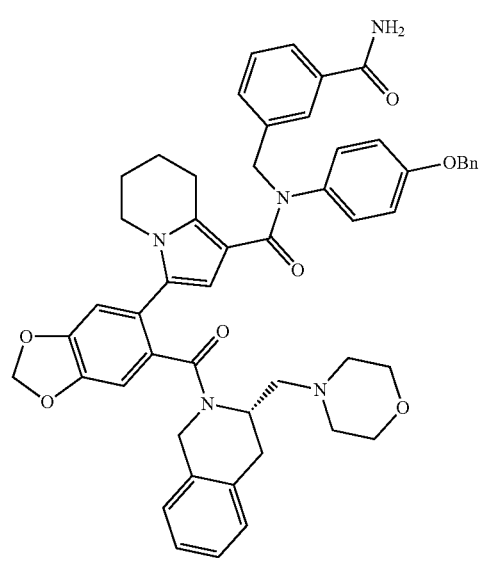

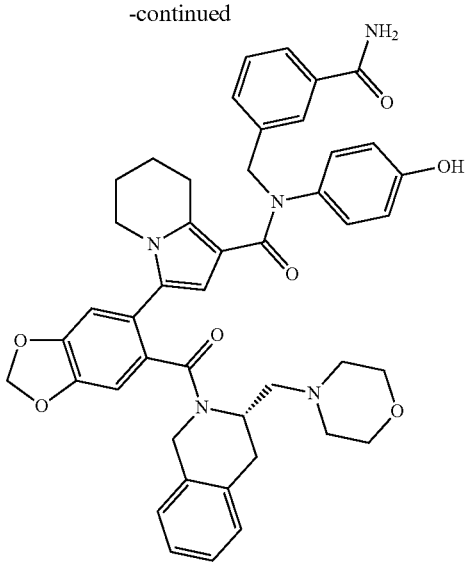

Step A: Synthesis of N-[4-(benzyloxy)phenyl]-N-(3-carbamoylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide A mixture of 3-[([4-(benzyloxy)phenyl]{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic acid (See Preparation 8) (1000 mg, 1.17 mmol), DIPEA (604 mg, 4.68 mmol), ammonium chloride (94 mg, 1.76 mmol) TBTU (490 mg, 1.52 mmol.), and dichloromethane (100 mL) was stirred overnight at ambient temperature then poured into water (100 mL). Organic layer was separated, washed with water, brine, dried over $Na_2SO_4$, and concentrated under reduced pressure. The residue was subjected to silica flash purification using mixture $CH_2Cl_2$/EtOAc (0 to 100%) as an eluent to afford 850 mg (85%) of the title compound.

Step B: Synthesis of N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 7)

A stirred mixture of the compound obtained at Step A (850 mg, 0.995 mmol), catalyst (160 mg of 5% Pd on charcoal), and methanol (70 mL) was hydrogenated under $H_2$ atmosphere for 2 h. The catalyst was filtered off, and the filtrate was evaporated under reduced pressure to dryness. The residue was subjected to HPLC purification to afford 743 mg (97%) of the title compound.

Example 29: Synthesis of N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride (Compound 7 HCl salt)

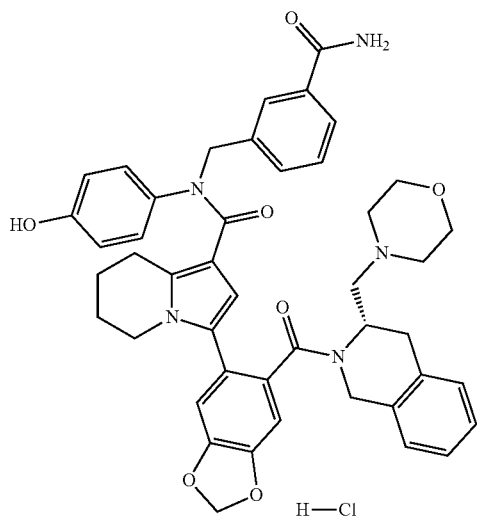

The title compound was obtained from N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See example 28) by treatment of its solution in acetonitrile with an excess of 6M solution of HCl in dioxane followed by removal of volatiles under reduced pressure and washing of the residue with Et$_2$O.

Example 30: Synthesis of N-(4-hydroxyphenyl)-N-{3-[(2-methoxyethyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 2)

The procedure was as in the process of Example 28 using 2-methoxyethyl amine instead of ammonium chloride at Step A.

Example 31: Synthesis of N-(3-{[2-(dimethylamino)ethyl]carbamoyl}benzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 6)

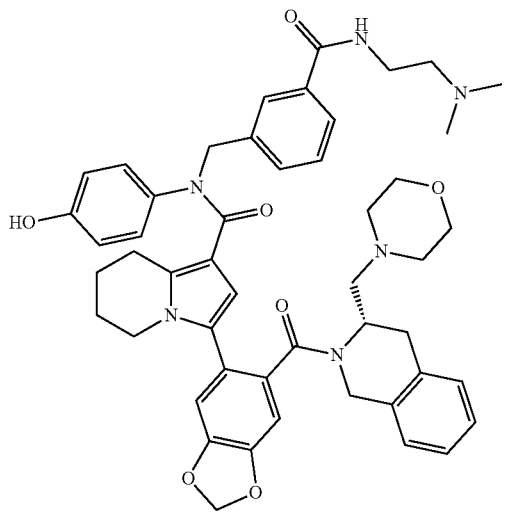

The procedure was as in the process of Example 28 using 2-(dimethylamino)ethyl amine instead of ammonium chloride at Step A.

Example 32: Synthesis of N-(4-hydroxyphenyl)-N-{3-[(4-methylpiperazin-1-yl)carbonyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 10)

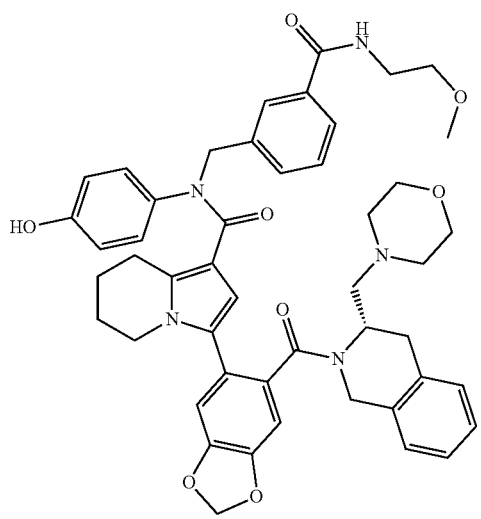 [SMILES: COCCNC(=O)c1cccc(CN(C(=O)c2cc(-c3cc4c(cc3C(=O)N3Cc5ccccc5C[C@H]3CN3CCOCC3)OCO4)n3c2CCCC3)c2ccc(O)cc2)c1]

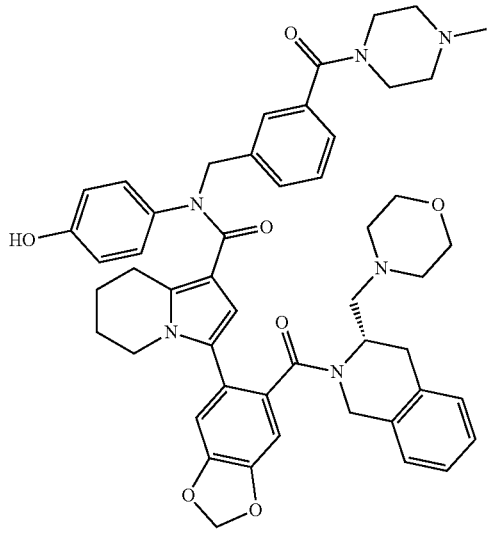 [SMILES: CN1CCN(C(=O)c2cccc(CN(C(=O)c3cc(-c4cc5c(cc4C(=O)N4Cc6ccccc6C[C@H]4CN4CCOCC4)OCO5)n4c3CCCC4)c3ccc(O)cc3)c2)CC1]

The procedure was as in the process of Example 28 using N-methylpyrazine instead of ammonium chloride at Step A.

Example 33: Synthesis of N-(4-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 13)

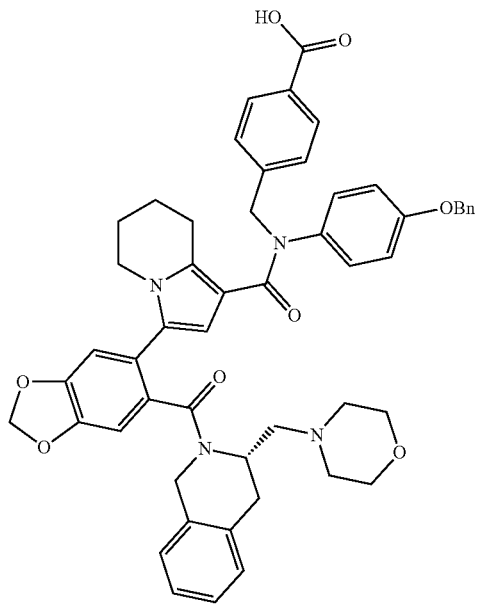

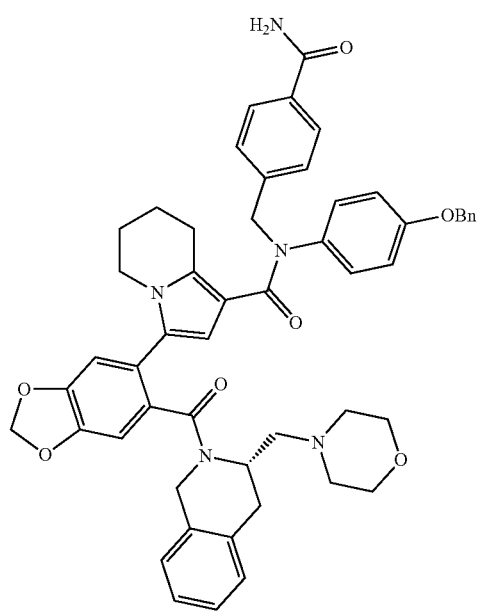

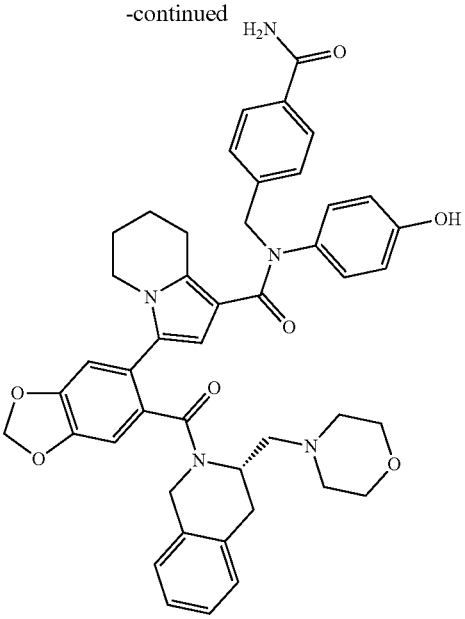

Step A: Synthesis of N-[4-(benzyloxy)phenyl]-N-(4-carbamoylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide A mixture of 4-[([4-(benzyloxy)phenyl]{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic acid (See Preparation 10) (1000 mg, 1.17 mmol), DIPEA (604 mg, 4.68 mmol), ammonium chloride (94 mg, 1.76 mmol) TBTU (490 mg, 1.52 mmol.), and dichloromethane (100 mL) was stirred overnight at ambient temperature then poured into water (100 mL). Organic layer was separated, washed with water, brine, dried over $Na_2SO_4$, and concentrated under reduced pressure. The residue was subjected to silica flash chromatography using mixture $EtOAc/CH_2Cl_2$ (0 to 100%) as an eluent to afford 835 mg (83%) of the title compound.

Step B: Synthesis of N-(4-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide A stirred mixture of the compound obtained at Step A (835 mg, 0.973 mmol), catalyst (160 mg of 5% Pd on charcoal), and methanol (70 mL) was hydrogenated under $H_2$ atmosphere for 2 h. The catalyst was filtered off, and the filtrate was evaporated under reduced pressure to dryness. The residue was subjected to HPLC purification to afford 720 mg (96%) of the title compound.

Example 34: Synthesis of N-(4-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride (Compound 13 HCl salt)

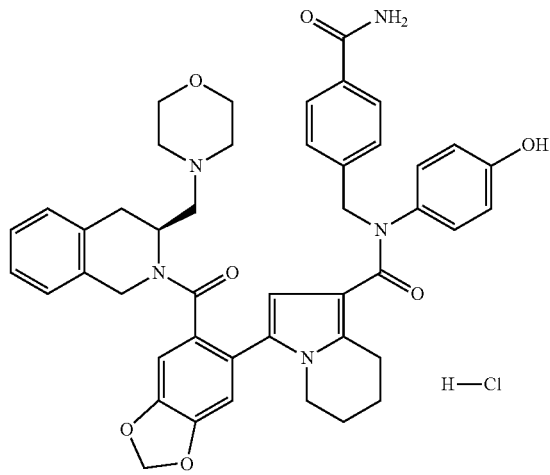 [SMILES: NC(=O)c1ccc(CN(C(=O)c2cc(-c3cc4c(cc3C(=O)N3Cc5ccccc5C[C@H]3CN3CCOCC3)OCO4)n3c2CCCC3)c2ccc(O)cc2)cc1 ; Cl]

The title compound was obtained from N-(4-carbamoylbenzyl)-N-(4-hydroxyphenyl)-3-(6-{[(3 S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See example 33) by treatment of its solution in acetonitrile with an excess of 6M solution of HCl in dioxane followed by removal of volatiles under reduced pressure and washing of the residue with Et₂O.

Example 35: Synthesis of N-(4-hydroxyphenyl)-N-{4-[(2-methoxyethyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 1)

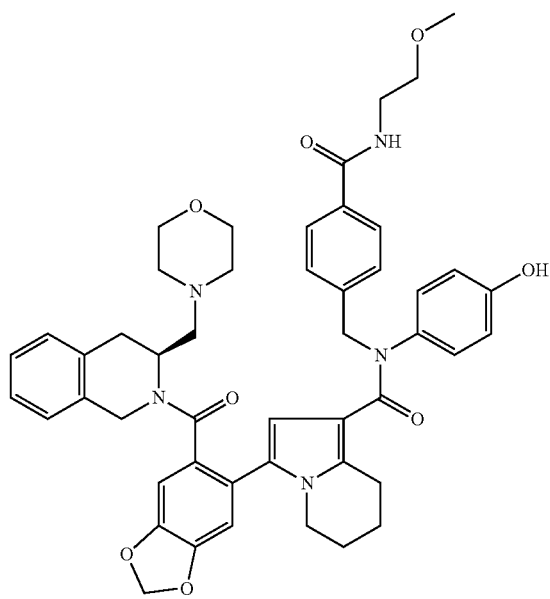 [SMILES: COCCNC(=O)c1ccc(CN(C(=O)c2cc(-c3cc4c(cc3C(=O)N3Cc5ccccc5C[C@H]3CN3CCOCC3)OCO4)n3c2CCCC3)c2ccc(O)cc2)cc1]

The procedure was as in the process of Example 33 using 2-methoxyethyl amine instead of ammonium chloride at Step A.

Example 36: N-(4-hydroxyphenyl)-N-{4-[(2-methoxyethyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide Hydrochloride (Compound 1 HCl Salt)

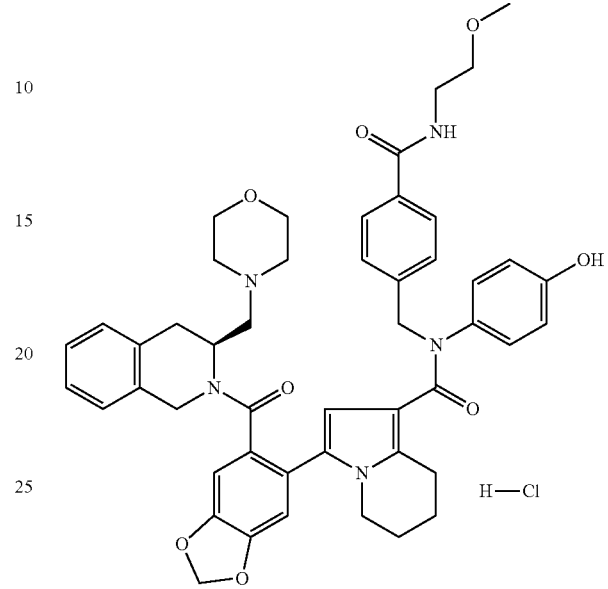

The title compound was obtained from N-(4-hydroxyphenyl)-N-{4-[(2-methoxyethyl)carbamoyl]benzyl}-3-(6-{[(3 S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See example 35) by treatment of its solution in acetonitrile with an excess of 6M solution of HCl in dioxane followed by removal of volatiles under reduced pressure and washing of the residue with Et₂O.

Example 37: Synthesis of N-(4-{[2-(dimethylamino)ethyl]carbamoyl}benzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 8)

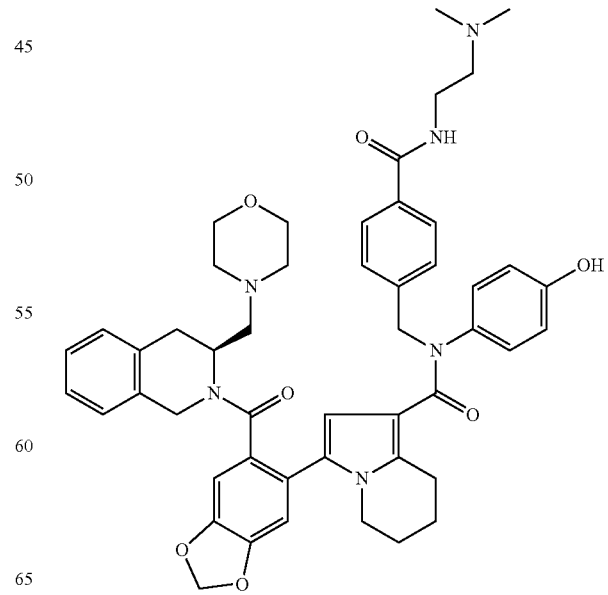

The procedure was as in the process of Example 33 using 2-(dimethylamino)ethyl amine instead of ammonium chloride at Step A.

Example 38: Synthesis of N-(4-hydroxyphenyl)-N-{4-[(4-methylpiperazin-1-yl)carbonyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 12)

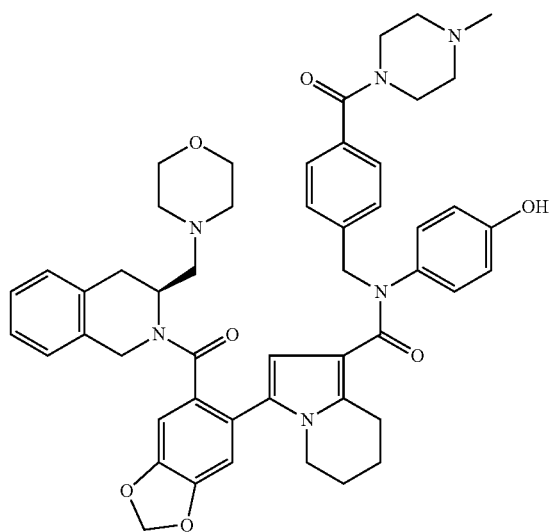 [SMILES: CN1CCN(C(=O)c2ccc(CN(C(=O)c3cc(-c4cc5c(cc4C(=O)N4Cc6ccccc6C[C@H]4CN4CCOCC4)OCO5)n4c3CCCC4)c3ccc(O)cc3)cc2)CC1]

The procedure was as in the process of Example 33 using N-methylpiperazine instead of ammonium chloride at Step A.

Example 39: Synthesis of 4-[(3-carbamoylbenzyl){[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino]phenyl acetate (Compound 41)

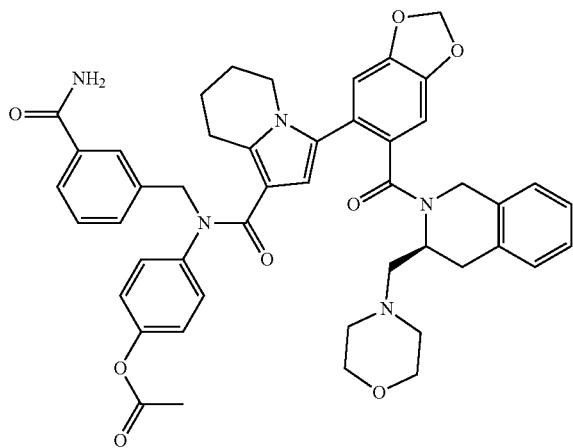 [SMILES: CC(=O)Oc1ccc(N(Cc2cccc(C(N)=O)c2)C(=O)c2cc(-c3cc4c(cc3C(=O)N3Cc5ccccc5C[C@H]3CN3CCOCC3)OCO4)n3c2CCCC3)cc1]

A mixture of N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See Example 28) (60 mg, 0.08 mmol), acetyl chloride (13 mg, 0.16 mmol) and Et₃N (32 mg, 0.3 mmol), and in CH₂Cl₂ (1 mL) was stirred for one hour at ambient temperature, washed with water, brine, dried over Na₂SO₄, and concentrated under reduced pressure. The residue was subjected to silica flash chromatography using mixture of CH₃OH (1 to 20%) and CH₂Cl₂ as an eluent to afford 6 mg (10%) of the title compound.

Example 40: Synthesis of N-(3-carbamoylbenzyl)-N-(4-ethoxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 42)

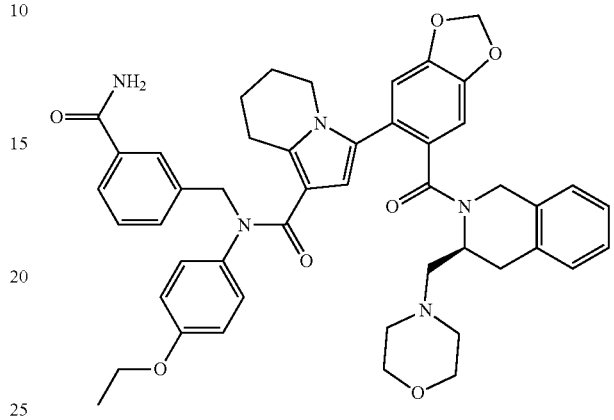

A mixture of N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (See Example 28) (0.06 mg, 0.08 mmol), iodoethane (24 mg, 0.16 mmol), Cs₂CO₃ (77 mg, 0.23 mmol), and DMF (0.1 mL) was stirred overnight at 60° C. Water was added to the reaction mixture, the precipitated product was separated by centrifugation, washed twice with water, and dried by lyophilization to afford 30 mg (48%) of the title compound.

Example 41: Synthesis of N-(4-hydroxyphenyl)-N-{3-[(methylsulfonyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide (Compound 43)

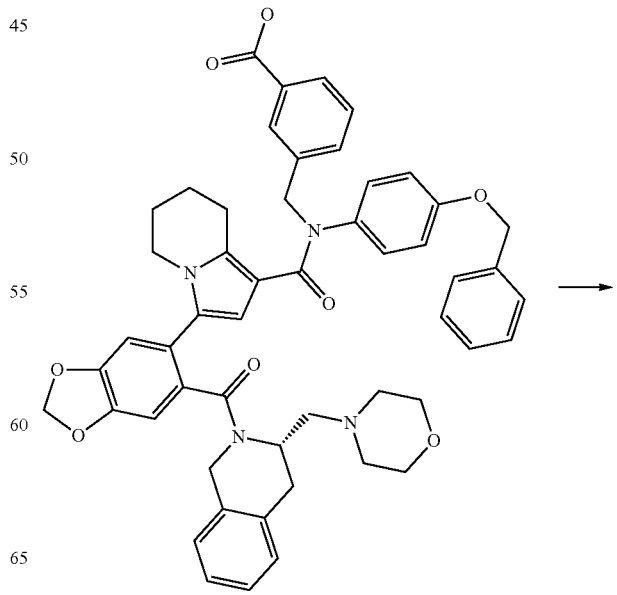

-continued

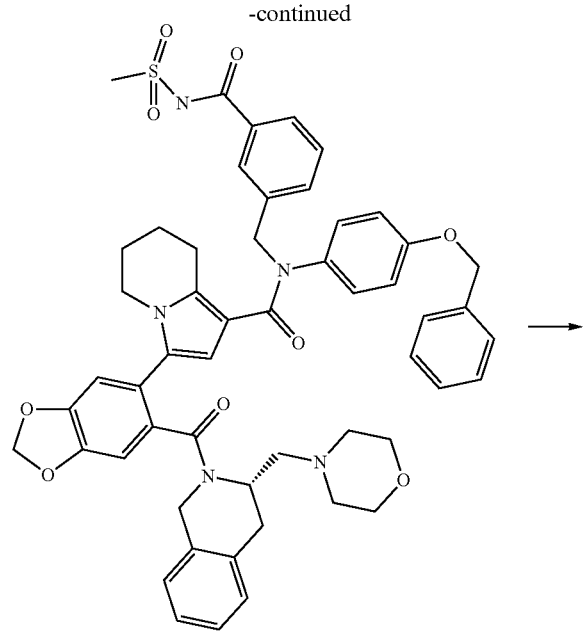

Step A: Synthesis of N-[4-(benzyloxy)phenyl]-N-{3-[(methyl sulfonyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide A mixture of 3-[([4-(benzyloxy)phenyl]{[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino)methyl]benzoic acid (See Preparation 8) (100 mg, 0.12 mmol), Et$_3$N (24 mg 0.23 mmol), EDCI (67 mg, 0.35 mmol), DMAP (26 mg, 0.23 mmol), and DMF (1 mL) was stirred at ambient temperature for 30 min, then methanesulfonamide (33 mg, 0.35 mmol) was added. The reaction mixture was stirred at ambient temperature for 12 h and then partitioned between EtOAc and water. The organic layer was separated, washed with brine, dried over Na$_2$SO$_4$, filtered, concentrated under reduced pressure. The residue was subjected to silica flash chromatography eluting with a mixture of EtOAc (0 to 100%) and CH$_2$Cl$_2$ to afford 80 mg (73%) of the title compound.

Step B: Synthesis of N-(4-hydroxyphenyl)-N-{3-[(methyl sulfonyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide A stirred mixture of the compound obtained at Step A, catalyst (10 mg of 5% Pd on charcoal), and methanol (2 mL) was hydrogenated under H$_2$ atmosphere for 2 h. The catalyst was filtered off, and the filtrate was evaporated to dryness. The residue was subjected to HPLC purification to afford 60 mg (83%) of the title compound.

Example 42: Compounds 44-50

Using procedures described herein directly or with slightly modification and appropriate reagents and intermediates were obtained compounds No. 44-52. Table A1.

Compound 44. 4-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic Acid

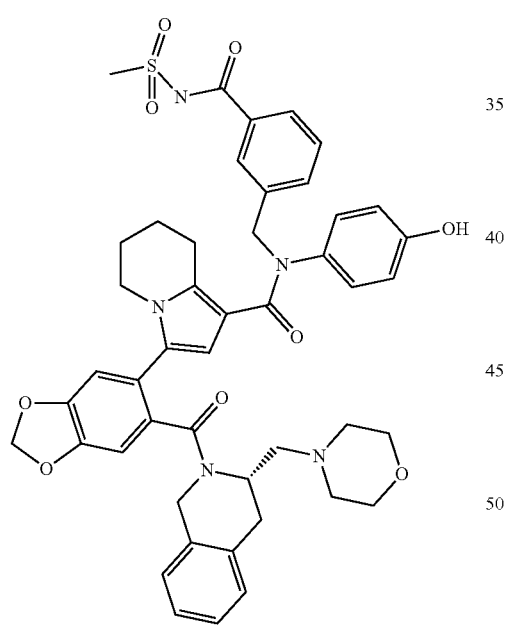

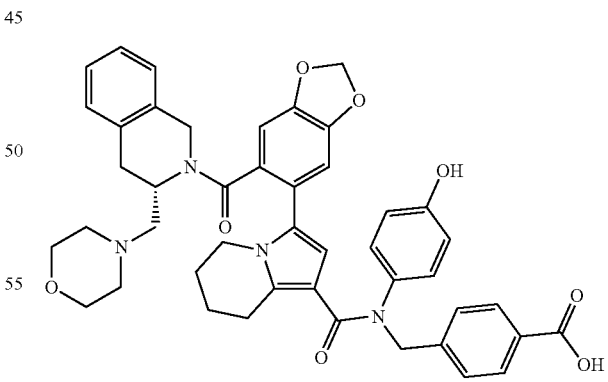

$^1$H NMR (400 MHz, DMSO-d$_6$), δ: 9.45-9.28 (s, 2H), 7.95-7.76 (d, J=8.0 Hz, 2H), 7.37-7.27 (d, J=8.1 Hz, 2H), 7.25-7.08 (m, 3H), 7.08-6.93 (m, 3H), 6.88-6.76 (s, 1H), 6.66-6.37 (m, 4H), 6.17-5.97 (m, 2H), 5.24-4.72 (m, 4H), 4.46-4.10 (m, 2H), 4.08-3.91 (s, 2H), 3.80-3.61 (s, 5H), 3.29-2.73 (m, 8H), 1.86-1.29 (m, 4H).

Compound 45. 3-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic Acid

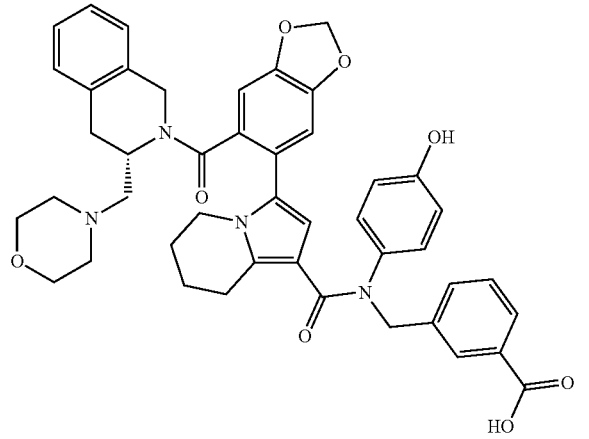 [SMILES: O=C(O)c1cccc(CN(C(=O)c2cc(-c3cc4c(cc3C(=O)N3Cc5ccccc5C[C@H]3CN3CCOCC3)OCO4)n3c2CCCC3)c2ccc(O)cc2)c1]

$^1$H NMR (400 MHz, DMSO-d$_6$), δ: 9.92-9.18 (m, 1H), 7.98-7.74 (m, 2H), 7.49-7.34 (m, 2H), 7.31-7.11 (m, 3H), 7.07-6.94 (m, 3H), 6.89-6.72 (s, 2H), 6.68-6.43 (m, 4H), 6.24-5.98 (m, 2H), 5.23-4.69 (m, 4H), 4.45-4.08 (m, 2H), 4.06-3.91 (m, 2H), 3.80-3.30 (m, 6H), 3.29-2.75 (m, 7H), 1.88-1.26 (m, 4H).

Compound 46. tert-Butyl 3-[(4-hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoate

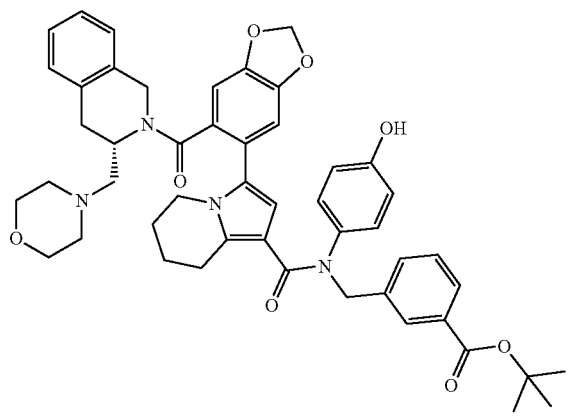 [SMILES: CC(C)(C)OC(=O)c1cccc(CN(C(=O)c2cc(-c3cc4c(cc3C(=O)N3Cc5ccccc5C[C@H]3CN3CCOCC3)OCO4)n3c2CCCC3)c2ccc(O)cc2)c1]

$^1$H NMR (400 MHz, DMSO-d$_6$), δ: 9.49-9.25 (m, 1H), 7.87-7.58 (m, 2H), 7.58-7.24 (m, 2H), 7.24-7.07 (m, 3H), 7.07-6.51 (m, 6H), 6.51-6.23 (m, 2H), 6.16-5.91 (m, 2H), 5.20-4.62 (m, 4H), 4.28-3.83 (m, 2H), 3.71-3.40 (m, 6H), 3.09-2.77 (m, 3H), 2.35-2.19 (m, 3H), 2.20-1.63 (m, 7H), 1.63-1.34 (s, 9H).

Compound 47. N-[(2-Cyanophenyl)methyl]-N-(4-hydroxyphenyl)-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide

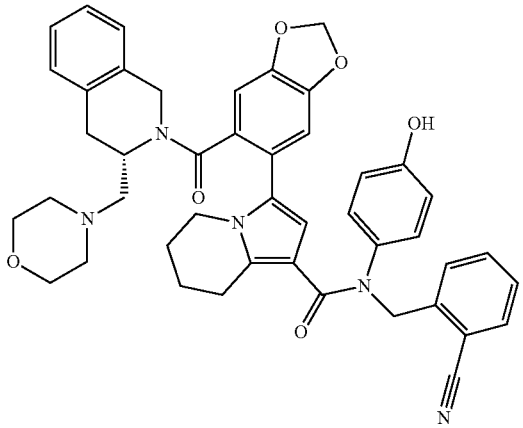 [SMILES: N#Cc1ccccc1CN(C(=O)c1cc(-c2cc3c(cc2C(=O)N2Cc4ccccc4C[C@H]2CN2CCOCC2)OCO3)n2c1CCCC2)c1ccc(O)cc1]

$^1$H NMR (400 MHz, DMSO-d$_6$), δ: 9.58-9.30 (m, 1H), 7.95-7.26 (m, 5H), 7.26-6.94 (m, 4H), 6.94-6.65 (m, 3H), 6.65-6.50 (t, J=8.2 Hz, 1H), 6.50-6.24 (m, 2H), 6.20-6.02 (m, 2H), 5.32-4.55 (m, 4H), 4.31-3.78 (m, 2H), 3.72-3.42 (m, 5H), 3.15-2.71 (m, 3H), 2.73-2.60 (m, 1H), 2.35-2.21 (m, 2H), 2.21-1.36 (m, 8H).

Compound 48. N-(4-Hydroxyphenyl)-N-[(4-methyl-1,2,4-triazol-3-yl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide

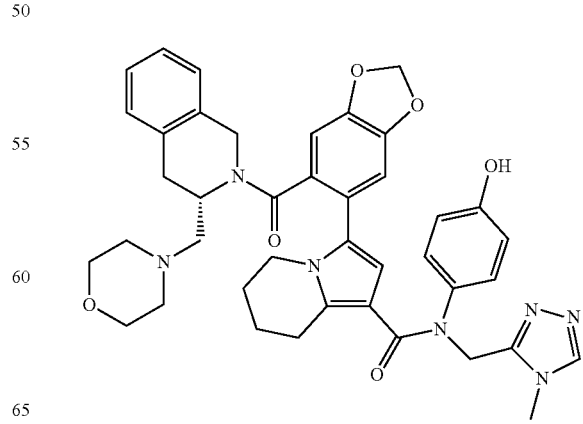

$^1$H NMR (400 MHz, DMSO-d$_6$), δ: 9.65-9.28 (m, 1H), 8.55-8.21 (m, 2H), 7.32-6.95 (m, 3H), 6.95-6.69 (m, 3H), 6.69-6.48 (m, 2H), 6.48-6.23 (s, 2H), 6.14-6.01 (m, 2H), 5.23-4.65 (m, 4H), 4.65-4.45 (m, 2H), 4.28-3.84 (m, 2H), 3.76-3.39 (m, 11H), 3.12-2.76 (m, 2H), 2.34-2.20 (m, 2H), 2.20-1.34 (m, 5H).

Compound 49. N-(4-Hydroxyphenyl)-3-[6-[(3S)-3-(morpholinomethyl)-3,4-dihydro-1H-isoquinoline-2-carbonyl]-1,3-benzodioxol-5-yl]-N-[(3-nitrophenyl)methyl]-5,6,7,8-tetrahydroindolizine-1-carboxamide

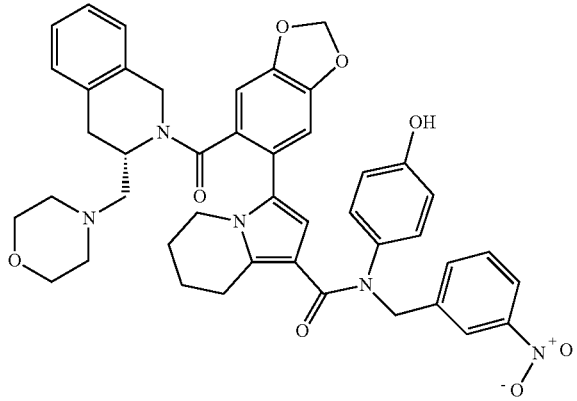

$^1$H NMR (400 MHz, DMSO-d$_6$), δ: 9.60-9.22 (m, 1H), 8.21-7.94 (m, 2H), 7.72-7.45 (m, 2H), 7.24-7.06 (m, 3H), 7.06-6.50 (m, 6H), 6.50-6.30 (m, 2H), 6.21-5.97 (m, 2H), 5.20-4.66 (m, 4H), 4.29-3.78 (m, 2H), 3.70-3.36 (m, 8H), 3.11-2.77 (m, 3H), 2.37-2.20 (m, 2H), 2.20-1.27 (m, 6H).

Compound 50. N-(4-Hydroxyphenyl)-N-[(2-methyl-3-nitro-phenyl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide

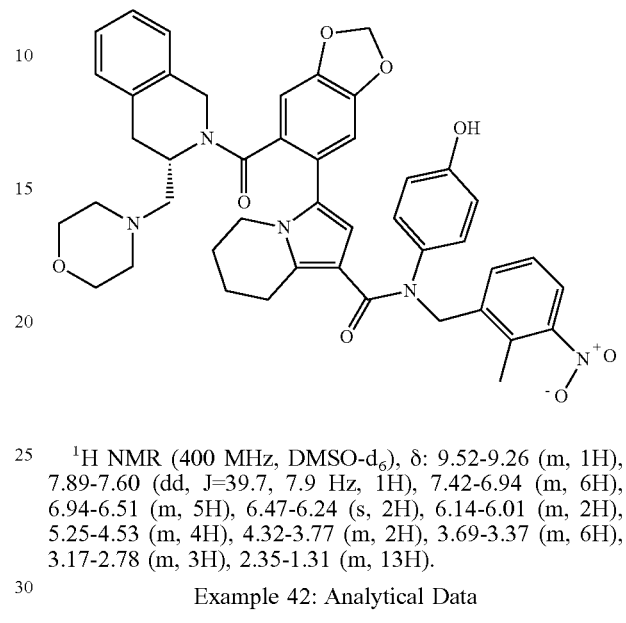

$^1$H NMR (400 MHz, DMSO-d$_6$), δ: 9.52-9.26 (m, 1H), 7.89-7.60 (dd, J=39.7, 7.9 Hz, 1H), 7.42-6.94 (m, 6H), 6.94-6.51 (m, 5H), 6.47-6.24 (s, 2H), 6.14-6.01 (m, 2H), 5.25-4.53 (m, 4H), 4.32-3.77 (m, 2H), 3.69-3.37 (m, 6H), 3.17-2.78 (m, 3H), 2.35-1.31 (m, 13H).

Example 42: Analytical Data

Preparative HPLC

Neutral conditions are as follows: YMC-Pack ODS-AQ 250×20 mm, S-10 μm, pore size 12 nm, gradient water-acetonitrile.

Standard, acidic, conditions are as follows: YMC-Pack ODS-AQ 250×20 mm, S-10 μm, pore size 12 nm, gradient A solution-B solution; A: 1000 ml water-226 μl trifluoroacetic acid, B: 1000 ml CH$_3$CN-226 μl trifluoroacetic acid.

Analytical Data, LCMS Conditions:

C18 column 100×4.6 mm, 5.0 μm, pore size 100 Å, water-acetonitrile+0.1% trifluoroacetic acid, gradient 5 to 87% for 10 min,

TABLE A

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 15 | 01 | N-benzyl-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 724.9 | 5.26 | 725 | 725 | 97 | 98 |
| 4 | 02 | N-(4-hydroxyphenyl)-N-(2-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 738.9 | 5.29 | 739 | 739 | 96 | 99 |

TABLE A-continued

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 14 | 03 | N-(4-hydroxyphenyl)-N-(3-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 738.9 | 5.34 | 739 | 739 | 97 | 100 |
| 20 | 04 | N-(4-hydroxyphenyl)-N-(4-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 738.9 | 5.36 | 739 | 739 | 97 | |
| 11 | 05 | N-(2-fluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 742.9 | 5.20 | 783 | 783 | 99 | 98 |
| 21 | 06 | N-(3-fluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 742.9 | 5.26 | 783 | 783 | 100 | |
| 17 | 07 | N-(4-fluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamid | 742.9 | 5.26 | 783 | 783 | 91 | 90 |
| 30 | 08 | N-(2,6-dimethylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 752.9 | 5.95 | 753 | 753 | 99 | 99 |
| 31 | 09 | N-(4-hydroxyphenyl)-N-(2-methoxybenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 754.9 | 5.71 | 755 | 755 | 96 | 95 |
| 32 | 10 | N-(2-fluoro-6-methylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 756.9 | 5.83 | 757 | 757 | 98 | 99 |

TABLE A-continued

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 33 | 11 | N-(2-chlorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 759.3 | 5.92 | 760 | 760 | 97 | |
| 19 | 12 | N-(2,6-difluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 760.8 | 5.69 | 761 | 761 | 98 | 100 |
| 3 | 13 | N-(4-hydroxyphenyl)-N-(3-methoxy-2-methylbenzyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 768.9 | 5.88 | 769 | 769 | 97 | 98 |
| 34 | 14 | N-(2-chloro-6-methylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 773.3 | 6.01 | 774 | 774 | 96 | 99 |
| 5 | 15 | N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[2-(trifluoromethyl)benzyl]-5,6,7,8-tetrahydroindolizine-1-carboxamide | 792.9 | 5.51 | 793 | 793 | 97 | |
| 16 | 16 | N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[3-(trifluoromethyl)benzyl]-5,6,7,8-tetrahydroindolizine-1-carboxamide | 792.9 | 5.59 | 793 | 793 | 99 | |
| 24 | 17 | N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[4-(trifluoromethyl)benzyl]-5,6,7,8-tetrahydroindolizine-1-carboxamide | 792.9 | 5.65 | 793 | 793 | 98 | |
| 35 | 18 | N-(6-chloro-2,3-difluorobenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 795.3 | 6.08 | 796 | 796 | 96 | 96 |

TABLE A-continued

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 18 | 19 | N-(biphenyl-2-ylmethyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 801.0 | 6.38 | 801 | 801 | 90 | 91 |
| 37 | 20 | N-(4-hydroxyphenyl)-N-[2-methyl-4-(trifluoromethyl)benzyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 806.9 | 6.40 | 807 | 807 | 98 | 99 |
| 38 | 21 | N-(4-hydroxyphenyl)-N-[2-methyl-5-(trifluoromethyl)benzyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 806.9 | 6.34 | 807 | 807 | 93 | 92 |
| 26 | 22 | N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-[4-(trifluoromethoxy)benzyl]-5,6,7,8-tetrahydroindolizine-1-carboxamide | 808.9 | 5.70 | 809 | 809 | 98 | 97 |
| 22 | 23 | N-[2-fluoro-6-(trifluoromethyl)benzyl]-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 810.9 | 5.97 | 811 | 812 | 97 | 98 |
| 39 | 24 | N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-(pyridin-3-ylmethyl)-5,6,7,8-tetrahydroindolizine-1-carboxamide | 725.8 | 3.57 | 726 | 726 | 98 | |
| 9 | 25 | N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-N-(pyridin-4-ylmethyl)-5,6,7,8-tetrahydroindolizine-1-carboxamide | 725.8 | 4.17 | 726 | 726 | 91 | |

TABLE A-continued

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 23 | 26 | N-(4-hydroxyphenyl)-N-[(4-methoxy-3,5-dimethylpyridin-2-yl)methyl]-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 783.9 | 3.86 | 784 | 784 | 98 | |
| 27 | 27 | N-{[2-(4-ethoxyphenyl)-5-methyl-1,3-oxazol-4-yl]methyl}-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 850.0 | 5.67 | 850 | 850 | 98 | 97 |
| 7 | 28 | N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 767.9 | 4.54 | 768 | 768 | 99 | 99 |
| 7 HCl salt | 29 | N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride | 767.9 | 4.50 | 768 | 768 | 99 | 99 |
| 2 | 30 | N-(4-hydroxyphenyl)-N-{3-[(2-methoxy-ethyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 826.0 | 5.09 | 826 | 826 | 97 | 98 |
| 6 | 31 | N-(3-{[2-(dimethylamino)ethyl]carbamoyl}benzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 839.0 | 4.26 | 839 | 839 | 96 | 96 |
| 10 | 32 | N-(4-hydroxyphenyl)-N-{3-[(4-methylpiperazin-1-yl)carbonyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 851.0 | 4.27 | 851 | 851 | 95 | 96 |

TABLE A-continued

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 13 | 33 | N-(4-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 767.9 | 4.90 | 768 | 768 | 96 | 97 |
| 13 HCl salt | 34 | N-(4-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride | 767.9 | 4.62 | 768 | 768 | 100 | 100 |
| 1 | 35 | N-(4-hydroxyphenyl)-N-{4-[(2-methoxy-ethyl)carbamoyl]benzyl}-3-(6-{(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 826.0 | 5.10 | 826 | 826 | 96 | 96 |
| 1 HCl salt | 36 | N-(4-hydroxyphenyl)-N-{4-[(2-methoxy-ethyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride | 826.0 | 4.70 | 826 | 826 | 95 | 100 |
| 8 | 37 | N-(4-{[2-(dimethylamino)ethyl]carbamoyl}benzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 839.0 | 4.24 | 839 | 839 | 97 | |
| 12 | 38 | N-(4-hydroxyphenyl)-N-{4-[(4-methylpiperazin-1-yl)carbonyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 851.0 | 4.20 | 851 | 851 | 99 | |
| 41 | 39 | 4-[(3-carbamoylbenzyl){[3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizin-1-yl]carbonyl}amino]phenyl acetate | 809.9 | 4.79 | 810 | 810 | 100 | 99 |

TABLE A-continued

Analytical data.

| Cmpd No. | Example No. | Name | MW | RT, min | MS (ESI) [M + H] + cltd | MS (ESI) [M + H] + msrd | Purity (%) 220 nm | Purity (%) 254 nm |
|---|---|---|---|---|---|---|---|---|
| 42 | 40 | N-(3-carbamoylbenzyl)-N-(4-ethoxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 795.9 | 5.13 | 796 | 796 | 96 | 97 |
| 43 | 41 | N-(4-hydroxyphenyl)-N-{3-[(methylsulfonyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide | 846.0 | 5.33 | 846 | 846 | 96 | 96 |

Example 44: Primary PPI Inhibition Assays

BCL-2 TR-FRET Assay (BPS Bioscience, #50222)

The following assay concentrations and times were used: 3 ng BCL-2, 5 μl of 1:100 anti-His Tb-labeled donor, 5 μl of 1:100 Dye-labeled acceptor, 5 μl of 1:40 BCL-2 Peptide Ligand, and 2 ul of test compound, with 60 min incubation time. The results of the assay were read using a Clariostar (BMG Labtech) plate reader with the following parameters: TR FRET, 340ex/620 and 665em; 60 μsec Delay; and 500 μsec integration.

BCL-XL TR-FRET Assay (BPS Bioscience, #50223)

The following assay concentrations and times were used: 10.5 ng BCL-XL, 5 μl of 1:100 anti-His Tb-labeled donor, 5 μl of 1:100 Dye-labeled acceptor, 5 μl of 1:80 BCL-XL Peptide Ligand, and 2 μl of test compound, with 60 min incubation time. The results of the assay were read using a Clariostar (BMG Labtech) plate reader with the following parameters: TR FRET, 340ex/620 and 665em; 60 μsec Delay; and 500 μsec integration.

MCL-1 TR-FRET Assay (BPS Bioscience, #79506)

The following assay concentrations and times were used: 10 ng MCL-1, 5 μl of 1:200 anti-His Tb-labeled donor, 5 μl of 1:200 Dye-labeled acceptor, 5 μl of 1:10 MCL-1 Peptide Ligand, and 2 μl of test compound, with 60 min incubation time. The results of the assay were read using a Clariostar (BMG Labtech) plate reader with the following parameters: TR FRET, 340ex/620 and 665em; 60 μsec Delay; and 500 μsec integration.

Table B assigns a code for potency for BCL-2 TR-FRET Assay: A, B, C, or D. According to the code, A represents an $IC_{50}$ value ≤5 nM; B represents $IC_{50}$>5 nM and ≤10 nM; C represents $IC_{50}$>10 nM and ≤50 nM D represents $IC_{50}$>50 nM.

Table B assigns a code for potency for BCL-XL TR-FRET Assay: A, B, or C. According to the code, A represents $IC_{50}$ value ≤2,000 nM; B represents $IC_{50}$ values >2,000 nM and ≤4,000 nM; C represents $IC_{50}$ values >4,000 nM.

TABLE B

Primary PPI inhibition

| Cmpd. No. | Example No. | BCL2 | BCLxL | MCL1 $IC_{50}$ (μM) |
|---|---|---|---|---|
| 15 | 1 | B | A | — |
| 4 | 2 | A | A | — |
| 14 | 3 | B | B | — |
| 20 | 4 | B | B | — |
| 11 | 5 | A | A | — |
| 21 | 6 | C | B | — |
| 17 | 7 | C | C | — |
| 30 | 8 | D | — | — |
| 31 | 9 | A | A | — |
| 32 | 10 | C | — | — |
| 33 | 11 | A | A | — |
| 19 | 12 | B | C | — |
| 3 | 13 | A | A | — |
| 34 | 14 | D | C | — |
| 5 | 15 | A | A | — |
| 16 | 16 | C | C | — |
| 24 | 17 | C | C | — |
| 35 | 18 | C | C | 4- |
| 18 | 19 | C | A | — |
| 37 | 20 | B | — | — |
| 38 | 21 | C | — | — |
| 26 | 22 | D | C | — |
| 22 | 23 | D | C | — |
| 39 | 24 | B | B | — |
| 9 | 25 | A | B | — |
| 23 | 26 | C | C | — |
| 27 | 27 | D | C | — |
| 7 | 28 | A | A | >100 |
| 2 | 30 | A | — | >100 |
| 6 | 31 | A | — | >100 |
| 10 | 32 | B | — | >100 |
| 13 | 33 | B | A | >100 |
| 1 | 35 | A | A | >100 |
| 8 | 37 | A | A | >100 |
| 12 | 38 | B | A | >100 |
| 43 | 41 | B | B | — |
| 45 | 42 | C | B | — |
| 46 | 42 | C | — | — |
| 47 | 42 | D | — | — |
| 48 | 42 | A | A | — |
| 49 | 42 | D | C | — |
| 50 | 42 | D | C | — |

Example 44: Cell Viability Assays (Cell Lines HEK293, RS4-11, MOLT-4)

Culture medium for HEK293—DMEM (PanEco, Cat #C420) was used. RPMI-1640 (PanEco, Cat #C363) was used for the rest of the cell lines.

Compounds were prepared as 200× stocks with serial dilution in 100% DMSO with a final concentration of 1×.

Compound solutions were dispersed in 40 µL aliquots in 384-well plates at a concentration of 2000 cells per well for HEK293 and at a concentration of 4000 cells per well for the rest of the cell lines using a robotic station Biomek (Beckman). Before adding compounds, the cells were incubated at 37° C. (HEK293 were incubated for a day before adding compounds).

A dilution plate was prepared by pouring 78 µL of the appropriate culture medium using a robotic station Biomek (Beckman). Sequentially, using a robotic station, 2 µL of substances were taken and added to 78 µL of culture medium (dilution of compounds 40×). 10 µL aliquots were taken and added to the plates of the cells (dilution of compounds 5×). The plates were incubated for 3 days at a temperature 37° C. After 3 days, 10 µL of CellTiter-Glo (Promega) was added to the cells and the luminescence was measured.

Table C assigns a code for potency for RS4-11 Assay: A, B, or C. According to the code, A represents an CC50 value ≤0.1 µM; B represents CC50>0.1 µM and ≤0.2 µM; C represents CC50>0.2 µM.

Table C assigns a code for potency for MOLT-4 Assay: A, B, or C. According to the code, A represents an CC50 value ≤2 µM; B represents CC50>2 µM and ≤10 µM; C represents CC50>10 µM.

Table C assigns a code for potency for HEK293 Assay: A, B, or C. According to the code, A represents an $CC_{50}$ value ≤10 µM; B represents $CC_{50}$>10 µM and ≤25 µM; C represents $CC_{50}$>25 µM.

TABLE C

Cellular models efficacy and cytotoxicity.

| Cmpd. No. | Example No. | RS4-11 | MOLT-4 | HEK293 |
|---|---|---|---|---|
| 15 | 1 | B | A | C |
| 4 | 2 | A | C | C |
| 14 | 3 | A | B | C |
| 20 | 4 | B | B | A |
| 11 | 5 | A | C | B |
| 21 | 6 | B | C | C |
| 17 | 7 | C | C | C |
| 31 | 9 | A | A | C |
| 33 | 11 | A | A | B |
| 19 | 12 | C | B | C |
| 3 | 13 | A | A | C |
| 34 | 14 | C | A | C |
| 5 | 15 | A | B | C |
| 16 | 16 | B | C | C |
| 24 | 17 | C | B | A |
| 35 | 18 | C | A | C |
| 18 | 19 | C | B | C |
| 37 | 20 | A | B | C |
| 39 | 24 | C | A | B |
| 9 | 25 | B | B | B |
| 23 | 26 | C | C | B |
| 7 | 28 | B | B | A |
| 2 | 30 | B | C | A |
| 6 | 31 | C | C | B |
| 10 | 32 | C | C | B |
| 13 | 33 | A | B | B |
| 1 | 35 | A | B | A |
| 8 | 37 | A | C | C |
| 12 | 38 | A | C | B |
| 45 | 42 | C | C | C |
| 48 | 42 | A | B | B |
| 49 | 42 | C | C | C |
| 50 | 42 | C | B | C |

Example 45: Caspase-3/7 Activation

Assay Principle:

The Caspase-Glo 3/7 Assay is homogeneous, luminescent assay that measures caspase-3 and -7 activities. The assay provides a luminogenic caspase-3/7 substrate, which contains the tetrapeptide sequence DEVD, in a reagent optimized for caspase activity.

Assay Procedure:

Incubate RS4-11 cells with varying concentrations of test compounds for 3.5 h in a humidified incubator at 37° C. and 5% $CO_2$ and 30 min at r.t. Add 15 µl Caspase-Glo reagent to each well and incubate the plate for 30 min at r.t. Read on ClarioStar Plus instrument.

Materials:

Promega Caspase-Glo (Promega, #8212); Frozen RS4-11 cells; 384-well white plate (Corning, #3570).

Instrumentation:

ClarioStar Plus; Biomek FX for liquid handling (Beckman Coulter).

Table D assigns a code for potency for Cas-3/7 Assay: A, B, or C. According to the code, A represents an $EC_{50}$ value ≤0.1 µM; B represents $EC_{50}$>0.1 µM and ≤0.25 µM; C represents $EC_{50}$>0.25 µM.

TABLE D

Caspase-3/7 activation.

| Cmpd. No. | Example No. | Cas-3/7 |
|---|---|---|
| 15 | 1 | B |
| 4 | 2 | A |
| 14 | 3 | C |
| 20 | 4 | C |
| 11 | 5 | A |
| 21 | 6 | C |
| 17 | 7 | C |
| 31 | 9 | A |
| 33 | 11 | A |
| 19 | 12 | C |
| 3 | 13 | A |
| 34 | 14 | C |
| 5 | 15 | A |
| 16 | 16 | B |
| 24 | 17 | C |
| 35 | 18 | C |
| 18 | 19 | C |
| 37 | 20 | B |
| 9 | 25 | B |
| 23 | 26 | C |
| 7 | 28 | B |
| 2 | 30 | C |
| 6 | 31 | C |
| 10 | 32 | C |
| 13 | 33 | A |
| 1 | 35 | A |
| 8 | 37 | A |
| 12 | 38 | A |
| 48 | 42 | A |
| 50 | 42 | C |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula (I):

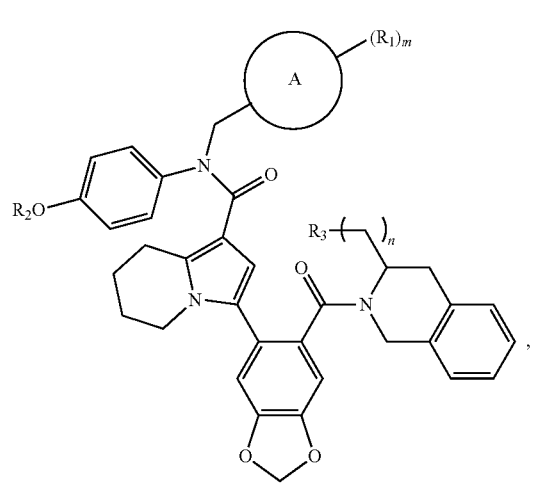

or a pharmaceutically acceptable salt, stereoisomer, solvate, or tautomer thereof,
wherein:
- Ring A is selected from aryl or heteroaryl;
- each $R_1$ is independently selected from halo, —OH, —CN, —NO$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, aryl, —C(O)OR$_4$, and —C(O)NR$_5$R$_6$, wherein aryl is optionally substituted with one or more $R_7$;
- $R_2$ is selected from H, $C_1$-$C_6$ alkyl, and —C(O)R$_4$;
- $R_3$ is selected from 3- to 8-membered heterocyclyl, —O(CH$_2$O)$_o$R$_8$, and —N(R$_9$)$_2$, wherein the heterocyclyl is optionally substituted with one or more $R_{10}$;
- each $R_4$ is independently selected from H and $C_1$-$C_6$ alkyl;
- each $R_5$ is independently selected from H, $C_1$-$C_6$ alkyl, —(CH$_2$)$_p$OR$_{11}$, —(CH$_2$)$_p$N(R$_{11}$)$_2$, and S(O)$_2$R$_{11}$;
- each $R_6$ is independently selected from H and $C_1$-$C_6$ alkyl, or $R_5$ and $R_6$, together with the atom to which they are attached, come together to form a 3- to 10-membered heterocyclyl ring further comprising 1, 2, or 3 heteroatoms selected from N, O, and S, wherein the heterocyclyl is optionally substituted with one or more $R_{11}$;
- each $R_7$ is independently selected from halo, —OH, —CN, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, and $C_1$-$C_6$ haloalkoxy;
- $R_8$ is selected from H, $C_1$-$C_6$ alkyl, $C_2$-$C_6$ alkenyl, $C_2$-$C_6$ alkynyl, and 3- to 8-membered heterocyclyl, wherein the heterocyclyl is optionally substituted with one or more $R_{10}$;
- each $R_9$ is independently selected from H, $C_1$-$C_6$ alkyl, $C_2$-$C_6$ alkenyl, and $C_2$-$C_6$ alkynyl;
- each $R_{10}$ is independently selected from $C_1$-$C_6$ alkyl, $C_2$-$C_6$ alkenyl, $C_2$-$C_6$ alkynyl, halo, and —OH;
- each $R_{11}$ is independently selected from H and $C_1$-$C_6$ alkyl;
- m is an integer selected from 0, 1, 2, 3, 4, and 5; and
- n is an integer selected from 0, 1, 2, 3, and 4;
- o is an integer selected from 0, 1, and 2; and
- p is an integer selected from 0, 1, 2, 3, 4, 5, and 6.

2. The compound of claim 1, wherein Formula (I) is Formula (I'):

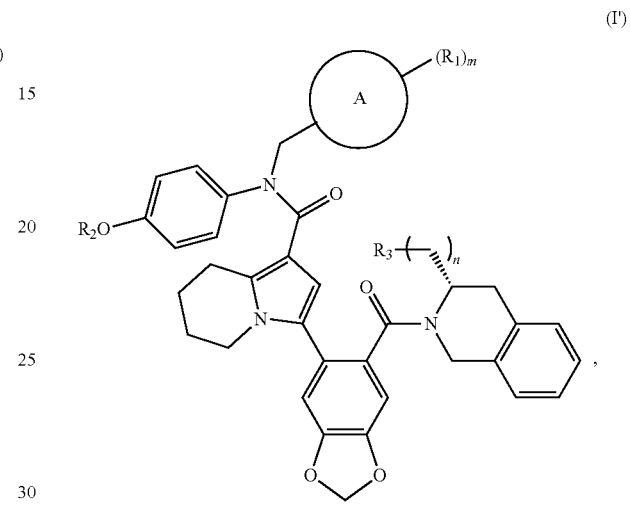

or a pharmaceutically acceptable salt, stereoisomer, solvate, or tautomer thereof.

3. The compound of claim 1, wherein Formula (I) is Formula (I-A):

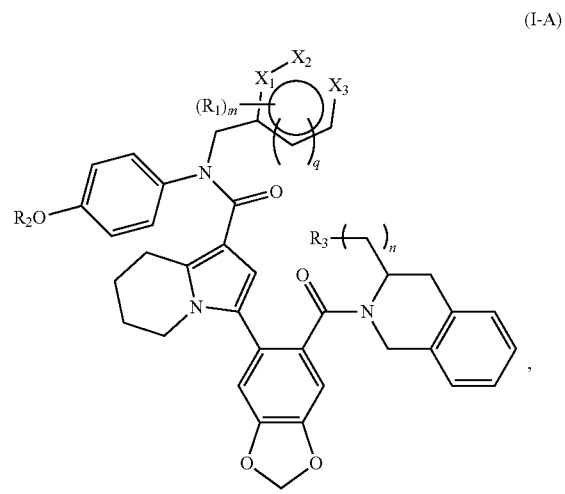

or a pharmaceutically acceptable salt, stereoisomer, solvate, or tautomer thereof,
wherein:
- $X_1$, $X_2$, and $X_3$ are each independently selected from CH, CR$_1$, N, NH, NR$_1$, and O; and
- q is an integer selected from 0 and 1; and
- wherein when any one of $X_1$, $X_2$, and $X_3$ is NH, NR$_1$ or O, then q is 0.

4. The compound of claim 1, wherein Formula (I) is Formula (I-B):

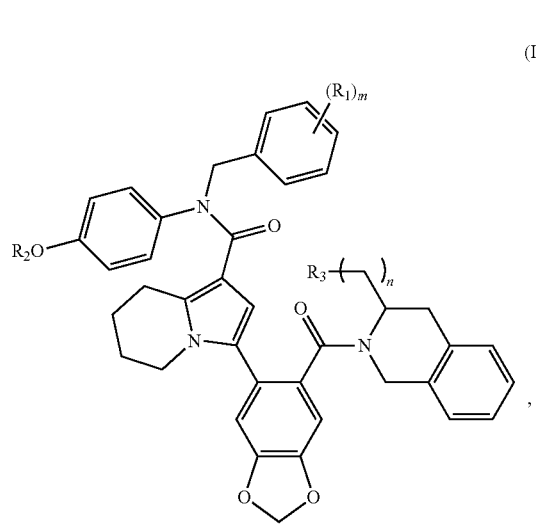

(I-B)

or a pharmaceutically acceptable salt, stereoisomer, solvate, or tautomer thereof.

5. The compound of claim 1, wherein Formula (I) is Formula (I-B-1):

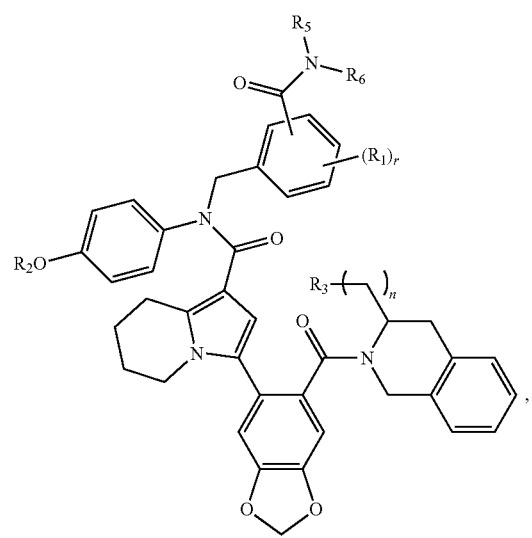

(I-B-1)

or a pharmaceutically acceptable salt, stereoisomer, solvate, or tautomer thereof;

wherein r is an integer selected from 0, 1, 2, 3, and 4.

6. The compound of claim 1, wherein Formula (I) is Formula (I-C-1), (I-C-2), or (I-C-3):

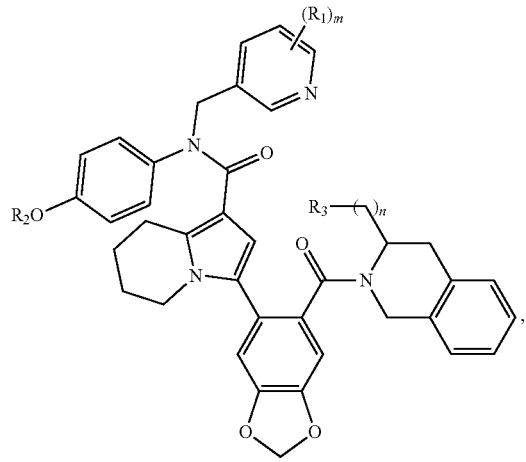

(I-C-1)

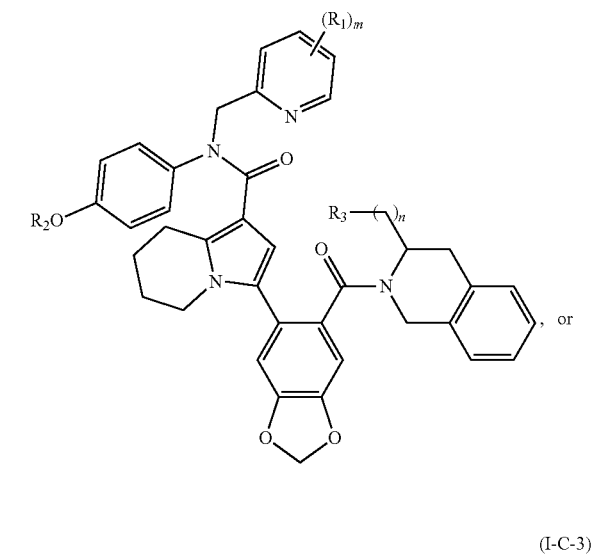

(I-C-2)

, or (I-C-3)

or a pharmaceutically acceptable salt, stereoisomer, solvate, or tautomer thereof.

7. The compound of claim 1, wherein Formula (I) is Formula (I-D):

(I-D)

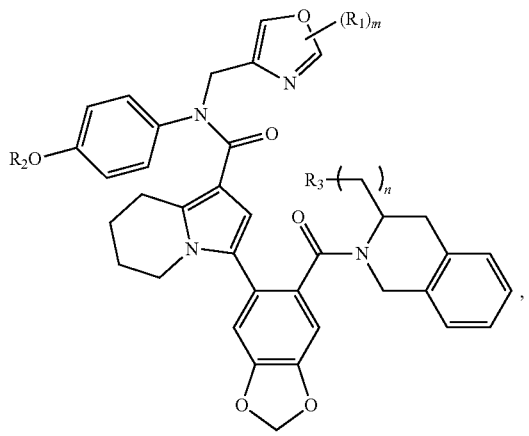

or a pharmaceutically acceptable salt, stereoisomer, solvate, or tautomer thereof.

8. The compound of claim 1, wherein Formula (I) is Formula (I-E):

(I-E)

or a pharmaceutically acceptable salt, stereoisomer, solvate, or tautomer thereof.

9. The compound of claim 1, wherein Ring A is phenyl.

10. The compound of claim 1, wherein Ring A is pyridinyl.

11. The compound of claim 1, wherein Ring A is 5-membered heteroaryl.

12. The compound of claim 1, wherein Ring A is 5-membered heteroaryl containing at least one N atom.

13. The compound of claim 1, wherein Ring A is 5-membered heteroaryl containing at least one O atom.

14. The compound of claim 1, wherein Ring A is selected from

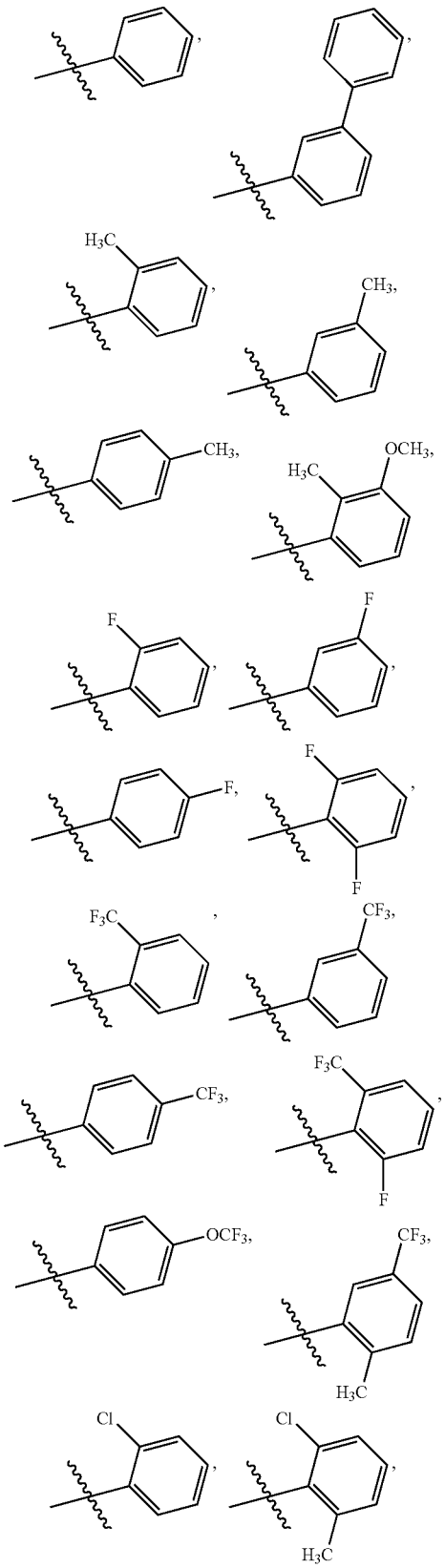

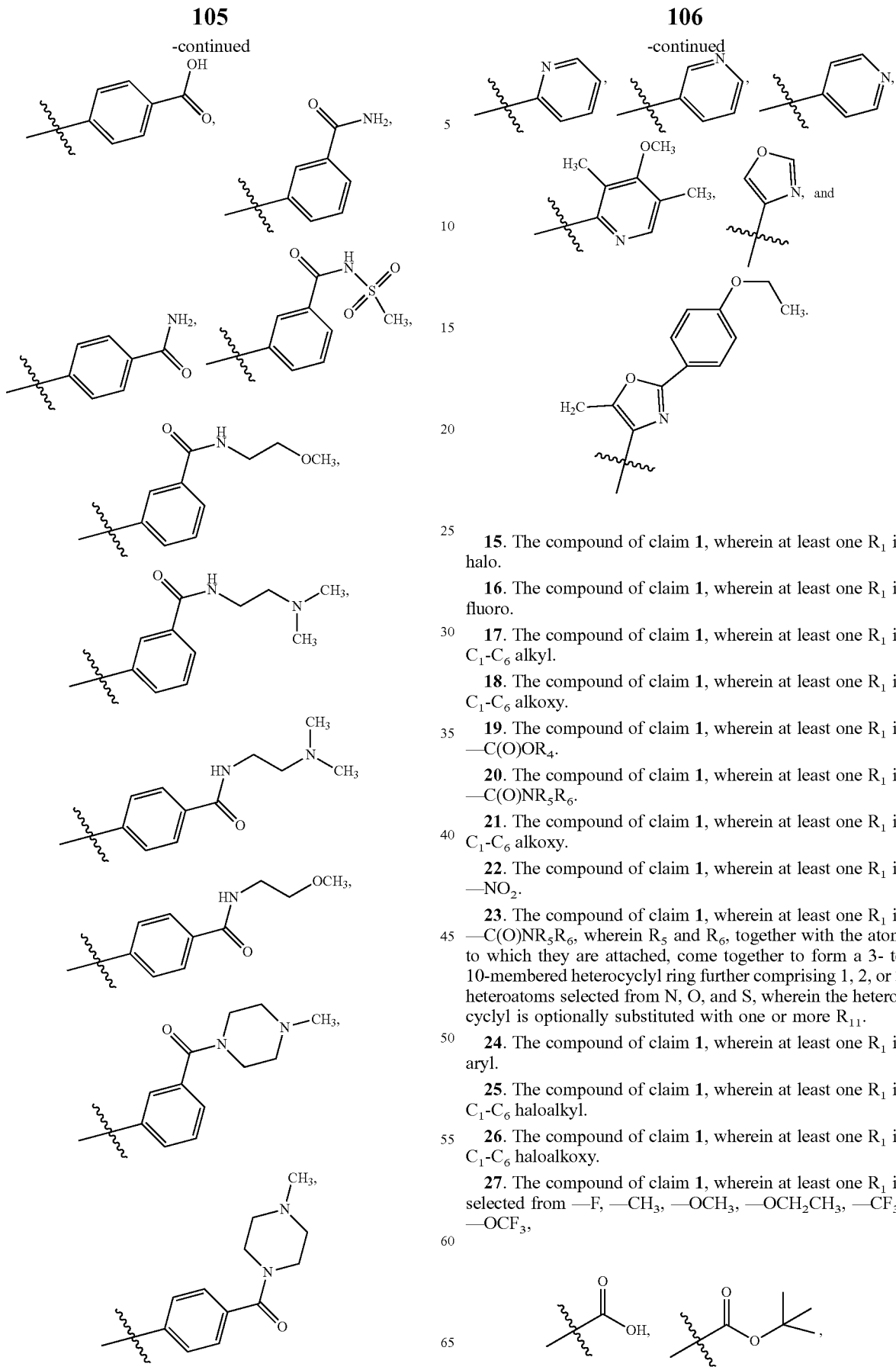

15. The compound of claim 1, wherein at least one $R_1$ is halo.

16. The compound of claim 1, wherein at least one $R_1$ is fluoro.

17. The compound of claim 1, wherein at least one $R_1$ is $C_1$-$C_6$ alkyl.

18. The compound of claim 1, wherein at least one $R_1$ is $C_1$-$C_6$ alkoxy.

19. The compound of claim 1, wherein at least one $R_1$ is —C(O)OR$_4$.

20. The compound of claim 1, wherein at least one $R_1$ is —C(O)NR$_5$R$_6$.

21. The compound of claim 1, wherein at least one $R_1$ is $C_1$-$C_6$ alkoxy.

22. The compound of claim 1, wherein at least one $R_1$ is —NO$_2$.

23. The compound of claim 1, wherein at least one $R_1$ is —C(O)NR$_5$R$_6$, wherein R$_5$ and R$_6$, together with the atom to which they are attached, come together to form a 3- to 10-membered heterocyclyl ring further comprising 1, 2, or 3 heteroatoms selected from N, O, and S, wherein the heterocyclyl is optionally substituted with one or more R$_{11}$.

24. The compound of claim 1, wherein at least one $R_1$ is aryl.

25. The compound of claim 1, wherein at least one $R_1$ is $C_1$-$C_6$ haloalkyl.

26. The compound of claim 1, wherein at least one $R_1$ is $C_1$-$C_6$ haloalkoxy.

27. The compound of claim 1, wherein at least one $R_1$ is selected from —F, —CH$_3$, —OCH$_3$, —OCH$_2$CH$_3$, —CF$_3$, —OCF$_3$,

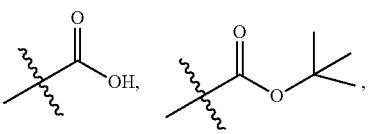

-continued

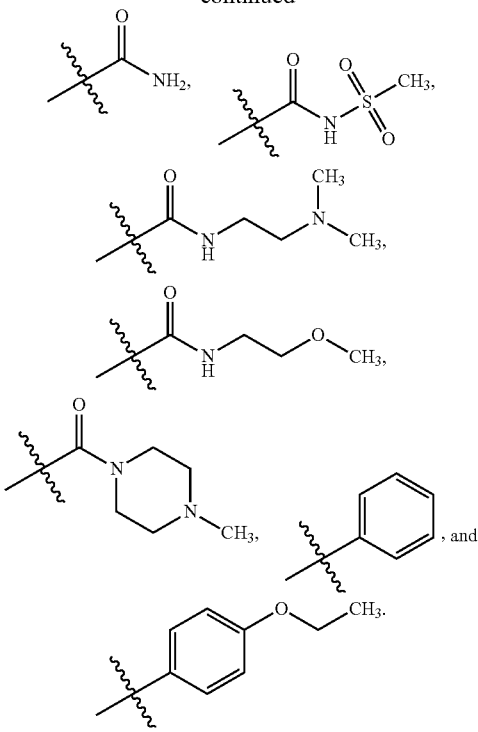

28. The compound of claim 1, wherein $R_2$ is H.
29. The compound of claim 1, wherein $R_2$ is $C_1$-$C_6$ alkyl.
30. The compound of claim 1, wherein $R_2$ is —C(O)$R_4$.
31. The compound of claim 1, wherein m is 0.
32. The compound of claim 1, wherein m is 1.
33. The compound of claim 1, wherein m is 2.
34. The compound of claim 1, wherein m is 3.
35. The compound of claim 1, wherein m is 2 or 3 and at least one $R_1$ is $C_1$-$C_6$ alkyl.
36. The compound of claim 1, wherein m is 2 and at least one $R_1$ is halo.
37. The compound of claim 1, wherein $R_3$ is 3- to 8-membered heterocyclyl.
38. The compound of claim 1, wherein $R_3$ is 6-membered heterocyclyl.
39. The compound of claim 1, wherein $R_3$ is —O(CH$_2$O)$_o$$R_8$.
40. The compound of claim 1, wherein $R_3$ is —N($R_9$)$_2$.
41. The compound of claim 1, wherein $R_3$ is selected from

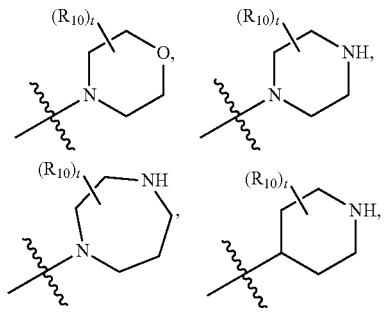

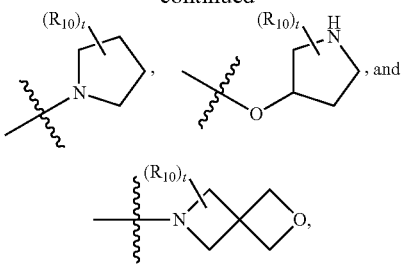

wherein t is 0, 1, 2, 3, or 4.

42. The compound of claim 1, wherein $R_3$ is selected from

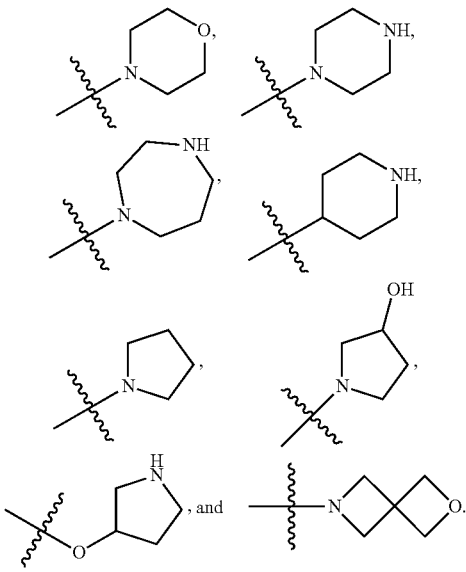

43. The compound of claim 42, wherein $R_3$ is

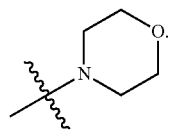 [SMILES: *N1CCOCC1]

44. The compound of claim 1, wherein n is 1.
45. The compound of claim 1, wherein n is 2.
46. The compound of claim 1, wherein n is 3.
47. The compound of claim 1, wherein $R_5$ is H.
48. The compound of claim 1, wherein $R_5$ is H and $R_6$ is H.
49. The compound of claim 1, wherein when $R_1$ is —C(O)NR$_5$R$_6$, $R_5$ is —(CH$_2$)$_p$OR$_{11}$ and $R_6$ is H.
50. The compound of claim 1, wherein when $R_1$ is —C(O)NR$_5$R$_6$, $R_5$ is —(CH$_2$)$_p$N(R$_{11}$)$_2$ and $R_6$ is H.
51. The compound of claim 1, wherein the compound is a pharmaceutically acceptable salt.
52. The compound of claim 1, wherein the compound is a hydrochloride salt.

53. A compound selected from:

| Compound No. | Compound Name |
|---|---|
| 1 | (S)-N-(4-hydroxyphenyl)-N-(4-((2-methoxyethyl)carbamoyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 2 | (S)-N-(4-hydroxyphenyl)-N-(3-((2-methoxyethyl)carbamoyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 3 | (S)-N-(4-hydroxyphenyl)-N-(3-methoxy-2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 4 | (S)-N-(4-hydroxyphenyl)-N-(2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 5 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(2-(trifluoromethyl)benzyl)-5,6,7,8-tetrahydroindolizine-1-carboxamide; |
| 6 | (S)-N-(3-((2-(dimethylamino)ethyl)carbamoyl)benzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 7 | (S)-N-(3-carbamoylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 8 | (S)-N-(4-((2-(dimethylamino)ethyl)carbamoyl)benzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 9 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(pyridin-4-ylmethyl)-5,6,7,8-tetrahydroindolizine-1-carboxamide; |
| 10 | (S)-N-(4-hydroxyphenyl)-N-(3-(4-methylpiperazine-1-carbonyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 11 | (S)-N-(2-fluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 12 | (S)-N-(4-hydroxyphenyl)-N-(4-(4-methylpiperazine-1-carbonyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 13 | (S)-N-(4-carbamoylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 14 | (S)-N-(4-hydroxyphenyl)-N-(3-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 15 | (S)-N-benzyl-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 16 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(3-(trifluoromethyl)benzyl)-5,6,7,8-tetrahydroindolizine-1-carboxamide; |
| 17 | (S)-N-(4-fluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 18 | (S)-N-([1,1'-biphenyl]-3-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 19 | (S)-N-(2,6-difluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 20 | (S)-N-(4-hydroxyphenyl)-N-(4-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 21 | (S)-N-(3-fluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 22 | (S)-N-(2-fluoro-6-(trifluoromethyl)benzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |

| Compound No. | Compound Name |
|---|---|
| 23 | (S)-N-(4-hydroxyphenyl)-N-((4-methoxy-3,5-dimethylpyridin-2-yl)methyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 24 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(4-(trifluoromethyl)benzyl)-5,6,7,8-tetrahydroindolizine-1-carboxamide; |
| 25 | (S)-4-((N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)methyl)benzoic acid; |
| 26 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(4-(trifluoromethoxy)benzyl)-5,6,7,8-tetrahydroindolizine-1-carboxamide; |
| 27 | (S)-N-((2-(4-ethoxyphenyl)-5-(13-methyl)oxazol-4-yl)methyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 28 | (S)-3-((N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)methyl)benzoic acid; |
| 29 | tert-butyl (S)-3-((N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)methyl)benzoate; |
| 30 | (S)-N-(2,6-dimethylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 31 | (S)-N-(4-hydroxyphenyl)-N-(2-methoxybenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 32 | (S)-N-(2-fluoro-6-methylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 33 | (S)-N-(2-chlorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 34 | (S)-N-(2-chloro-6-methylbenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 35 | (S)-N-(6-chloro-2,3-difluorobenzyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 36 | (S)-N-([1,1'-biphenyl]-2-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 37 | (S)-N-(4-hydroxyphenyl)-N-(2-methyl-4-(trifluoromethyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 38 | (S)-N-(4-hydroxyphenyl)-N-(2-methyl-5-(trifluoromethyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 39 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(pyridin-3-ylmethyl)-5,6,7,8-tetrahydroindolizine-1-carboxamide; |
| 40 | (S)-N-((2-(4-ethoxyphenyl)-5-methyloxazol-4-yl)methyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 41 | (S)-4-(N-(3-carbamoylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamido)phenyl acetate; |
| 42 | (S)-N-(3-carbamoylbenzyl)-N-(4-ethoxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 43 | (S)-N-(4-hydroxyphenyl)-N-(3-((methylsulfonyl)carbamoyl)benzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 44 | 4-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic acid |

| Compound No. | Compound Name |
|---|---|
| 45 | 3-[(4-Hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoic acid |
| 46 | tert-Butyl 3-[(4-hydroxy-N-[3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carbonyl]anilino)methyl]benzoate |
| 47 | N-[(2-Cyanophenyl)methyl]-N-(4-hydroxyphenyl)-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide |
| 48 | N-(4-Hydroxyphenyl)-N-[(4-methyl-1,2,4-triazol-3-yl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide |
| 49 | N-(4-Hydroxyphenyl)-3-[6-[(3S)-3-(morpholinomethyl)-3,4-dihydro-1H-isoquinoline-2-carbonyl]-1,3-benzodioxol-5-yl]-N-[(3-nitrophenyl)methyl]-5,6,7,8-tetrahydroindolizine-1-carboxamide |
| 50 | N-(4-Hydroxyphenyl)-N-[(2-methyl-3-nitro-phenyl)methyl]-3-[6-[(3S)-3-(morpholinomethyl)-3,4-dihydro-1H-isoquinoline-2-carbonyl]-1,3-benzodioxol-5-yl]-5,6,7,8-tetrahydroindolizine-1-carboxamide. | or a pharmaceutically acceptable salt, stereoisomer, solvate, or tautomer thereof.

54. A compound selected from:

| Compound No. | Compound Name |
|---|---|
| 1 HCl salt | N-(4-hydroxyphenyl)-N-{4-[(2-methoxyethyl)carbamoyl]benzyl}-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride; |
| 7 HCl salt | N-(3-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride; and |
| 13 HCl salt | N-(4-carbamoylbenzyl)-N-(4-hydroxyphenyl)-3-(6-{[(3S)-3-(morpholin-4-ylmethyl)-3,4-dihydroisoquinolin-2(1H)-yl]carbonyl}-1,3-benzodioxol-5-yl)-5,6,7,8-tetrahydroindolizine-1-carboxamide hydrochloride. |

55. The compound of claim 53, wherein the compound is selected from:

| Compound No. | Compound Name |
|---|---|
| 3 | (S)-N-(4-hydroxyphenyl)-N-(3-methoxy-2-methylbenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 5 | (S)-N-(4-hydroxyphenyl)-3-(6-(3-(morpholinomethyl)-1,2,3,4-tetrahydroisoquinoline-2-carbonyl)benzo[d][1,3]dioxol-5-yl)-N-(2-(trifluoromethyl)benzyl)-5,6,7,8-tetrahydroindolizine-1-carboxamide; |
| 18 | (S)-N-([1,1'-biphenyl]-3-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; |
| 31 | (S)-N-(4-hydroxyphenyl)-N-(2-methoxybenzyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; and |
| 36 | (S)-N-([1,1'-biphenyl]-2-ylmethyl)-N-(4-hydroxyphenyl)-3-(6-(3-(morpholinomethyl)-1,2,3,4-tetrahydroisoquinoline-2-carbonyl)benzo[d][1,3]dioxol-5-yl)-5,6,7,8-tetrahydroindolizine-1-carboxamide; | or a pharmaceutically acceptable salt, stereoisomer, solvate, or tautomer thereof.

56. A pharmaceutical composition comprising a compound according to claim 1, and a pharmaceutically acceptable carrier.

57. The pharmaceutical composition of claim 56, further comprising an additional pharmaceutically active agent.

58. A method of inhibiting a BCL-2 protein, comprising administering to a subject in need of a treatment for cancer a compound according to claim 1.

59. A method of treating cancer, comprising administering to a subject in need of a treatment for cancer a compound according to claim 1, wherein the cancer is selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL), and chronic lymphocytic leukemia/small lymphocytic lymphoma (CLL/SLL).

60. The method of claim 59, wherein the cancer is selected from marginal zone lymphoma (MZL), follicular lymphoma (FL), diffuse large B-cell lymphoma (DLBCL), and chronic lymphocytic leukemia/small lymphocytic lymphoma (CLL/SLL).

61. The method of claim 58, wherein the BCL-2 protein is Isoform 1 or Isoform 2.

* * * * *